United States Patent
Chou et al.

(10) Patent No.: US 11,155,577 B2
(45) Date of Patent: Oct. 26, 2021

(54) THIOL-ENE BASED PEPTIDE STAPLING AND USES THEREOF

(71) Applicant: University of Utah Research Foundation, Salt Lake City, UT (US)

(72) Inventors: Danny Hung-Chieh Chou, Salt Lake City, UT (US); Yuanxiang Wang, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 146 days.

(21) Appl. No.: 15/739,626

(22) PCT Filed: Jun. 22, 2016

(86) PCT No.: PCT/US2016/038788
§ 371 (c)(1),
(2) Date: Dec. 22, 2017

(87) PCT Pub. No.: WO2016/209978
PCT Pub. Date: Dec. 29, 2016

(65) Prior Publication Data
US 2019/0092810 A1    Mar. 28, 2019

Related U.S. Application Data

(60) Provisional application No. 62/183,133, filed on Jun. 22, 2015.

(51) Int. Cl.
*C07K 1/113* (2006.01)
*C07K 14/605* (2006.01)
(Continued)

(52) U.S. Cl.
CPC .............. *C07K 7/06* (2013.01); *C07K 1/006* (2013.01); *C07K 1/1133* (2013.01); *C07K 7/56* (2013.01);
(Continued)

(58) Field of Classification Search
CPC ........ A61K 38/26; C07K 1/006; C07K 1/113; C07K 1/1133; C07K 14/605
See application file for complete search history.

(56) References Cited

U.S. PATENT DOCUMENTS 7,192,713 B1    3/2007   Verdine et al.
7,723,469 B2    5/2010   Walensky et al.
(Continued)

FOREIGN PATENT DOCUMENTS

EP         0467699 A2    1/1992
WO    WO-1998/030575 A1    7/1998
(Continued)

OTHER PUBLICATIONS

Hoyle et al., Angew. Chem. Int. Ed., 2010, 49, 1540-1573. (Year: 2010).*
(Continued)

*Primary Examiner* — Jeffrey E. Russel
(74) *Attorney, Agent, or Firm* — Ballard Spahr, LLP

(57) ABSTRACT

In one aspect, the invention relates to compositions comprising stapled peptides, methods of making same, pharmaceutical compositions comprising same, and methods of treating various diseases, including, but not limited to, metabolic disorders such as diabetes, and cancers. The disclosed compounds comprise stapled peptides, including, but not limited to, stapled glucagon, axin, and p53 peptide homologues, which are useful as therapeutic agents for a variety of diseases as disclosed herein. The disclosed methods are useful in the preparation of a variety of stapled peptides, including stapled peptide homologues of glucagon, axin, and p53. This abstract is intended as a scanning tool for purposes of searching in the particular art and is not intended to be limiting of the present invention.

15 Claims, 27 Drawing Sheets
Specification includes a Sequence Listing.

(51) Int. Cl.
  C07K 7/06    (2006.01)
  C07K 7/56    (2006.01)
  C07K 1/00    (2006.01)
  C07K 14/47   (2006.01)
(52) U.S. Cl.
  CPC ........ *C07K 14/4748* (2013.01); *C07K 14/605* (2013.01)

(56)  References Cited

U.S. PATENT DOCUMENTS

| | | | |
|---|---|---|---|
| 7,786,072 | B2 | 8/2010 | Verdine et al. |
| 9,931,379 | B2* | 4/2018 | Lin .................. A61P 3/10 |
| 2006/0008848 | A1 | 1/2006 | Verdine et al. |
| 2009/0011986 | A1 | 1/2009 | Joshi et al. |
| 2009/0137456 | A1 | 5/2009 | Dimarchi et al. |
| 2009/0149630 | A1 | 6/2009 | Walensky et al. |
| 2009/0176964 | A1 | 7/2009 | Walensky et al. |
| 2010/0081611 | A1 | 4/2010 | Bradner et al. |
| 2010/0168388 | A1 | 7/2010 | Bernal et al. |
| 2010/0184645 | A1 | 7/2010 | Verdine et al. |
| 2011/0172126 | A1 | 7/2011 | Brust |
| 2012/0270800 | A1 | 10/2012 | Verdine et al. |
| 2013/0190504 | A1 | 7/2013 | David et al. |
| 2013/0197189 | A1 | 8/2013 | Aimetti et al. |
| 2014/0357841 | A1 | 12/2014 | Li et al. |
| 2015/0376227 | A1 | 12/2015 | Verdine et al. |

FOREIGN PATENT DOCUMENTS

| | | |
|---|---|---|
| WO | WO-2005/044839 A2 | 5/2005 |
| WO | WO-2008/061192 A2 | 5/2008 |
| WO | WO-2008/076904 A1 | 6/2008 |
| WO | WO-2008/095063 A1 | 8/2008 |
| WO | WO-2008/121767 A2 | 10/2008 |
| WO | WO-2010/011313 A2 | 1/2010 |
| WO | WO-2011/156686 A2 | 12/2011 |
| WO | WO-2013/123267 A1 | 8/2013 |
| WO | WO-2014/052650 A2 | 4/2014 |
| WO | WO-2014/083505 A1 | 6/2014 |
| WO | WO-2016/209978 A2 | 12/2016 |
| WO | WO-2018/017485 A1 | 1/2018 |

OTHER PUBLICATIONS

Yu et al. Sequential Michael addition thiol-ene and radical-mediated thiol-ene reactions in one-pot produced sequence-ordered polymers. Polymer Chemistry. 2015, vol. 6, pp. 1527-1532. (Year: 2015).*

Hoppmann, C. et al., Intramolecular Bridges Formed by Photoswitchable click Amino Acids. Bielstein J Org Chem. 2012; 8:884-9.

Wang, Y. and Chou, D.H.-C., A Thiol-Ene Coupling Approach to Native Peptide Stapling and Macrocyclization. Angew Chem Int Ed. 2015; 54(37):10931-4.

Supplementary European Search Report dated Jan. 16, 2019 by the European Patent Office for Patent Application No. 16815225.4, which was filed on Jan. 22, 2018 and published as EP 3310373 on Apr. 25, 2018 (Inventor—Chou et al.; Applicant—University of Utah Research Foundation; (10 pages).

International Preliminary Report on Patentability dated Jan. 22, 2019 by the International Searching Authority for Patent Application No. PCT/US2017/042406, which was filed on Jul. 17, 2017 and published as WO 2018/017485 on Jan. 25, 2018 (Inventor—Chou et al.; Applicant—University of Utah Research Foundation; (10 pages).

Almarasson, Ö. et al., Crystal Engineering of the Composition of Pharmaceutical Phases. Do Pharmaceutical Co-Crystals Represent a New Path to Improved Medicines? Chem Commun. 2004; 35(17):1889-96.

Bernal, F. et al., Reactivation of the p53 Tumor Suppressor Pathway by a Stapled p53 Peptide. J Am Chem Soc. 2007; 129(9):2456-7.

Bernal, F. et al., A Stapled p53 Helix Overcomes HDMX-Mediated Suppression of p53. Cancer Cell. 2010; 18(5):411-22.

Blackwell, H.E. and Grubbs, R.H., Highly Efficient Synthesis of Covalently Cross-Linked Peptide Helices by Ring-Closing Metathesis. Angew Chem Int Ed. 1998; 37(23):3281-4.

Brown, S.P. and Smith, A.B., Peptide/Protein Stapling and Unstapling: Introduction to s-Tetrazine, Photochemical Release, and Regeneration of the Peptide/Protein. J Am Chem Soc. 2015; 137(12):4034-7.

Chen, Y.H. et al., Determination of the Helix and β Form of Proteins in Aqueous Solution by Circular Dichroism. Biochemistry. 1974; 13(16):3350-9.

Cromm, P.M. et al., Hydrocarbon Stapled Peptides as Modulators of Biological Function. ACS Chem Biol. 2015; 10(6):1362-75.

De Araujo, A.D. et al., Comparative α-Helicity of Cyclic Pentapeptides in Water. Angew Chem Int Ed. 2014; 53(27):6965-9.

Grossman, T.N. et al., Inhibition of Oncogenic Wnt Signaling Through Direct Targeting of β-Catenin. Proc Natl Acad Sci USA. 2012; 109(44):17942-7.

Haney, C.M. et al., Promoting Peptide α-Helix Formation with Dynamic Covalent Oxime Side-Chain Cross-Links. Chem Commun. 2011; 47(39):10915-7.

Jo, H. et al., Development of a-Helical Calpain Probes by Mimicking a Natural Protein-Protein Interaction. J Am Chem Soc. 2012; 134(42):17704-13.

Kim, Y.-W. et al., Synthesis of All-Hydrocarbon Stapled a-Helical Peptides by Ring-Closing Olefin Metathesis. Nat Protoc. 2011; 6(6):761-71.

Lau, Y.H. et al., Functionalised Staple Linkages for Modulating the Cellular Activity of Stapled Peptides. Chem Sci. 2014; 5(5):1804-9.

Moellering, R.E. et al., Direct Inhibition of the NOTCH Transcription Factor Complex. Nature. 2009; 462(7270):182-8.

Schafmeister, C.E. et al., An All-Hydrocarbon Cross-Linking System for Enhancing the Helicity and Metabolic Stability of Peptides. J Am Chem Soc. 2000; 122(24):5891-2.

Sinclair, J.K.-L. et al., Inhibition Epidermal Growth Factor Receptor at a Distance. J Am Chem Soc. 2014; 136(32):11232-5.

Spokoyny, A.M. et al., A Perfluoroaryl-cysteine S(N)Ar Chemistry Approach to Unprotected Peptide Stapling. J Am Chem Soc. 2013; 135(16):5946-9.

Timmerman, P. et al., Rapid and Quantitative Cyclization of Multiple Peptide Loops onto Synthetic Scaffolds for Structural Mimicry of Protein Surfaces. ChemBioChem. 2005; 6(5):821-4.

Timmerman, P. et al., Functional Reconstruction and Synthetic Mimicry of a Conformational Epitope Using CLIPS Technology. J Mol Recgonit. 2007; 20(5):283-99.

Walensky, L.D. et al., Activation of Apoptosis in Vivo by a Hydrocarbon-Stapled BH3 Helix. Science. 2004; 305(5689):1466-70.

Walensky, L.D. and Bird, G.H., Hydrocarbon-Stapled Peptides: Principles, Practice, and Progress. J Med Chem. 2014; 57(15):6275-88.

International Search Report and Written Opinion dated Jan. 10, 2017 by the International Searching Authority for Patent Application No. PCT/US2016/038788, which was filed on Jun. 22, 2016 and published as WO 2016/209978 on Dec. 29, 2016 (Inventor—Chou et al.; University of Utah Research Foundation; (20 pages).

International Preliminary Report on Patentability dated Dec. 26, 2017 by the International Searching Authority for Patent Application No. PCT/US2016/038788, which was filed on Jun. 22, 2016 and published as WO 2016/209978 on Dec. 29, 2016 (Inventor—Chou et al.; University of Utah Research Foundation; (14 pages).

International Search Report and Written Opinion dated Dec. 14, 2017 by the International Searching Authority for Patent Application No. PCT/US2017/042406, which was filed on Jul. 17, 2017 and published as WO 2018/017485 on Jan. 25, 2018 (Inventor—Chou et al.; Applicant—University of Utah Research Foundation; (15 pages).

Non-final Office Action dated Sep. 30, 2020 for U.S. Appl. No. 16/316,989, filed Jan. 10, 2019, and published as US 2019/0292218 A1 on Sep. 26, 2019 (Inventor—Chou, et al.; Applicant—University of Utah Research Foundation; (15 pages).

* cited by examiner

SEQUENCE LISTING

```
<160> NUMBER OF SEQ ID NOS: 17

<210> SEQ ID NO 1
<211> LENGTH: 29
<212> TYPE: PRT
<213> ORGANISM: Artificial Construct
<220> FEATURE:
<223> OTHER INFORMATION: synthetic construct

<400> SEQUENCE: 1

His Ser Gln Gly Thr Phe Thr Ser Asp Tyr Ser Lys Tyr Leu Asp Ser
1               5                   10                  15

Cys Arg Ala Gln Cys Phe Val Gln Trp Leu Met Asn Thr
            20                  25

<210> SEQ ID NO 2
<211> LENGTH: 29
<212> TYPE: PRT
<213> ORGANISM: Artificial Construct
<220> FEATURE:
<223> OTHER INFORMATION: synthetic construct

<400> SEQUENCE: 2

His Ser Gln Gly Thr Phe Thr Ser Asp Tyr Ser Lys Tyr Leu Asp Ser
1               5                   10                  15

Arg Arg Ala Cys Asp Phe Val Cys Trp Leu Met Asn Thr
            20                  25

<210> SEQ ID NO 3
```

<211> LENGTH: 29
<212> TYPE: PRT
<213> ORGANISM: Artificial Construct
<220> FEATURE:
<223> OTHER INFORMATION: synthetic construct

<400> SEQUENCE: 3

His Ser Gln Gly Thr Phe Thr Ser Asp Tyr Ser Lys Tyr Leu Asp Ser
1               5                   10                  15
Arg Arg Ala Cys Asp Phe Val Gln Trp Leu Cys Asn Thr
            20                  25

<210> SEQ ID NO 4
<211> LENGTH: 29
<212> TYPE: PRT
<213> ORGANISM: Artificial Construct
<220> FEATURE:
<223> OTHER INFORMATION: synthetic construct

<400> SEQUENCE: 4

His Ser Gln Gly Thr Phe Thr Ser Asp Tyr Ser Lys Tyr Leu Asp Ser
1               5                   10                  15
Arg Arg Ala Gln Cys Phe Val Gln Trp Leu Met Cys Thr
            20                  25

<210> SEQ ID NO 5
<211> LENGTH: 29
<212> TYPE: PRT
<213> ORGANISM: Artificial Construct
<220> FEATURE:
<223> OTHER INFORMATION: synthetic construct

<400> SEQUENCE: 5

His Ser Gln Gly Thr Phe Thr Ser Asp Tyr Ser Lys Tyr Leu Asp Ser
1               5                   10                  15
Arg Arg Ala Gln Asp Phe Val Cys Trp Leu Met Cys Thr
            20                  25

<210> SEQ ID NO 6
<211> LENGTH: 8
<212> TYPE: PRT
<213> ORGANISM: Artificial Sequence
<220> FEATURE:
<223> OTHER INFORMATION: synthetic construct; Cys containing peptide

<400> SEQUENCE: 6

Tyr Cys Lys Glu Ala Cys Ala Leu
1               5

<210> SEQ ID NO 7
<211> LENGTH: 11
<212> TYPE: PRT
<213> ORGANISM: Artificial Sequence
<220> FEATURE:
<223> OTHER INFORMATION: synthetic construct; Cys containing peptide

<400> SEQUENCE: 7

Tyr Cys Lys Glu Ala Gly Gly Gly Ala Cys Leu
1               5                   10

<210> SEQ ID NO 8
<211> LENGTH: 15
<212> TYPE: PRT
<213> ORGANISM: Artificial Sequence
<220> FEATURE:
<223> OTHER INFORMATION: synthetic construct; Cys containing peptide

```
<220> FEATURE:
<221> NAME/KEY: MISC_FEATURE
<222> LOCATION: (5)..(5)
<223> OTHER INFORMATION: S5
<220> FEATURE:
<221> NAME/KEY: MISC_FEATURE
<222> LOCATION: (9)..(9)
<223> OTHER INFORMATION: S5

<400> SEQUENCE: 8

Glu Asn Pro Glu Xaa Ile Leu Asp Xaa His Val Gln Arg Val Met
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: synthetic construct; Cys containing peptide

<400> SEQUENCE: 9

Glu Asn Pro Glu Cys Ile Leu Asp Cys His Val Gln Arg Val Met
1               5                   10                  15

<210> SEQ ID NO 10
<211> LENGTH: 16
<212> TYPE: PRT
<213> ORGANISM: Artificial Sequence
<220> FEATURE:
<223> OTHER INFORMATION: synthetic construct; Cys containing peptide
<220> FEATURE:
<221> NAME/KEY: MISC_FEATURE
<222> LOCATION: (7)..(7)
<223> OTHER INFORMATION: R8
<220> FEATURE:
<221> NAME/KEY: MISC_FEATURE
<222> LOCATION: (14)..(14)
<223> OTHER INFORMATION: S5

<400> SEQUENCE: 10

Gln Ser Gln Gln Thr Phe Xaa Asn Leu Trp Arg Leu Leu Xaa Gln Asn
1               5                   10                  15

<210> SEQ ID NO 11
<211> LENGTH: 16
<212> TYPE: PRT
<213> ORGANISM: Artificial Sequence
<220> FEATURE:
<223> OTHER INFORMATION: synthetic construct; Cys containing peptide

<400> SEQUENCE: 11

Gln Ser Gln Gln Thr Phe Cys Asn Leu Trp Arg Leu Leu Cys Gln Asn
1               5                   10                  15

<210> SEQ ID NO 12
<211> LENGTH: 31
<212> TYPE: PRT
<213> ORGANISM: Homo sapiens

<400> SEQUENCE: 12

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 13
<211> LENGTH: 31
<212> TYPE: PRT
```

<213> ORGANISM: Artificial Sequence
<220> FEATURE:
<223> OTHER INFORMATION: synthetic construct; mutated GLP-1

<400> SEQUENCE: 13

His Ala Glu Gly Thr Phe Thr Ser Asp Val Ser Cys Tyr Leu Glu Cys
1               5                   10                  15

Gln Ala Ala Lys Glu Phe Ile Ala Trp Leu Val Lys Gly Arg Gly
            20                  25                  30

<210> SEQ ID NO 14
<211> LENGTH: 31
<212> TYPE: PRT
<213> ORGANISM: Artificial Sequence
<220> FEATURE:
<223> OTHER INFORMATION: synthetic construct; mutated GLP-1

<400> SEQUENCE: 14

His Ala Glu Gly Thr Phe Thr Ser Asp Val Ser Ser Tyr Leu Glu Gly
1               5                   10                  15

Gln Ala Ala Lys Glu Phe Ile Cys Trp Leu Val Cys Gly Arg Gly
            20                  25                  30

<210> SEQ ID NO 15
<211> LENGTH: 31
<212> TYPE: PRT
<213> ORGANISM: Artificial Sequence
<220> FEATURE:
<223> OTHER INFORMATION: synthetic construct; mutated GLP-1

<400> SEQUENCE: 15

His Ala Glu Gly Thr Phe Thr Ser Asp Val Ser Cys Tyr Leu Glu Cys
1               5                   10                  15

Gln Ala Ala Lys Glu Phe Ile Cys Trp Leu Val Lys Gly Arg Gly
            20                  25                  30

<210> SEQ ID NO 16
<211> LENGTH: 75
<212> TYPE: PRT
<213> ORGANISM: Artificial Sequence
<220> FEATURE:
<223> OTHER INFORMATION: synthetic construct; stapled peptide

<400> SEQUENCE: 16

Gly Gly Gly Met Val Asp Pro Val Gly Phe Ala Glu Ala Trp Lys Ala
1               5                   10                  15

Gln Phe Pro Asp Ser Glu Pro Pro Arg Met Glu Leu Arg Ser Val Cys
            20                  25                  30

Asp Ile Glu Gln Glu Leu Cys Arg Ala Glu Ala Arg Ile Arg Arg Asp
        35                  40                  45

Glu Gln Arg Val Asn Gln Glu Arg Phe Arg Met Ile Tyr Leu Glu Thr
    50                  55                  60

Leu Leu Ala Lys Glu Lys Lys Ser Tyr Asp Arg
65                  70                  75

<210> SEQ ID NO 17
<211> LENGTH: 75
<212> TYPE: PRT
<213> ORGANISM: Artificial Sequence
<220> FEATURE:
<223> OTHER INFORMATION: synthetic construct; stapled peptide

<400> SEQUENCE: 17

```
Gly Gly Gly Met Val Asp Pro Val Gly Phe Ala Glu Ala Trp Lys Ala
1               5                   10                  15
Gln Phe Pro Asp Ser Glu Pro Pro Arg Met Glu Leu Arg Ser Val Cys
            20                  25                  30
Asp Ile Glu Gln Glu Leu Cys Arg Ala Glu Ala Arg Ile Arg Arg Asp
        35                  40                  45
Glu Gln Arg Val Asn Gln Glu Arg Phe Arg Met Cys Tyr Leu Glu Thr
    50                  55                  60
Leu Leu Cys Lys Glu Lys Lys Ser Tyr Asp Arg
65              70                  75
```

THIOL-ENE BASED PEPTIDE STAPLING AND USES THEREOF

CROSS-REFERENCE TO RELATED APPLICATIONS

This Application is a national phase filing under 35 U.S.C. § 371 of International Application No. PCT/US2016/038788, filed on Jun. 22, 2016, which claims the benefit of U.S. Provisional Application No. 62/183,133, filed on Jun. 22, 2015, the contents of which are incorporated herein by reference in their entireties.

REFERENCE TO SEQUENCE LISTING

The Sequence Listing submitted on Jun. 04, 2021 as a text file named "21101_0311U2_ST25.txt," created on May 26, 2021, and having a size of 8,192 bytes is hereby incorporated by reference pursuant to 37 C.F.R. § 1.52(e)(5).

BACKGROUND

Peptides have attracted increasing attention as potential therapeutic agents. The biophysical properties of peptides allow for selective biological recognition of receptors, enzymes, and nucleic acids, thereby influencing cell-cell communication and/or controlling vital cellular functions, such as metabolism, immune defense, and cell division. Unfortunately, the utility of peptides as drugs is severely limited by several factors, including their rapid degradation by proteases under physiological conditions, their poor cell permeability, and their lack of binding specificity resulting from conformational flexibility.

Side chain crosslinking ("peptide stapling") is one of the numerous strategies that aim to stabilize and/or mimic peptide helices. Because peptide stapling necessitates macrocyclization, an entropically unfavorable process, very few reactions are known to date that give rise to reasonable yields without undesirable side reactions. One well-described reaction known to yield stapled peptides is based on using olefin-containing amino acids followed by ring-closing metathesis (RCM) (H. E. Blackwell and R. H. Grubbs, Angew. Chem. Int. Ed. 1998, 37, 3281-3284, and C. E. Schafmeister, et al., J. Am. Chem. Soc. 2000, 122, 5891-5892). Since this work, stapled peptides have developed into promising therapeutics to block protein-protein interactions or increase protease resistance (L. D. Walensky and G. H. Bird, J. Med. Chem. 2014, 57, 6275-6288; and P. M. Cromm, et al., ACS Chem. Biol. 2015). The hydrocarbon stapled peptides have been demonstrated in targeting intracellular proteins such as the BCL-2 family proteins (L. D. Walensky, et al., Science 2004, 305, 1466-1470) and NOTCH (R. E. Moellering, et al., Nature 2009, 462, 182-188), as well as extracellular proteins such as EGFR (J. K. Sinclair, et al., J. Am. Chem. Soc. 2014, 136, 11232-11235).

Due to its therapeutic potential, a growing number of studies reported alternative stapling methods such as lactamization (A. D, de Araujo, et al., Angew. Chem. Int. Ed. 2014, 53, 6965-6969), cycloaddition (Y. H. Lau, et al., Chem. Sci. 2014, 5, 1804-1809), oxime formation (C. M. Haney, et al., Chem. Commun. 2011, 47, 10915-10917), thioether (H. Jo, et al., J. Am. Chem. Soc. 2012, 134, 17704-17713; P. Timmerman, et al., ChemBioChem 2005, 6, 821-824; and P. Timmerman, et al., J. Mol. Recognit. 2007, 20, 283-299), and SNAr reaction (A. M. Spokoyny, et al., J Am Chem Soc 2013, 135, 5946-5949; and S. P. Brown and A. B. Smith, 3rd, J Am Chem Soc 2015, 137, 4034-4037). Although some of these methods still require unnatural amino acids (UAAs) in the peptide synthesis, both lactamization and cysteine modification circumvent the use of UAAs and could potentially be applied to recombinantly expressed peptides and proteins. However, the additional amide bond and perfluoroaromatic group may affect the properties of the stapled peptides and lead to unwanted interactions or immunogenic effects. Furthermore, the scope of linker length and types are limited due to the restriction on the ligation reaction.

Despite advances in reaction methods to synthesize stapled peptides, there is still a scarcity of synthetic methods capable of preparing stapled peptides with both the desired peptide properties and ease of synthesis. These needs and other needs are satisfied by the present invention.

SUMMARY

In accordance with the purpose(s) of the invention, as embodied and broadly described herein, the invention, in one aspect, relates to compositions comprising stapled peptides, methods of making same, pharmaceutical compositions comprising same, and methods of treating various diseases, including, but not limited to, metabolic disorders such as diabetes, and cancers. The disclosed compounds comprise stapled peptides, including, but not limited to, stapled glucagon, axin, and p53 peptide homologues, which are useful as therapeutic agents for a variety of diseases as disclosed herein. The disclosed methods are useful in the preparation of a variety of stapled peptides, including stapled peptide homologues of glucagon, axin, and p53.

Disclosed are compounds having a structure represented by a formula:

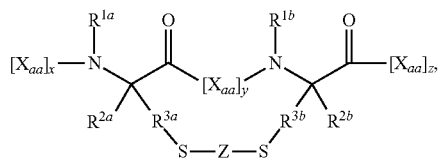

wherein each of x and z is independently an integer having a value of 0 to 100; wherein y is an integer having a value of 2 to 10; wherein each instance of $X_{aa}$ in $[X_{aa}]_x$ is, independently, a natural or unnatural amino acid residue when x is 1 to 100; and wherein $[X_{aa}]_x$ is hydrogen when x is 0; wherein each instance of $X_{aa}$ in $[X_{aa}]_y$ is, independently, a natural or unnatural amino acid; wherein each instance of $X_{aa}$ in $[X_{aa}]_z$ is, independently, a natural or unnatural amino acid when z is 1 to 100; and wherein $[X_{aa}]_z$ is hydroxy when z is 0; wherein each of $R^{1a}$ and $R^{1b}$ is independently hydrogen or an amino protecting group; wherein each of $R^{2a}$ and $R^{2b}$ is independently hydrogen or C1-C4 alkyl; wherein each of $R^{3a}$ and $R^{1b}$ is independently a C1-C4 alkylene; wherein Z is C5-C12 alkylene, —(C2-C6 alkylene)-O—(C2-C6 alkylene)-, —$(CH_2)_3$—$(OCH_2H_2)_q$—O—$CH_2)_3$—, or a moiety represented by a formula:

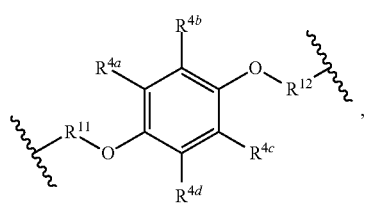

-continued

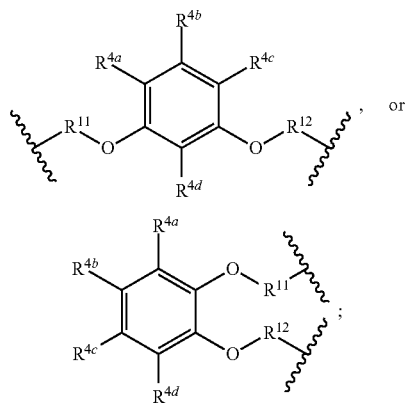

wherein q is 0, 1, 2, 3, or 4; wherein each of $R^{4a}$, $R^{4b}$, $R^{4c}$, and $R^{4d}$ is independently hydrogen, hydroxy, amino, C1-C4 alkyl, and —$CO_2H$; and wherein each of $R^{11}$ and $R^{12}$ is independently C3-C6 alkylene; or a pharmaceutically acceptable salt thereof.

Also disclosed are compounds having a structure represented by a formula:

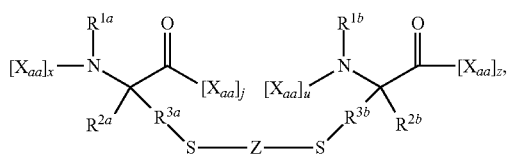

wherein each of j, u, x, and z is independently an integer having a value of 0 to 100; provided that j and x are not simultaneously 0; and provided that u and z are not simultaneously 0; wherein each instance of $X_{aa}$ in $[X_{aa}]_x$ is, independently, a natural or unnatural amino acid residue when x is 1 to 100; and wherein $[X_{aa}]_x$ is hydrogen when x is 0; wherein each instance of $X_{aa}$ in $[X_{aa}]_y$ is, independently, a natural or unnatural amino acid; wherein each instance of $X_{aa}$ in $[X_{aa}]_z$ is, independently, a natural or unnatural amino acid when z is 1 to 100; and wherein $[X_{aa}]_z$ is hydroxy when z is 0; wherein each of $R^{1a}$ and $R^{1b}$ is independently hydrogen or an amino protecting group; wherein each of $R^{2a}$ and $R^{2b}$ is independently hydrogen or C1-C4 alkyl; wherein each of $R^{3a}$ and $R^{3b}$ is independently a C1-C4 alkylene; wherein Z is C5-C12 alkylene, —(C2-C6 alkylene)-O—(C2-C6 alkylene)-, —$(CH_2)_3$—$(OCH_2CH_2)_q$—O—$(CH_2)_3$—, wherein q is 0, 1, 2, 3, or 4; or a moiety represented by a formula:

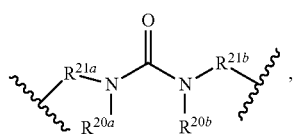

wherein each of $R^{20a}$ and $R^{20b}$ is independently selected from hydrogen and C1-C4 alkyl; and wherein each of $R^{21a}$ and $R^{21b}$ is independently C3-C6 alkylene; or a moiety represented by a formula:

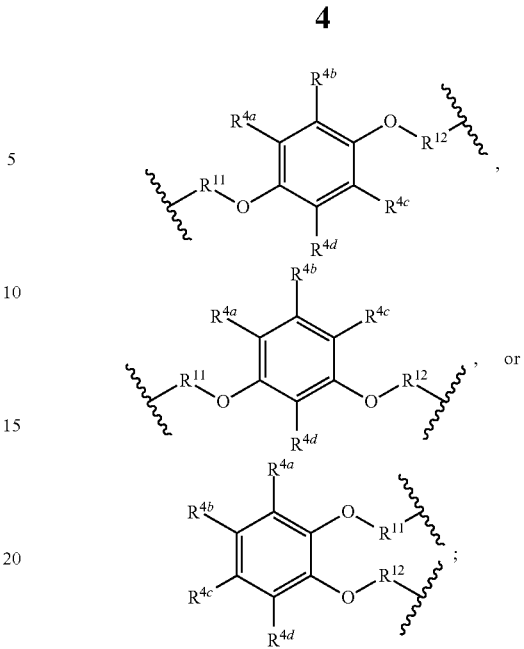

wherein q is 0, 1, 2, 3, or 4; wherein each of $R^{4a}$, $R^{4b}$, $R^{4c}$, and $R^{4d}$ is independently hydrogen, hydroxy, amino, C1-C4 alkyl, and —$CO_2H$; and wherein each of $R^{11}$ and $R^{12}$ is independently C3-C6 alkylene; or a pharmaceutically acceptable salt thereof.

Also disclosed are compounds having a structure represented by a formula:

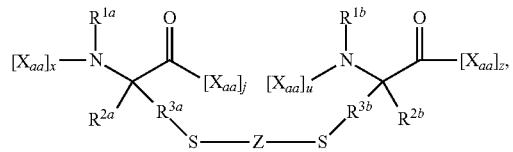

wherein each of j, u, x, and z is independently an integer having a value of 0 to 100; provided that j and x are not simultaneously 0; and provided that u and z are not simultaneously 0; wherein each instance of $X_{aa}$ in $[X_{aa}]_x$ is, independently, a natural or unnatural amino acid residue when x is 1 to 100; and wherein $[X_{aa}]_x$ is hydrogen when x is 0; wherein each instance of $X_{aa}$ in $[X_{aa}]_y$ is, independently, a natural or unnatural amino acid; wherein each instance of $X_{aa}$ in $[X_{aa}]_z$ is, independently, a natural or unnatural amino acid when z is 1 to 100; and wherein $[X_{aa}]_z$ is hydroxy when z is 0; wherein each of $R^{1a}$ and $R^{1b}$ is independently hydrogen or an amino protecting group; wherein each of $R^{2a}$ and $R^{2b}$ is independently hydrogen or C1-C4 alkyl; wherein each of $R^{3a}$ and $R^{3b}$ is independently a C1-C4 alkylene; wherein Z is C5-C12 alkylene, —(C2-C6 alkylene)-O—(C2-C6 alkylene)-, —$(CH_2)_3$—$(OCH_2CH_2)_q$—O—$(CH_2)_3$—, or a moiety represented by a formula:

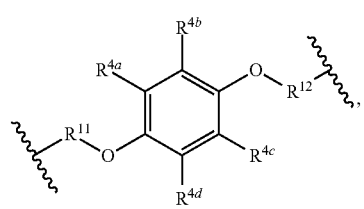

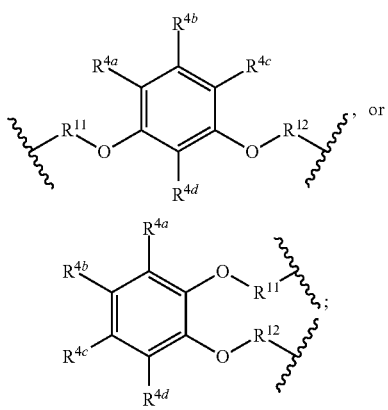

wherein q is 0, 1, 2, 3, or 4; wherein each of $R^{4a}$, $R^{4b}$, $R^{4c}$, and $R^{4d}$ is independently hydrogen, hydroxy, amino, C1-C4 alkyl, and —$CO_2H$; and wherein each of $R^{11}$ and $R^{12}$ is independently C3-C6 alkylene; or a pharmaceutically acceptable salt thereof.

Also disclosed are method of stapling a peptide having two thiol functionalities with a linker having two alkene functionalities, the method comprising the step of reacting the two thiol functionalities with the two alkene functionalities.

Also disclosed are methods of preparing a stapled peptide, the method comprising reacting a bis-terminal diene with a peptide comprising a first amino acid residue with a thiol-containing R group and a second amino acid residue with a thiol-containing R group.

Also disclosed are methods of preparing a stapled peptide, the method comprising the steps of providing a peptide having the structure represented by the formula:

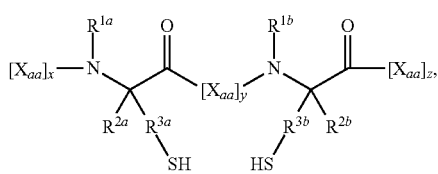

wherein each of x and z is independently an integer having a value of 0 to 100; wherein y is an integer having a value of 1 to 20; wherein each instance of $X_{aa}$ is, independently, a natural or unnatural amino acid; wherein each of $R^{1a}$ and $R^{1b}$ is independently hydrogen or an amino protecting group; wherein each of $R^{2a}$ and $R^{2b}$ is independently hydrogen or C1-C4 alkyl; wherein each of $R^{3a}$ and $R^{3b}$ is independently a C1-C4 alkyl; providing a diene having the structure represented by the formula:

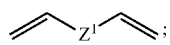

wherein $Z^1$ is C1-C8 alkyl, C3-C8 ether, C6-C8 polyether, or a moiety represented by a formula:

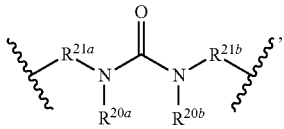

wherein each of $R^{20a}$ and $R^{20b}$ is independently selected from hydrogen and C1-C4 alkyl; and wherein each of $R^{21a}$ and $R^{21b}$ is independently C3-C6 alkylene; or a moiety represented by a formula:

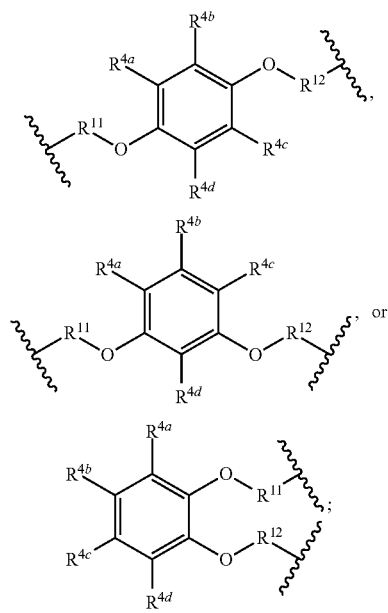

wherein each of $R^{4a}$, $R^{4b}$, $R^{4c}$, and $R^{4d}$ is independently hydrogen, hydroxy, amino, C1-C4 alkyl, and —$CO_2H$; and wherein each of $R^{13}$ and $R^{14}$ is independently C1-C4 alkyl; reacting the peptide and the diene in the presence of radical initiator; thereby forming the stapled peptide.

Also disclosed are methods of preparing a stapled peptide, the method comprising the steps of: (a) providing a peptide having the structure represented by the formula:

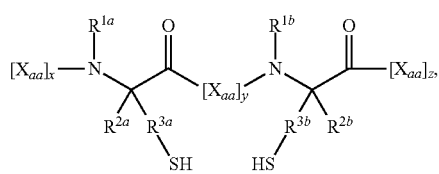

wherein each of x and z is independently an integer having a value of 0 to 100; wherein y is an integer having a value of 1 to 20; wherein each instance of $X_{aa}$ is, independently, a natural or unnatural amino acid; wherein each of $R^{1a}$ and $R^{1b}$ is independently hydrogen or an amino protecting group; wherein each of $R^{2a}$ and $R^{2b}$ is independently hydrogen or C1-C4 alkyl; wherein each of $R^{3a}$ and $R^{3b}$ is independently a C1-C4 alkyl; (b) providing a diene having the structure represented by the formula:

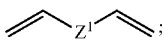

wherein $Z^1$ is C1-C8 alkyl, C3-C8 ether, C6-C8 polyether, or a moiety represented by a formula:

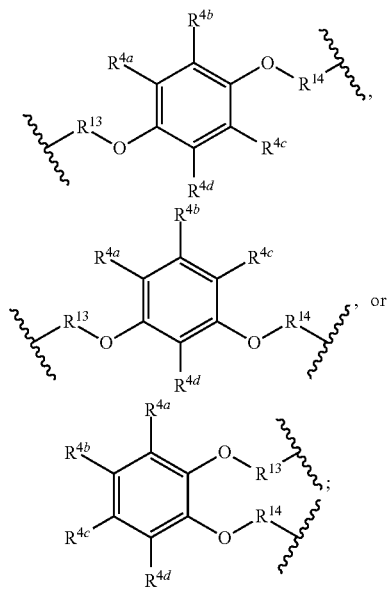

wherein each of $R^{4a}$, $R^{4b}$, $R^{4c}$, and $R^{4d}$ is independently hydrogen, hydroxy, amino, C1-C4 alkyl, and —$CO_2H$; and wherein each of $R^{13}$ and $R^{14}$ is independently C1-C4 alkyl; and (c) reacting the peptide and the diene in the presence of radical initiator; thereby forming the stapled peptide.

Also disclosed are methods of preparing a stapled peptide, the method comprising the steps of: providing a first peptide and a second peptide having, respectively, the structure represented by the formulas:

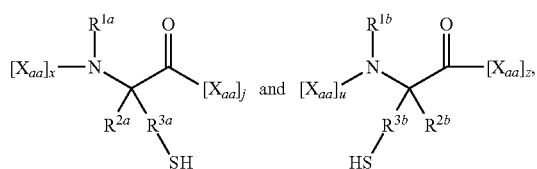

wherein each of j, u, x, and z is independently an integer having a value of 0 to 100; provided that j and x are not simultaneously 0; and provided that u and z are not simultaneously 0; wherein each instance of $X_{aa}$ is, independently, a natural or unnatural amino acid; wherein each of $R^{1a}$ and $R^{1b}$ is independently hydrogen or an amino protecting group; wherein each of $R^{2a}$ and $R^{2b}$ is independently hydrogen or C1-C4 alkyl; wherein each of $R^{3a}$ and $R^{3b}$ is independently a C1-C4 alkyl; providing a diene having the structure represented by the formula:

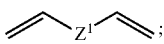

wherein $Z^1$ is C1-C8 alkyl, C3-C8 ether, C6-C8 polyether, or a moiety represented by a formula:

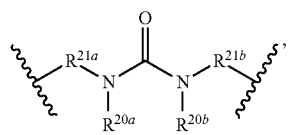

wherein each of $R^{20a}$ and $R^{20b}$ is independently selected from hydrogen and C1-C4 alkyl; and wherein each of $R^{21a}$ and $R^{21b}$ is independently C3-C6 alkylene; or a moiety represented by a formula:

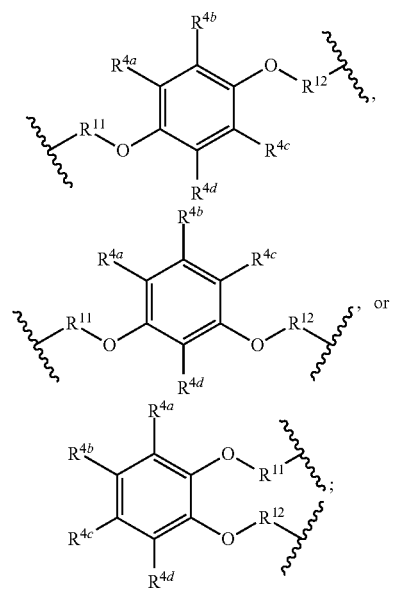

wherein each of $R^{4a}$, $R^{4b}$, $R^{4c}$, and $R^{4d}$ is independently hydrogen, hydroxy, amino, C1-C4 alkyl, and —$CO_2H$; and wherein each of $R^{13}$ and $R^{14}$ is independently C1-C4 alkyl; reacting the peptide and the diene in the presence of radical initiator; thereby forming the stapled peptide.

Also disclosed are methods of preparing a stapled peptide, the method comprising the steps of: (a) providing a first peptide and a second peptide having, respectively, the structure represented by the formulas:

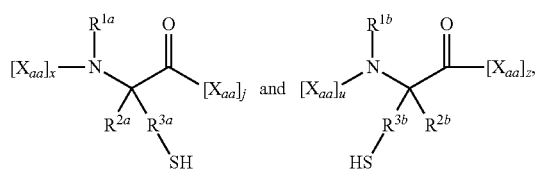

wherein each of j, u, x, and z is independently an integer having a value of 0 to 100; provided that j and x are not simultaneously 0; and provided that u and z are not simultaneously 0; wherein each instance of $X_{aa}$ is, independently, a natural or unnatural amino acid; wherein each of $R^{1a}$ and $R^{1b}$ is independently hydrogen or an amino protecting group; wherein each of $R^{2a}$ and $R^{2b}$ is independently hydrogen or C1-C4 alkyl; wherein each of $R^{3a}$ and $R^{3b}$ is independently a C1-C4 alkyl; (b) providing a diene having the structure represented by the formula:

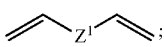

wherein $Z^1$ is C1-C8 alkyl, C3-C8 ether, C6-C8 polyether, or a moiety represented by a formula:

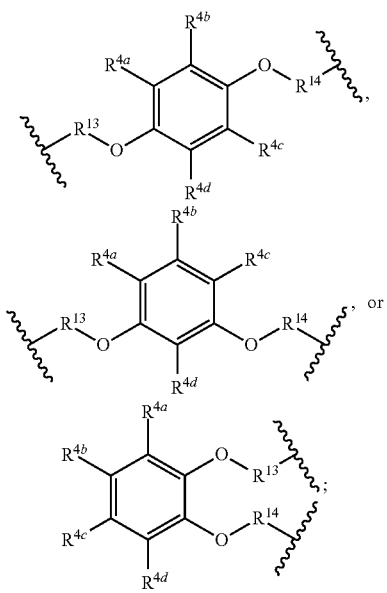

wherein each of $R^{4a}$, $R^{4b}$, $R^{4c}$, and $R^{4d}$ is independently hydrogen, hydroxy, amino, C1-C4 alkyl, and —$CO_2H$; and wherein each of $R^{13}$ and $R^{14}$ is independently C1-C4 alkyl; and (c) reacting the peptide and the diene in the presence of radical initiator; thereby forming the stapled peptide.

Also disclosed are stapled peptides prepared by any of the disclosed methods.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the invention.

Figure 1:
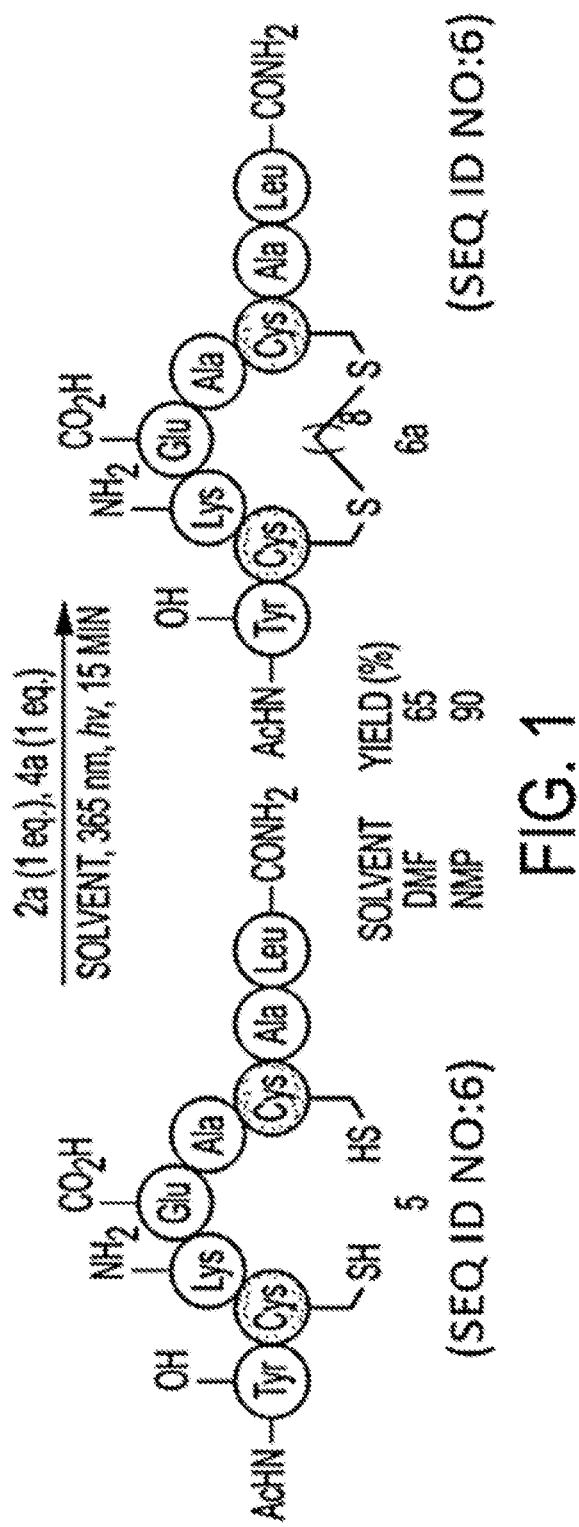
FIG. 1 shows a representative model thiol-ene two-component coupling reaction between an exemplary unprotected peptide, peptide 5, and an exemplary diene, 1,7-octadiene (also indicated as compound 2a). The compound numbers correspond to those used in the Examples and shown in FIGS. 1 and 2.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

A. Definitions

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects. In some aspects of the disclosed methods, the subject has been diagnosed with a need for treatment of one or more disorder, e.g., diabetes or cancer, prior to the administering step.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein.

As used herein, the phrase "identified to be in need of treatment for a disorder," or the like, refers to selection of a subject based upon need for treatment of the disorder. For example, a subject can be identified as having a need for treatment of a disorder (e.g., a disorder such as diabetes or cancer) based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically, that is, administered for prevention of a disease or condition.

The term "contacting" as used herein refers to bringing a disclosed compound and a cell, target of a disclosed peptide, or other biological entity together in such a manner that the compound can affect the activity of the target (e.g., spliceosome, cell, etc.), either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder, the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

"Stapling," as used herein, is a process by which two terminally unsaturated amino acid side chains in a polypeptide chain react with each in the presence of an appropriate ring closing metathesis catalyst to generate a C—C double bonded cross-link between the two amino acids (a "staple"). Stapling engenders constraint on a secondary structure, such as an alpha helical structure. The length and geometry of the cross-link can be optimized to improve the yield of the desired secondary structure content. The constraint provided can, for example, prevent the secondary structure to unfold and/or can reinforce the shape of the secondary structure, and thus makes the secondary structure more stable. Multiple stapling is also referred to herein as "stitching." See, e.g., U.S. Pat. Nos. 7,192,713; 7,723,469; 7,786,072; U.S. Patent Application Publication Nos: 2010-0184645; 2010-0168388; 2010-0081611; 2009-0176964; 2009-0149630; 2006-0008848; PCT Application Publication Nos: WO 2010/011313; WO 2008/121767; WO 2008/095063; WO 2008/061192; and WO 2005/044839, which depict stapling and stitching of polypeptides. In certain embodiments, stapling may occur at i,i+3, i,i+4, and/or i,i+7 positions of the polypeptide.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "A$^1$," "A$^2$," "A$^3$," and "A$^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol." and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more CH$_2$ groups linked to one another. The polyalkylene group can be represented by the formula —(CH$_2$)$_a$—, where "a" is an integer of from 2 to 500.

The terms "alkoxy" and "alkoxyl" as used herein to refer to an alkyl or cycloalkyl group bonded through an ether linkage, that is, an "alkoxy" group can be defined as —OA$^1$ where $A^1$ is alkyl or cycloalkyl as defined above. "Alkoxy" also includes polymers of alkoxy groups as just described; that is, an alkoxy can be a polyether such as —$OA^1$-$OA^2$ or —$OA^1$-$OA^2)_a$-$OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula —$NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)$A^1$ or —C(O)O$A^1$, where $A^1$ can be alkyl, cycloalkyl, alkenyl, cycloalkenyl, alkynyl, cycloalkynyl, aryl, or heteroaryl group as described herein. The term "polyester" as used herein is represented by the formula -($A^1$O(O)C-$A^2$-C(O)O)$_a$— or -($A^1$O(O)C-$A^2$-OC(O))$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, an alkyl, cycloalkyl, alkenyl, cycloalkenyl, alkynyl, cycloalkynyl, aryl, or heteroaryl group described herein. The term "polyether" as used herein is represented by the formula -($A^1$O-$A^2$O)$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "halide" as used herein refers to the halogens fluorine, chlorine, bromine, and iodine.

The term "heterocycle," as used herein refers to single and multi-cyclic aromatic or non-aromatic ring systems in which at least one of the ring members is other than carbon. Heterocycle includes azetidine, dioxane, furan, imidazole, isothiazole, isoxazole, morpholine, oxazole, oxazole, including, 1,2,3-oxadiazole, 1,2,5-oxadiazole and 1,3,4-oxadiazole, piperazine, piperidine, pyrazine, pyrazole, pyridazine, pyridine, pyrimidine, pyrrole, pyrrolidine, tetrahydrofuran, tetrahydropyran, tetrazine, including 1,2,4,5-tetrazine, tetrazole, including 1,2,3,4-tetrazole and 1,2,4,5-tetrazole, thiadiazole, including, 1,2,3-thiadiazole, 1,2,5-thiadiazole, and 1,3,4-thiadiazole, thiazole, thiophene, triazine, including 1,3,5-triazine and 1,2,4-triazine, triazole, including, 1,2,3-triazole, 1,3,4-triazole, and the like.

The term "hydroxyl" as used herein is represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" as used herein is represented by the formula —$N_3$.

The term "nitro" as used herein is represented by the formula —$NO_2$.

The term "nitrile" as used herein is represented by the formula —CN.

The term "silyl" as used herein is represented by the formula -$SiA^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —$S(O)A^1$, —$S(O)_2A^1$, —$OS(O)_2A^1$, or —$OS(O)_2OA^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —$S(O)_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" is used herein is represented by the formula $A'S(O)_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; —$(CH_2)_{0-4}R°$; —$(CH_2)_{0-4}OR°$; —O$(CH_2)_{0-4}$ R°, —O—$(CH_2)_{0-4}C(O)OR°$; —$(CH_2)_{0-4}CH(OR°)_2$; —$(CH_2)_{0-4}SR°$; —$(CH_2)_{0-4}Ph$, which may be substituted with R°; —$(CH_2)_{0-4}O(CH_2)_{0-1}Ph$ which may be substituted with R°; —CH=CHPh, which may be substituted with R°; —$(CH_2)_{0-4}O(CH_2)_{0-1}$-pyridyl which may be substituted with R°; —$NO_2$; —CN; —$N_3$; —$(CH_2)_{0-4}N(R°)_2$; —$(CH_2)_{0-4}N(R°)C(O)R°$; —$N(R°)C(S)R°$; —$(CH_2)_{0-4}N(R°)C(O)NR°_2$; —$N(R°)C(S)NR°_2$; —$(CH_2)_{0-4}N(R°)C(O)OR°$; —$N(R°)N(R°)C(O)R°$; —$N(R°)N(R°)C(O)NR°_2$; —$N(R°)N(R°)C(O)OR°$; —$(CH_2)_{0-4}C(O)R°$; —C(S)R°; —$(CH_2)_{0-4}C(O)OR°$; —$(CH_2)_{0-4}C(O)SR°$; —$(CH_2)_{0-4}C(O)OSiR°$; —$(CH_2)_{0-4}OC(O)R°$; —$OC(O)(CH_2)_{0-4}SR$—, SC(S)SR°; —$(CH_2)_{0-4}SC(O)R°$; —$(CH_2)_{0-4}C(O)NR°_2$; —C(S)NR°_2; —C(S)SR°; —SC(S)SR°, —$(CH_2)_{0-4}OC(O)NR°_2$; —C(O)N(OR°)R°; —C(O)C(O)R°; —C(O)CH_2C(O)R°; —C(NOR°)R°; —$(CH_2)_{0-4}SSR°$; —$(CH_2)_{0-4}S(O)_2R°$; —$(CH_2)_{0-4}S(O)_2 OR°$; —$(CH_2)_{0-4}OS(O)_2R°$; —$S(O)_2NR°_2$; —$(CH_2)_{0-4}S(O)R°$; —N(R°)S(O)_2NR°_2; —N(R°)S(O)_2R°; —N(OR°)R°; —C(NH)NR°_2; —P(O)_2R°; —P(O)R°_2; —OP(O)R°_2; —OP(O)(OR°)_2; SiR°_3; —$(C_{1-4}$ straight or branched alkylene)O—N(R°)_2; or —$(C_{1-4}$ straight or branched alkylene)C(O)O—N(R°)_2, wherein each R° may be substituted as defined below and is independently hydrogen, $C_{1-6}$ aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^●$, -(haloR$^●$), —(CH$_2$)$_{0-2}$OH, —(CH$_2$)$_{0-2}$OR$^●$, —(CH$_2$)$_{0-2}$CH(OR$^●$)$_2$; —O(haloR$^●$), —CN, —N$_3$, —(CH$_2$)$_{0-2}$C(O)R$^●$, —(CH$_2$)$_{0-2}$C(O)OH, —(CH$_2$)$_{0-2}$C(O)OR$^●$, —(CH$_2$)$_{0-2}$SR$^●$, —(CH$_2$)$_{0-2}$SH, —(CH$_2$)$_{0-2}$NH$_2$, —(CH$_2$)$_{0-2}$NHR$^●$, —(CH$_2$)$_{0-2}$NR$^●_2$, —NO$_2$, —SiR$^●_3$, —OSiR$^●_3$, —C(O)SR$^●$, —(C$_{1-4}$ straight or branched alkylene)C(O)OR$^●$, or —SSR$^●$ wherein each R$^●$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R$^o$ include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^●$, -(haloR$^●$), —OH, —OR$^●$, —O(haloR$^●$), —CN, —C(O)OH, —C(O)OR$^●$, —NH$_2$, —NHR$^●$, —NR$^●_2$, or —NO$_2$, wherein each R$^●$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^†$, —NR$^†_2$, —C(O)R$^†$, —C(O)OR$^†$, —C(O)C(O)R$^†$, —C(O)CH$_2$C(O)R$^†$, —S(O)$_2$R$^†$, —S(O)$_2$NR$^†_2$, —C(S)NR$^†_2$, —C(NH)NR$^†_2$, or —N(R$^†$)S(O)$_2$R$^†$; wherein each R$^†$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^†$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^†$ are independently halogen, —R$^●$, -(haloR$^●$), —OH, —OR$^●$, —O(haloR$^●$), —CN, —C(O)OH, —C(O)OR$^●$, —NH$_2$, —NHR$^●$, —NR$^●_2$, or —NO$_2$, wherein each R$^●$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, brosylate, and halides.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms. 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure

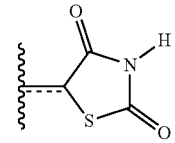

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms. 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5, 6, 7, 8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvate or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et, al., The Royal Society of Chemistry, 1889-1896, 2004. Examples of co-crystals include p-toluenesulfonic acid and benzenesulfonic acid.

It is also appreciated that certain compounds described herein can be present as an equilibrium of tautomers. For example, ketones with an a-hydrogen can exist in an equilibrium of the keto form and the enol form.

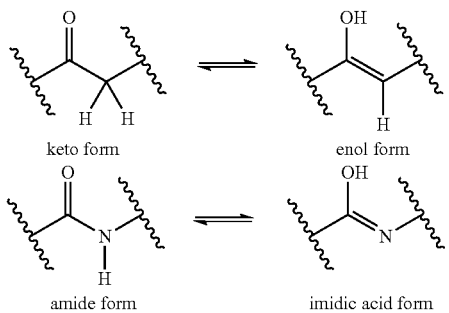

Likewise, amides with an N-hydrogen can exist in an equilibrium of the amide form and the imidic acid form. Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

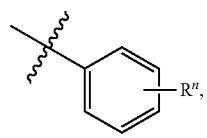

which is understood to be equivalent to a formula:

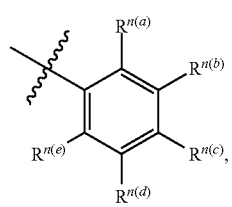

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.). Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplemental Volumes (Elsevier Science Publishers. 1989); Organic Reactions, Volumes 1-40 (John Wiley and Sons, 1991); March's Advanced Organic Chemistry, (John Wiley and Sons, 4th Edition), and Larock's Comprehensive Organic Transformations (VCH Publishers Inc. 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc, of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that

B. Peptides

In one aspect, the invention relates to stapled peptide compositions, including, but not limited to, stapled peptide homologues of glucagon, axin, and p53. More specifically, in one aspect, the present invention relates to stapled glucagon peptides.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Stapled Peptide Compositions

In one aspect, the invention relates to a compound having a structure represented by a formula:

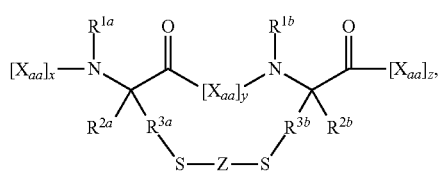

wherein each of x and z is independently an integer having a value of 0 to 100; wherein y is an integer having a value of 2 to 10; wherein each instance of $X_{aa}$ in $[X_{aa}]_x$ is, independently, a natural or unnatural amino acid residue when x is 1 to 100; and wherein $[X_{aa}]_x$ is hydrogen when x is 0; wherein each instance of $X_{aa}$ in $[X_{aa}]_y$ is, independently, a natural or unnatural amino acid; wherein each instance of $X_{aa}$ in $[X]_z$ is, independently, a natural or unnatural amino acid when z is 1 to 100; and wherein $[X_{aa}]_z$ is hydroxy when z is 0; wherein each of $R^{1a}$ and $R^{1b}$ is independently hydrogen or an amino protecting group; wherein each of $R^{2a}$ and $R^{2b}$ is independently hydrogen or C1-C4 alkyl; wherein each of $R^{3a}$ and $R^{3b}$ is independently a C1-C4 alkylene; wherein Z is C5-C12 alkylene, —(C2-C6 alkylene)-O—(C2-C6 alkylene)-, —(CH$_2$)$_3$—(OCH$_2$CCH$_2$)$_q$—O—(CH$_2$)$_3$—, wherein q is 0, 1, 2, 3, or 4; or a moiety represented by a formula:

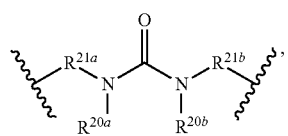

wherein each of $R^{21a}$ and $R^{20b}$ is independently selected from hydrogen and C1-C4 alkyl; and wherein each of $R^{21a}$ and $R^{21b}$ is independently C3-C6 alkylene; or a moiety represented by a formula:

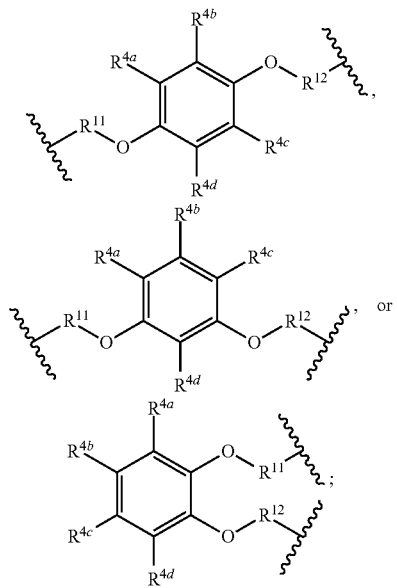

wherein each of $R^{4a}$, $R^{4b}$, $R^{4c}$, and $R^{4d}$ is independently selected from hydrogen, hydroxy, amino, C1-C4 alkyl, and —CO$_2$H; and wherein each of $R^{11}$ and $R^{12}$ is independently C3-C6 alkylene; or a pharmaceutically acceptable salt thereof.

In one aspect, the invention relates to a peptide having a structure represented by a formula:

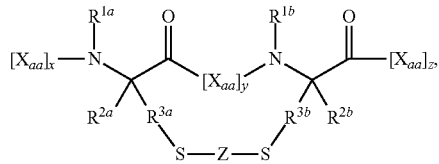

wherein each of x and z is independently an integer having a value of 0 to 100; wherein y is an integer having a value of 2 to 10; wherein each instance of $X_{aa}$ in $[X_{aa}]_x$ is, independently, a natural or unnatural amino acid residue when x is 1 to 100; and wherein $[X_{aa}]_x$ is hydrogen when x is 0; wherein each instance of $X_{aa}$ in $[X_{aa}]_y$ is, independently, a natural or unnatural amino acid; wherein each instance of $X_{aa}$ in $[X]_z$ is, independently, a natural or unnatural amino acid when z is 1 to 100; and wherein $[X_{aa}]_z$ is hydroxy when z is 0; wherein each of $R^{1a}$ and $R^{1b}$ is independently hydrogen or an amino protecting group; wherein each of $R^{2a}$ and $R^{2b}$ is independently hydrogen or C1-C4 alkyl; wherein each of $R^{3a}$ and $R^b$ is independently a C1-C4 alkylene; wherein Z is C5-C12 alkylene, —(C2-C6 alkylene)-O—(C2-C6 alkylene)-, —(CH$_2$)$_3$—(OCH$_2$CH$_2$)$_q$—O—(CH$_2$)$_3$—, or a moiety represented by a formula:

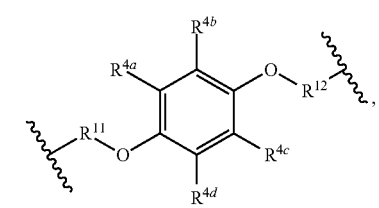

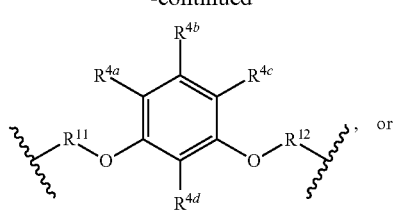, or

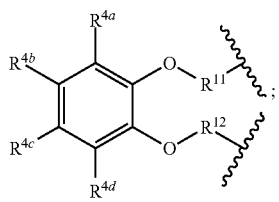;

wherein q is 0, 1, 2, 3, or 4; wherein each of $R^{4a}$, $R^{4b}$, $R^{4c}$, and $R^{4d}$ is independently hydrogen, hydroxy, amino, C1-C4 alkyl, and —$CO_2H$; and wherein each of $R^{11}$ and $R^{12}$ is independently C3-C6 alkylene; or a pharmaceutically acceptable salt thereof. In a further aspect, the peptide further comprises acetylation of a carboxy terminal amino acid residue.

In a further aspect, the invention relates to a peptide having a structure represented by a formula:

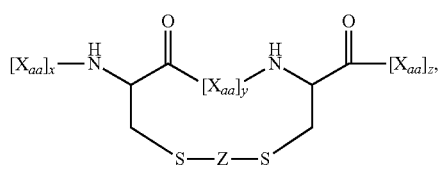

wherein each of x and z is independently an integer having a value of 2 to 15; wherein y is 2, 3, 6 or 10; wherein each instance of $X_{aa}$ in $[X_{aa}]_x$ is, independently, a natural or unnatural amino acid residue; wherein each instance of $X_{aa}$ in $[X_{aa}]_y$ is, independently, a natural or unnatural amino acid; wherein each instance of $X_{aa}$ in $[X_{aa}]_z$ is, independently, a natural or unnatural amino acid; and wherein Z is a moiety represented by a formula:

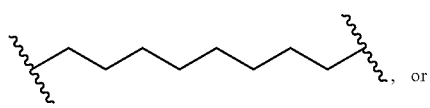, or

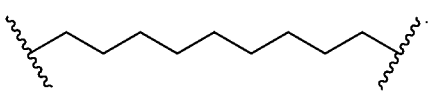.

In a further aspect, the invention relates to a peptide having a structure represented by a formula:

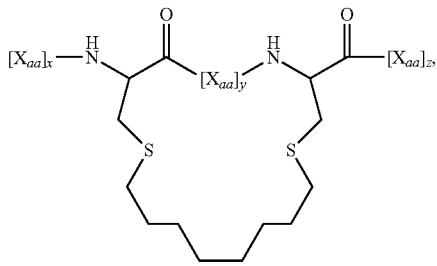

wherein each of x and z is independently an integer having a value of 0 to 100; wherein y is an integer having a value of 2 to 10; wherein each instance of $X_{aa}$ in $[X_{aa}]_x$ is, independently, a natural or unnatural amino acid residue when x is 1 to 100; and wherein $[X_{aa}]_x$ is hydrogen when x is 0; wherein each instance of $X_{aa}$ in $[X_{aa}]_y$ is, independently, a natural or unnatural amino acid; wherein each instance of $X_{aa}$ in $[X_{aa}]_z$ is, independently, a natural or unnatural amino acid when z is 1 to 100; and wherein $[X_{aa}]_z$ is hydroxy when z is 0.

In a further aspect, the invention relates to a peptide having a structure represented by a formula:

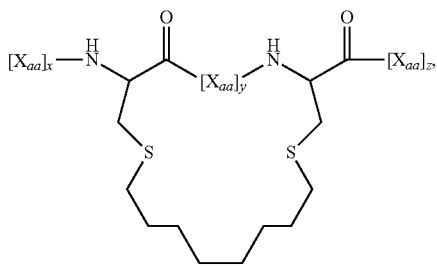

wherein each of x and z is independently an integer having a value of 2 to 15; wherein y is 2, 3, 6 or 10; wherein each instance of $X_{aa}$ in $[X_{aa}]_x$ is, independently, a natural or unnatural amino acid residue; wherein each instance of $X_{aa}$ in $[X_{aa}]_y$ is, independently, a natural or unnatural amino acid; and wherein each instance of $X_{aa}$ in $[X_{aa}]_z$ is, independently, a natural or unnatural amino acid.

In a further aspect, the invention relates to a peptide having a structure represented by a formula:

wherein each of x and z is independently an integer having a value of 0 to 100; wherein y is an integer having a value of 2 to 10; wherein each instance of $X_{aa}$ in $[X_{aa}]_x$ is, independently, a natural or unnatural amino acid residue when x is 1 to 100; and wherein $[X_{aa}]_x$ is hydrogen when x is 0; wherein each instance of $X_{aa}$ in $[X_{aa}]_y$ is, independently, a natural or unnatural amino acid; wherein each instance of $X_{aa}$ in $[X_{aa}]_z$ is, independently, a natural or unnatural amino acid when z is 1 to 100; and wherein $[X_{aa}]_z$ is hydroxy when z is 0.

In a further aspect, the invention relates to a peptide having a structure represented by a formula:

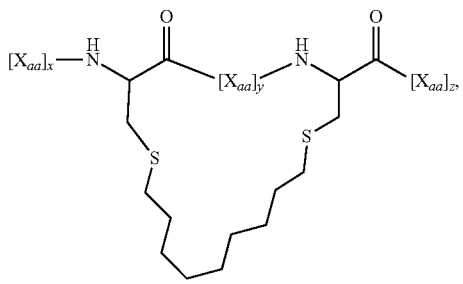

wherein each of x and z is independently an integer having a value of 2 to 15; wherein y is 2, 3, 6 or 10; wherein each instance of $X_{aa}$ in $[X_{aa}]_x$ is, independently, a natural or unnatural amino acid residue; wherein each instance of $X_{aa}$ in $[X_{aa}]_y$ is, independently, a natural or unnatural amino acid; and wherein each instance of $X_{aa}$ in $[X_{aa}]_z$ is, independently, a natural or unnatural amino acid.

In a further, each of x and z is independently an integer having a value of 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100.

In various aspects, each of x and z is independently an integer having a value of 0 to 100. In a further aspect, each of x and z is independently an integer having a value of 0 to 90. In a still further aspect, each of x and z is independently an integer having a value of 0 to 80. In a yet further aspect, each of x and z is independently an integer having a value of 0 to 70. In an even further aspect, each of x and z is independently an integer having a value of 0 to 60. In a still further aspect, each of x and z is independently an integer having a value of 0 to 50. In a yet further aspect, each of x and z is independently an integer having a value of 0 to 40. In an even further aspect, each of x and z is independently an integer having a value of 0 to 30. In a still further aspect, each of x and z is independently an integer having a value of 0 to 20. In a yet further aspect, each of x and z is independently an integer having a value of 0 to 10.

In a further aspect, each of x and z is independently an integer having a value of 1 to 15. In a still further aspect, each of x and z is independently an integer having a value of 2 to 15. In a yet further aspect, each of x and z is independently an integer having a value of 3 to 15. In an even further aspect, each of x and z is independently an integer having a value of 4 to 15. In a still further aspect, each of x and z is independently an integer having a value of 5 to 15. In a yet further aspect, each of x and z is independently an integer having a value of 6 to 15. In an even further aspect, each of x and z is independently an integer having a value of 7 to 15. In a still further aspect, each of x and z is independently an integer having a value of 8 to 15. In a yet further aspect, each of x and z is independently an integer having a value of 9 to 15. In an even further aspect, each of x and z is independently an integer having a value of 10 to 15.

In various aspects, y is an integer having a value of 2 to 10. In a further aspect, y is an integer having a value of 2, 3, 6 or 10.

In a further aspect, y is an integer having a value of 2. In a still further aspect, y is an integer having a value of 3. In a yet further aspect, y is an integer having a value of 4. In an even further aspect, y is an integer having a value of 5. In a still further aspect, y is an integer having a value of 6. In a yet further aspect, y is an integer having a value of 7. In an even further aspect, y is an integer having a value of 8. In a still further aspect, y is an integer having a value of 9. In a yet further aspect, y is an integer having a value of 10.

In various aspects, q is 0, 1, 2, 3, or 4. In a further aspect, q is 0, 1, 2, or 3. In a still further aspect, q is 0, 1, or 2. In a yet further aspect, q is 0 or 1. In a yet further aspect, q is 0. In a still further aspect, q is 1. In a yet further aspect, q is 2. In a yet further aspect, q is 3. In an even further aspect q is 4.

In one aspect, the invention relates to a compound having a structure represented by a formula:

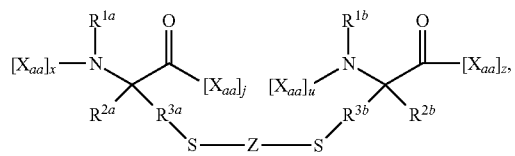

wherein each of j, u, x, and z is independently an integer having a value of 0 to 100; provided that j and x are not simultaneously 0; and provided that u and z are not simultaneously 0; wherein each instance of $X_{aa}$ in $[X_{aa}]_x$ is, independently, a natural or unnatural amino acid residue when x is 1 to 100; and wherein $[X_{aa}]_x$ is hydrogen when x is 0; wherein each instance of $X_{aa}$ in $[X_{aa}]_y$ is, independently, a natural or unnatural amino acid; wherein each instance of $X_{aa}$ in $[X_{aa}]_z$ is, independently, a natural or unnatural amino acid when z is 1 to 100; and wherein $[X_{aa}]_z$ is hydroxy when z is 0; wherein each of $R^{1a}$ and $R^{1b}$ is independently hydrogen or an amino protecting group; wherein each of $R^{2a}$ and $R^{2b}$ is independently hydrogen or C1-C4 alkyl; wherein each of $R^{3a}$ and $R^{3b}$ is independently a C1-C4 alkylene; wherein Z is C5-C12 alkylene, —(C2-C6 alkylene)-O—(C2-C6 alkylene)-, —$(CH_2)_3$—$(OCH_2CH_2)_q$—O—$(CH_2)_3$—, wherein q is 0, 1, 2, 3, or 4; or a moiety represented by a formula:

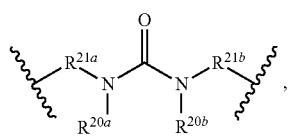

wherein each of $R^{20a}$ and $R^{20b}$ is independently selected from hydrogen and C1-C4 alkyl; and wherein each of $R^{21a}$ and $R^{21b}$ is independently C3-C6 alkylene; or a moiety represented by a formula:

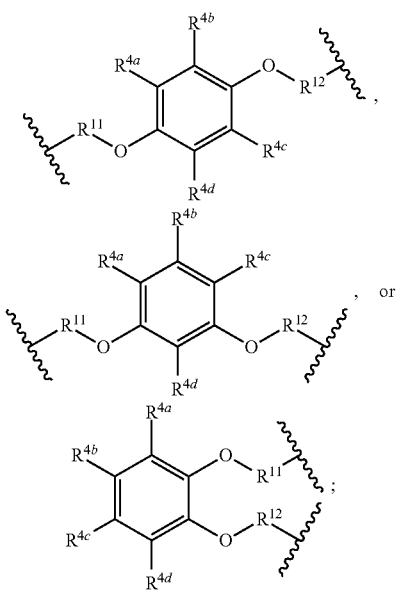

wherein q is 0, 1, 2, 3, or 4; wherein each of $R^{4a}$, $R^{4b}$, $R^{4c}$, and $R^{4d}$ is independently hydrogen, hydroxy, amino, C1-C4 alkyl, and —$CO_2H$; and wherein each of $R^{11}$ and $R^{12}$ is independently C3-C6 alkylene; or a pharmaceutically acceptable salt thereof.

In a further aspect, the invention relates to a peptide having a structure represented by a formula:

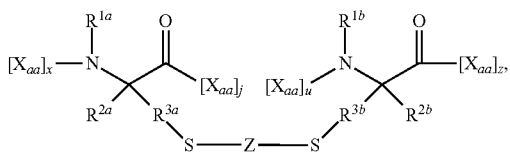

wherein each of j, u, x, and z is independently an integer having a value of 0 to 100; provided that j and x are not simultaneously 0; and provided that u and z are not simultaneously 0; wherein each instance of $X_{aa}$ in $[X_{aa}]_x$ is, independently, a natural or unnatural amino acid residue when x is 1 to 100; and wherein $[X_{aa}]_x$ is hydrogen when x is 0; wherein each instance of $X_{aa}$ in $[X_{aa}]_y$ is, independently, a natural or unnatural amino acid; wherein each instance of $X_{aa}$ in $[X_{aa}]_z$ is, independently, a natural or unnatural amino acid when z is 1 to 100; and wherein $[X_{aa}]_z$ is hydroxy when z is 0; wherein each of $R^{1a}$ and $R^{1b}$ is independently hydrogen or an amino protecting group; wherein each of $R^{2a}$ and $R^{2b}$ is independently hydrogen or C1-C4 alkyl; wherein each of $R^{3a}$ and $R^{3b}$ is independently a C1-C4 alkylene; wherein Z is C5-C12 alkylene, —(C2-C6 alkylene)-O—(C2-C6 alkylene)-, —$(CH_2)_3$—$(OCH_2CH_2)_q$—$O(CH_2)_3$—, or a moiety represented by a formula:

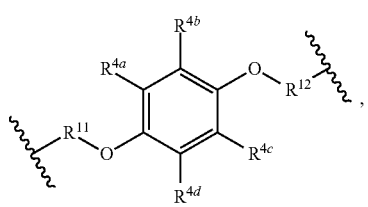

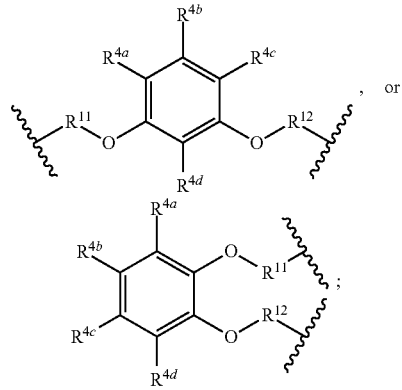

wherein q is 0, 1, 2, 3, or 4; wherein each of $R^{4a}$, $R^{4b}$, $R^{4c}$, and $R^{4d}$ is independently hydrogen, hydroxy, amino, C1-C4 alkyl, and —$CO_2H$; and wherein each of $R^{11}$ and $R^{12}$ is independently C3-C6 alkylene; or a pharmaceutically acceptable salt thereof. In a further aspect, the peptide further comprises acetylation of a carboxy terminal amino acid residue.

In various aspects, each of j, u, x, and z is independently an integer having a value of 0 to 100; provided that j and x are not simultaneously 0; and provided that u and z are not simultaneously 0. In a further aspect, x has the same value as u; and j has the same value as z.

In a further, each of j, u, x, and z is independently an integer having a value of 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100.

In various aspects, each of j, u, x, and z is independently an integer having a value of 0 to 100. In a further aspect, each of j, u, x, and z is independently an integer having a value of 0 to 90. In a still further aspect, each of j, u, x, and z is independently an integer having a value of 0 to 80. In a yet further aspect, each of j, u, x, and z is independently an integer having a value of 0 to 70. In an even further aspect, each of j, u, x, and z is independently an integer having a value of 0 to 60. In a still further aspect, each of j, u, x, and z is independently an integer having a value of 0 to 50. In a yet further aspect, each of j, u, x, and z is independently an integer having a value of 0 to 40. In an even further aspect, each of j, u, x, and z is independently an integer having a value of 0 to 30. In a still further aspect, each of j, u, x, and z is independently an integer having a value of 0 to 20. In a yet further aspect, each of j, u, x, and z is independently an integer having a value of 0 to 10.

In a further aspect, each of j, u, x, and z is independently an integer having a value of 1 to 15. In a still further aspect, each of j, u, x, and z is independently an integer having a value of 2 to 15. In a yet further aspect, each of j, u, x, and z is independently an integer having a value of 3 to 15. In an even further aspect, each of j, u, x, and z is independently an integer having a value of 4 to 15. In a still further aspect, each of j, u, x, and z is independently an integer having a value of 5 to 15. In a yet further aspect, each of j, u, x, and z is independently an integer having a value of 6 to 15. In an even further aspect, each of j, u, x, and z is independently an integer having a value of 7 to 15. In a still further aspect, each of j, u, x, and z is independently an integer having a value of 8 to 15. In a yet further aspect, each of j, u, x, and z is independently an integer having a value of 9 to 15. In an even further aspect, each of j, u, x, and z is independently an integer having a value of 10 to 15.

In various aspects, the invention relates to a peptide prepared by any of the disclosed methods.

In a further aspect, the invention relates to a stapled peptide prepared by a method comprising reacting a bis-terminal diene with a peptide comprising a first amino acid residue with a thiol-containing R group and a second amino acid residue with a thiol-containing R group.

In a further aspect, the invention relates to a stapled peptide prepared by a method comprising reacting a bis-terminal diene with a peptide comprising a first amino acid residue with a thiol-containing R group and a second amino acid residue with a thiol-containing R group, wherein reacting comprises reacting with a radical initiator.

In a further aspect, the invention relates to a stapled peptide prepared by a method comprising reacting a bis-terminal diene with a peptide comprising a first amino acid residue with a thiol-containing R group and a second amino acid residue with a thiol-containing R group, wherein reacting comprises reacting with a photoinitiator.

In a further aspect, the invention relates to a stapled peptide prepared by a method comprising reacting a bis-terminal diene with a peptide comprising a first amino acid residue with a thiol-containing R group and a second amino acid residue with a thiol-containing R group, wherein reacting comprises reacting with 2,2-dimethoxy-2-phenylacetophenone, 9,10-dioxo-9, 10-dihydroanthracene-2-sulfonic acid, or (phenylphosphoryl)bis(mesitylmethanone).

In a further aspect, the invention relates to a stapled peptide prepared by a method comprising reacting a bis-terminal diene with a peptide comprising a first amino acid residue with a thiol-containing R group and a second amino acid residue with a thiol-containing R group; and wherein the peptide is glucagon or a glucagon homologue with two cysteine or homocysteine residues.

In a further aspect, the invention relates to a stapled peptide prepared by a method comprising reacting a bis-terminal diene with a peptide comprising a first amino acid residue with a thiol-containing R group and a second amino acid residue with a thiol-containing R group, wherein the peptide is glucagon or a glucagon homologue with two cysteine or homocysteine residues; and wherein reacting comprises reacting with a radical initiator.

In a further aspect, the invention relates to a stapled peptide prepared by a method comprising reacting a bis-terminal diene with a peptide comprising a first amino acid residue with a thiol-containing R group and a second amino acid residue with a thiol-containing R group, wherein the peptide is glucagon or a glucagon homologue with two cysteine or homocysteine residues; and wherein reacting comprises reacting with a photoinitiator.

In a further aspect, the invention relates to a stapled peptide prepared by a method comprising reacting a bis-terminal diene with a peptide comprising a first amino acid residue with a thiol-containing R group and a second amino acid residue with a thiol-containing R group, wherein the peptide is glucagon or a glucagon homologue with two cysteine or homocysteine residues; and wherein reacting comprises reacting with 2,2-dimethoxy-2-phenylacetophenone, 9,10-dioxo-9,10-dihydroanthracene-2-sulfonic acid, or (phenylphosphoryl)bis(mesitylmethanone).

In a further aspect, the invention relates to a stapled peptide prepared by a method comprising reacting a bis-terminal diene with a peptide comprising a first amino acid residue with a thiol-containing R group and a second amino acid residue with a thiol-containing R group; and wherein the peptide has the sequence:

```
                                    (SEQ ID NO: 1)
HSQGTFTSDYSKYLDSCRAQCFVQWLMNT, (SEQ ID NO: 2)
HSQGTFTSDYSKYLDSRRACDFVCWLMNT, (SEQ ID NO: 3)
HSQGTFTSDYSKYLDSRRACDFVQWLCNT, (SEQ ID NO: 4)
HSQGTFTSDYSKYLDSRRAQCFVQWLMCT,
or (SEQ ID NO: 5)
HSQGTFTSDYSKYLDSRRAQDFVCWLMCT.
```

In a further aspect, the invention relates to a stapled peptide prepared by a method comprising reacting a bis-terminal diene with a peptide comprising a first amino acid residue with a thiol-containing R group and a second amino acid residue with a thiol-containing R group, wherein the peptide has the sequence:

```
                                    (SEQ ID NO: 1)
HSQGTFTSDYSKYLDSCRAQCFVQWLMNT, (SEQ ID NO: 2)
HSQGTFTSDYSKYLDSRRACDFVCWLMNT, (SEQ ID NO: 3)
HSQGTFTSDYSKYLDSRRACDFVQWLCNT, (SEQ ID NO: 4)
HSQGTFTSDYSKYLDSRRAQCFVQWLMCT,
or (SEQ ID NO: 5)
HSQGTFTSDYSKYLDSRRAQDFVCWLMCT.
``` and wherein reacting comprises reacting with a radical initiator.

In a further aspect, the invention relates to a stapled peptide prepared by a method comprising reacting a bis-terminal diene with a peptide comprising a first amino acid residue with a thiol-containing R group and a second amino acid residue with a thiol-containing R group, wherein the peptide has the sequence:

```
                                    (SEQ ID NO: 1)
HSQGTFTSDYSKYLDSCRAQCFVQWLMNT, (SEQ ID NO: 2)
HSQGTFTSDYSKYLDSRRACDFVCWLMNT, (SEQ ID NO: 3)
HSQGTFTSDYSKYLDSRRACDFVQWLCNT, (SEQ ID NO: 4)
HSQGTFTSDYSKYLDSRRAQCFVQWLMCT,
or (SEQ ID NO: 5)
HSQGTFTSDYSKYLDSRRAQDFVCWLMCT.
``` and wherein reacting comprises reacting with a photoinitiator.

In a further aspect, the invention relates to a stapled peptide prepared by a method comprising reacting a bis-terminal diene with a peptide comprising a first amino acid residue with a thiol-containing R group and a second amino acid residue with a thiol-containing R group, wherein the peptide has the sequence:

```
                                        (SEQ ID NO: 1)
HSQGTFTSDYSKYLDSCRAQCFVQWLMNT, (SEQ ID NO: 2)
HSQGTFTSDYSKYLDSRRACDFVCWLMNT, (SEQ ID NO: 3)
HSQGTFTSDYSKYLDSRRACDFVQWLCNT, (SEQ ID NO: 4)
HSQGTFTSDYSKYLDSRRAQCFVQWLMCT,
or
                                        (SEQ ID NO: 5)
HSQGTFTSDYSKYLDSRRAQDFVCWLMCT.
``` and wherein reacting comprises reacting with 2,2-dimethoxy-2-phenylacetophenone. 9,10-dioxo-9,10-dihydroanthracene-2-sulfonic acid, or (phenylphosphoryl)bis(mesitylmethanone).

In one aspect, the invention relates to a stapled peptide prepared by a method comprising the steps of: (a) providing a peptide having the structure represented by the formula:

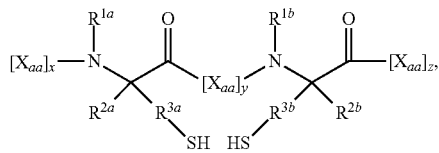

wherein each of x and z is independently an integer having a value of 0 to 100; wherein y is an integer having a value of 1 to 20; wherein each instance of $X_{aa}$ is, independently, a natural or unnatural amino acid; wherein each of $R^{1a}$ and $R^{1b}$ is independently hydrogen or an amino protecting group; wherein each of $R^{2a}$ and $R^{2b}$ is independently hydrogen or C1-C4 alkyl; wherein each of $R^{3a}$ and $R^{3b}$ is independently a C1-C4 alkyl; (b) providing a diene having the structure represented by the formula:

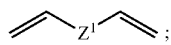

wherein $Z^1$ is C1-C8 alkyl, C3-C8 ether, C6-C8 polyether, or a moiety represented by a formula:

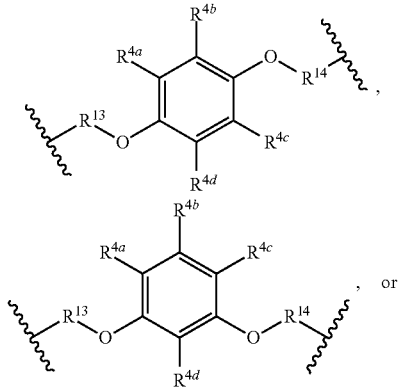

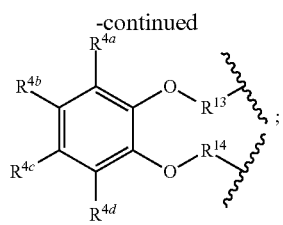

wherein each of $R^{4a}$, $R^{4b}$, $R^{4c}$, and $R^{4d}$ is independently hydrogen, hydroxy, amino, C1-C4 alkyl, and —$CO_2H$; and wherein each of $R^{13}$ and $R^{14}$ is independently C1-C4 alkyl; and (c) reacting the peptide and the diene in the presence of radical initiator; thereby forming the stapled peptide.

In one aspect, the invention relates to a stapled peptide prepared by a method comprising the steps of: (a) providing a peptide having the structure represented by the formula:

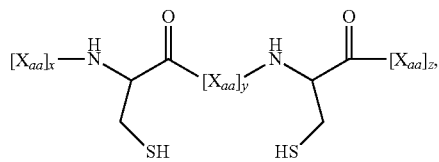

wherein each of x and z is independently an integer having a value of 0 to 100; wherein y is an integer having a value of 1 to 20; wherein each instance of $X_{aa}$ is, independently, a natural or unnatural amino acid; (b) providing a diene having the structure represented by the formula:

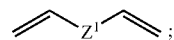

wherein $Z^1$ is C1-C8 alkyl, C3-C8 ether, C6-C8 polyether, or a moiety represented by a formula:

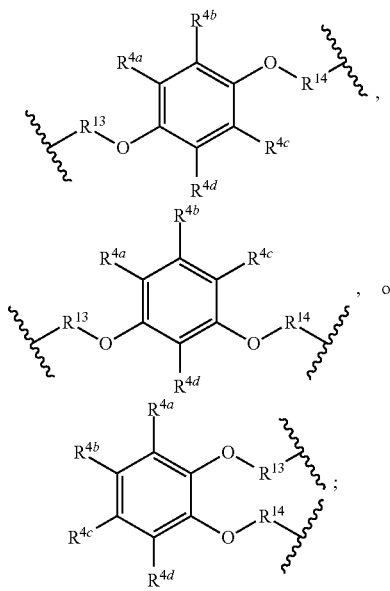

wherein each of $R^{4a}$, $R^{4b}$, $R^4$, and $R^{4d}$ is independently hydrogen, hydroxy, amino, C1-C4 alkyl, and —$CO_2H$; and wherein each of R[13] and R[14] is independently C1-C4 alkyl; and (c) reacting the peptide and the diene in the presence of radical initiator; thereby forming the stapled peptide.

In one aspect, the invention relates to a stapled peptide prepared by a method comprising the steps of: (a) providing a peptide having the structure represented by the formula:

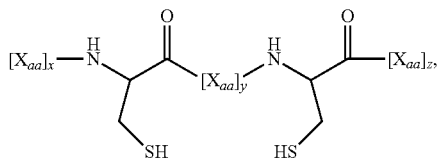

wherein each of x and z is independently an integer having a value of 0 to 100; wherein y is an integer having a value of 1 to 20; wherein each instance of $X_{aa}$ is, independently, a natural or unnatural amino acid; (b) providing a diene having the structure represented by the formula:

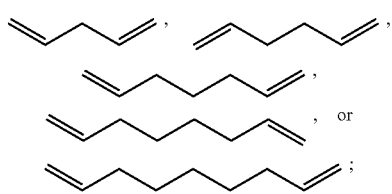

and (c) reacting the peptide and the diene in the presence of radical initiator; thereby forming the stapled peptide.

In one aspect, the invention relates to a stapled peptide prepared by a method comprising the steps of: (a) providing a peptide having the structure represented by the formula:

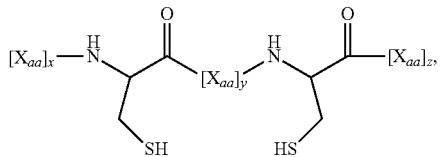

wherein each of x and z is independently an integer having a value of 0 to 100; wherein y is an integer having a value of 1 to 20; wherein each instance of $X_{aa}$ is, independently, a natural or unnatural amino acid; (b) providing a diene having the structure represented by the formula:

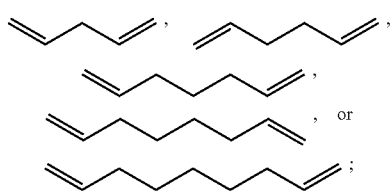

and (c) reacting the peptide and the diene in the presence of 2,2-dimethoxy-2-phenylacetophenone, 9,10-dioxo-9,10-dihydroanthracene-2-sulfonic acid, or (phenylphosphoryl)bis(mesitylmethanone); thereby forming the stapled peptide.

In one aspect, the invention relates to a stapled peptide prepared by a method comprising the steps of: (a) providing a peptide having the structure represented by the formula:

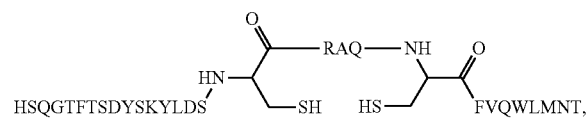

(b) providing a diene having the structure represented by the formula:

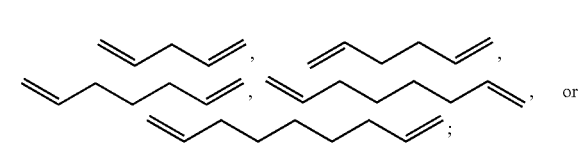

and (c) reacting the peptide and the diene in the presence of 2,2-dimethoxy-2-phenylacetophenone, 9,10-dioxo-9,10-dihydroanthracene-2-sulfonic acid, or (phenylphosphoryl)bis(mesitylmethanone), thereby forming the stapled peptide.

In one aspect, the invention relates to a stapled peptide prepared by a method comprising the steps of: (a) providing a peptide having the structure represented by the formula:

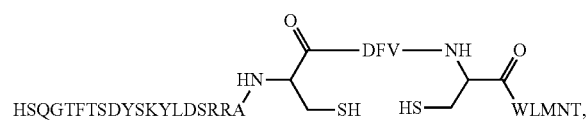

(b) providing a diene having the structure represented by the formula:

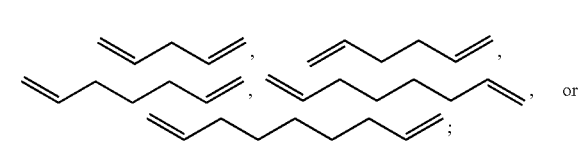

and (c) reacting the peptide and the diene in the presence of 2,2-dimethoxy-2-phenylacetophenone, 9,10-dioxo-9,10-dihydroanthracene-2-sulfonic acid, or (phenylphosphoryl)bis(mesitylmethanone); thereby forming the stapled peptide.

In one aspect, the invention relates to a stapled peptide prepared by a method comprising the steps of: (a) providing a peptide having the structure represented by the formula:

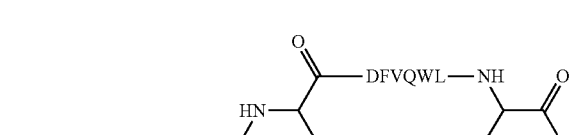

(b) providing a diene having the structure represented by the formula:

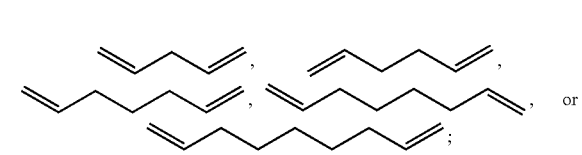

and (c) reacting the peptide and the diene in the presence of 2,2-dimethoxy-2-phenylacetophenone, 9,10-dioxo-9,10-dihydroanthracene-2-sulfonic acid, or (phenylphosphoryl)bis(mesitylmethanone); thereby forming the stapled peptide.

In one aspect, the invention relates to a stapled peptide prepared by a method comprising the steps of: (a) providing a peptide having the structure represented by the formula:

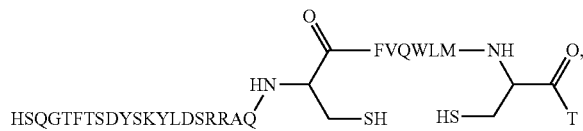

(b) providing a diene having the structure represented by the formula:

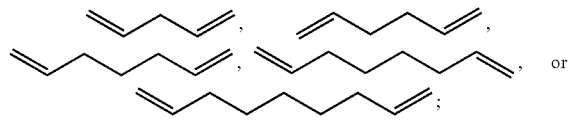

and (c) reacting the peptide and the diene in the presence of 2,2-dimethoxy-2-phenylacetophenone, 9,10-dioxo-9,10-dihydroanthracene-2-sulfonic acid, or (phenylphosphoryl)bis(mesitylmethanone); thereby forming the stapled peptide.

In one aspect, the invention relates to a stapled peptide prepared by a method comprising the steps of: (a) providing a peptide having the structure represented by the formula:

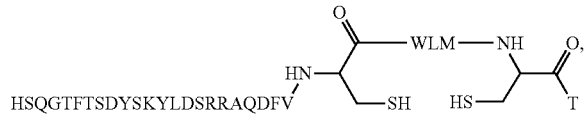

(b) providing a diene having the structure represented by the formula:

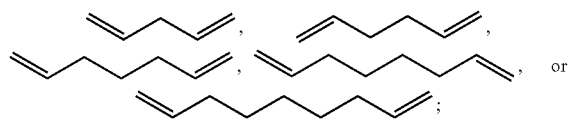

and (c) reacting the peptide and the diene in the presence of 2,2-dimethoxy-2-phenylacetophenone, 9,10-dioxo-9,10-dihydroanthracene-2-sulfonic acid, or (phenylphosphoryl)bis(mesitylmethanone); thereby forming the stapled peptide.

a. $[X_{aa}]_x$ Groups

In various aspects, each instance of $X_{aa}$ in $[X]_x$ is, independently, a natural or unnatural amino acid residue when x is 1 to 100; and $[X_{aa}]_x$ is hydrogen when x is 0.

In a further aspect, x is not 0, and each instance of $X_{aa}$ in $[X_{aa}]_x$ is, independently, a natural or unnatural amino acid residue.

In a further aspect, x is 0 and $[X_{aa}]_x$ is hydrogen.

In various aspects, each instance of $X_{aa}$ in $[X_{aa}]_x$ is, independently, a natural amino acid residue when x is 1 to 100; and $[X_{aa}]_x$ is hydrogen when x is 0.

In a further aspect, x is not 0, and each instance of $X_{aa}$ in $[X_{aa}]_x$ is, independently, a natural amino acid residue.

b. $[X_{aa}]_y$ Groups

In various aspects, each instance of $X_{aa}$ in $[X_{aa}]_y$ is, independently, a natural or unnatural amino acid.

In a further aspect, each instance of $X_{aa}$ in $[X]_y$ is, independently, a natural amino acid.

c. $[X_{aa}]_z$ Groups

In various aspects, each instance of $X_{aa}$ in $[X_{aa}]_z$ is, independently, a natural or unnatural amino acid when z is 1 to 100; and wherein $[X_{aa}]_z$ is hydroxy when z is 0.

In a further aspect, z is not 0, and each instance of $X_{aa}$ in $[X_{aa}]_z$ is, independently, a natural or unnatural amino acid residue.

In a further aspect, z is 0 and $[X_{aa}]_z$ is hydroxy.

In various aspects, each instance of $X_{aa}$ in $[X_{aa}]_z$ is, independently, a natural amino acid residue when z is 1 to 100; and $[X_{aa}]_z$ is hydrogen when x is 0.

In a further aspect, z is not 0, and each instance of $X_{aa}$ in $[X_{aa}]_z$ is, independently, a natural amino acid residue.

d. $R^{1a}$ and $R^{1b}$ Groups

In one aspect, each of $R^{1a}$ and $R^{1b}$ is independently hydrogen or an amino protecting group. In a further aspect, each of $R^{1a}$ and $R^{1b}$ is hydrogen.

In a further aspect, each of $R^{1a}$ and $R^{1b}$ is an amino protecting group. In a still further aspect, each of $R^{1a}$ and $R^{1b}$ is an amino protecting group, and the amino protecting group is a Fmoc protecting group. In a yet further aspect, each of $R^{1a}$ and $R^{1b}$ is an amino protecting group, and the amino protecting group is a Boc protecting group.

e. $R^{2a}$ and $R^{2b}$ Groups

In one aspect, each of $R^{2a}$ and $R^{2b}$ is independently hydrogen or C1-C4 alkyl. In a further aspect, each of $R^{2a}$ and $R^{2b}$ is hydrogen. In a still further aspect, each of $R^{2a}$ and $R^{2b}$ is methyl.

In a further aspect, each of $R^{2a}$ and $R^{2b}$ is independently hydrogen, methyl, ethyl, propyl, or isopropyl. In a still further aspect, each of $R^{2a}$ and $R^{2b}$ is independently hydrogen, methyl, or ethyl. In a yet further aspect, each of $R^{2a}$ and $R^{2b}$ is independently hydrogen or methyl. In an even further aspect, each of $R^{2a}$ and $R^{2b}$ is independently hydrogen or ethyl. In a still further aspect, each of $R^{2a}$ and $R^{2b}$ is independently hydrogen, propyl, or isopropyl.

f. $R^{3a}$ and $R^{3b}$ Groups

In one aspect, each of $R^{3a}$ and $R^{3b}$ is independently a C1-C4 alkylene.

In a further aspect, wherein each of $R^{3a}$ and $R^{3b}$ is independently —$CH_2$— or —$(CH_2)_2$—. In a still further aspect, each of $R^{3a}$ and $R^{3b}$ is —$CH_2$—. In a yet further aspect, each of $R^{3a}$ and $R^{3b}$ is —$(CH_2)_2$—.

g. $R^{4a}$, $R^{4b}$, $R^{4c}$, and $R^{4d}$ Groups

In one aspect, each of $R^{4a}$, $R^{4b}$, $R^{4c}$, and $R^{4d}$ is independently hydrogen, hydroxy, amino, C1-C4 alkyl, and —$CO_2H$. In a further aspect, each of $R^{4a}$, $R^{4b}$, $R^{4c}$, and $R^{4d}$ is hydrogen.

In a further aspect, each of $R^{4a}$, $R^{4b}$, $R^{4c}$, and $R^{4d}$ is hydrogen, hydroxy, amino, or C1-C4 alkyl. In a still further aspect, each of $R^{4a}$, $R^{4b}$, $R^{4c}$, and $R^{4d}$ is hydrogen, hydroxy, amino, methyl, ethyl, propyl, or isopropyl. In a yet further aspect, each of $R^{4a}$, $R^{4b}$, $R^{4c}$, and $R^{4d}$ is hydrogen, hydroxy, amino, methyl, or ethyl. In an even further aspect, In a still further aspect, each of $R^4$, $R^{4b}$, $R^{4c}$, and $R^{4d}$ is hydrogen, hydroxy, amino, or methyl.

In a further aspect, each of $R^{4a}$, $R^{4b}$, $R^{4c}$, and $R^{4d}$ is hydrogen or C1-C4 alkyl. In a still further aspect, each of $R^{4a}$, $R^{4b}$, $R^{4c}$, and $R^{4d}$ is hydrogen, methyl, ethyl, propyl, or isopropyl. In a yet further aspect, each of $R^{4a}$, $R^{4b}$, $R^{4c}$, and $R^{4d}$ is hydrogen, methyl, or ethyl. In an even further aspect, In a still further aspect, each of $R^{4a}$, $R^{4b}$, $R^{4c}$, and $R^{4d}$ is hydrogen or methyl.

In a further aspect, each of $R^{4a}$, $R^{4b}$, $R^{4c}$, and $R^{4d}$ is hydrogen, hydroxy, or amino. In a still further aspect, each of $R^{4a}$, $R^{4b}$, and $R^{4c}$ is hydrogen, and $R^{4d}$ is hydroxy or amino. In a yet further aspect, each of $R^{4a}$, $R^{4b}$, and $R^{4d}$ is hydrogen, and $R^{4c}$ is hydroxy or amino. In an even further aspect, each of $R^{4a}$, $R^{4c}$, and $R^{4d}$ is hydrogen, and $R^{4b}$ is hydroxy or amino. In a still further aspect, each of $R^{4b}$, $R^{4c}$, and $R^{4d}$ is hydrogen, and $R^{4a}$ is hydroxy or amino.

In a further aspect, a still further aspect, each of $R^{4a}$, $R^{4b}$, and $R^{4c}$ is hydrogen, and $R^{4d}$ is $-CO_2H$. In a yet further aspect, each of $R^{4a}$, $R^{4b}$, and $R^{4d}$ is hydrogen, and $R^{4c}$ is $-CO_2H$ o. In an even further aspect, each of $R^{4a}$, $R^{4c}$, and $R^{4d}$ is hydrogen, and $R^{4b}$ is $-CO_2H$. In a still further aspect, each of $R^{4b}$, $R^{4c}$, and $R^{4d}$ is hydrogen, and $R^{4a}$ is $-CO_2H$.

h. $R^{11}$ and $R^{12}$ Groups

In one aspect, each of $R^{11}$ and $R^{12}$ is independently C3-C6 alkylene.

In a further aspect, wherein each of $R^{11}$ and $R^{12}$ is independently $-(CH_2)_3-$, $-(CH_2)_4-$, or $-(CH_2)_5-$. In a still further aspect, each of $R^{11}$ and $R^{12}$ is $-(CH_2)_3-$. In a still further aspect, each of $R^{11}$ and $R^{12}$ is $-(CH_2)_4-$. In a still further aspect, each of $R^{11}$ and $R^{12}$ is $-(CH_2)_5-$. In a still further aspect, each of $R^{11}$ and $R^{12}$ is $-(CH_2)_6-$.

i. Z Groups

In one aspect, Z is C5-C12 alkylene, $-(C2-C6\ alkylene)-O-(C2-C6\ alkylene)-$, $-(CH_2)_3-(OCH_2CH_2)_q-O-(CH_2)_3-$, or a moiety represented by a formula:

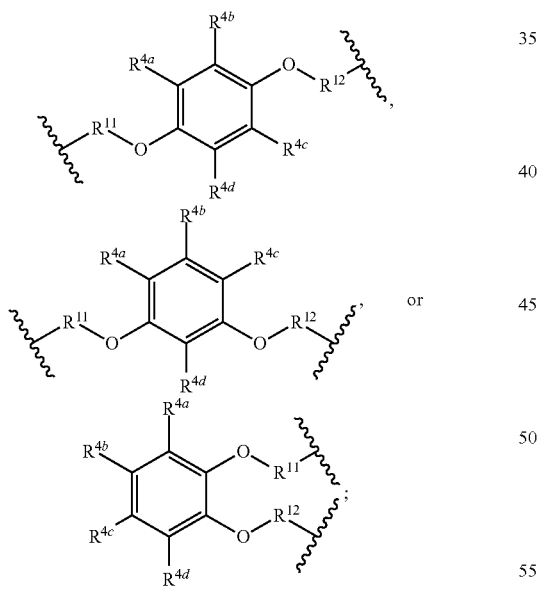

In a further aspect, Z is a moiety represented by a formula:

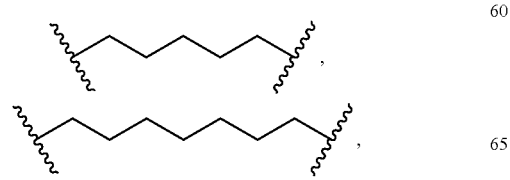

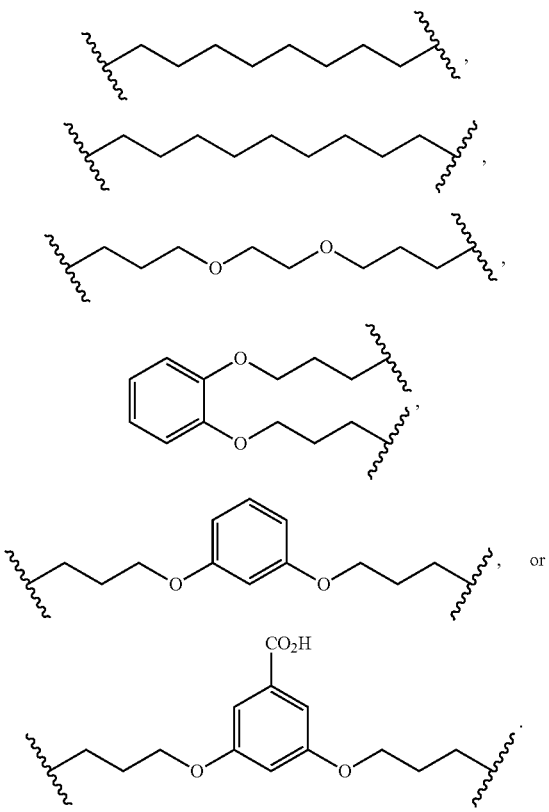

In a further aspect, Z is a moiety represented by a formula:

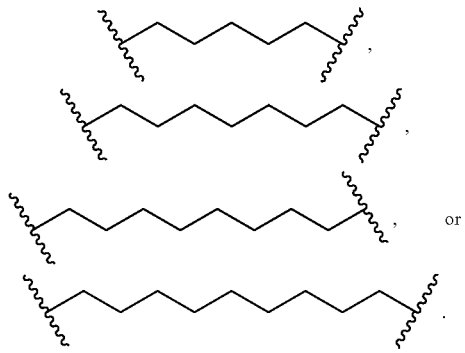

In a further aspect, Z is a moiety represented by a formula:

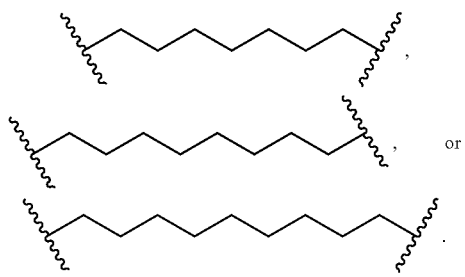

In a further aspect, Z is a moiety represented by a formula:

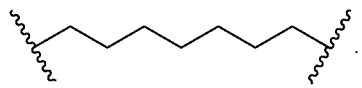 [SMILES: *CCCCCCC*]

In a further aspect, Z is a moiety represented by a formula:

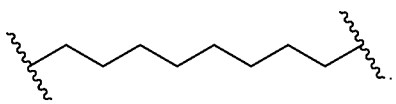 [SMILES: *CCCCCCCC*]

In a further aspect, Z is a moiety represented by a formula:

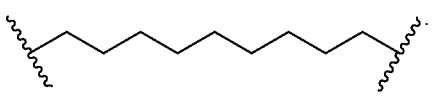 [SMILES: *CCCCCCCCC*]

In a further aspect, Z is a moiety represented by a formula:

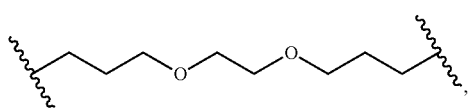 [SMILES: *CCCOCCOCCC*]

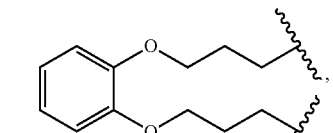

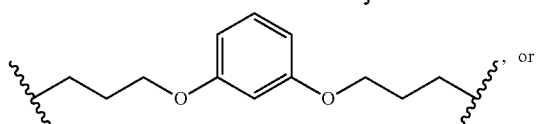

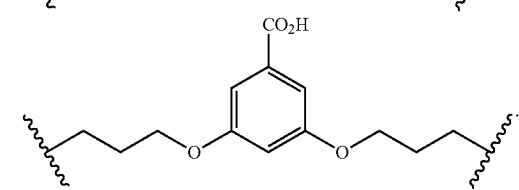

In a further aspect, Z is a moiety represented by a formula:

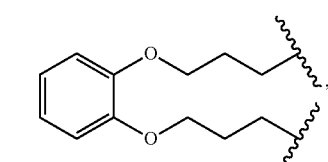

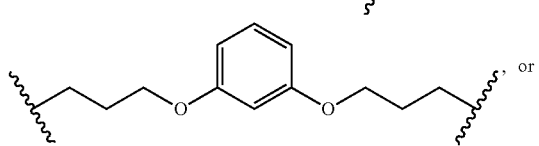

In a further aspect, Z is a moiety represented by a formula:

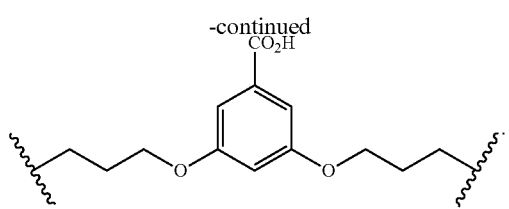

In a further aspect, Z is a moiety represented by a formula:

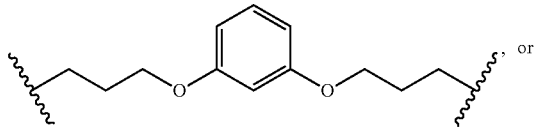, or

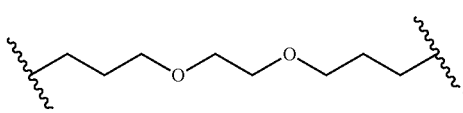

In a further aspect, Z is a moiety represented by a formula:

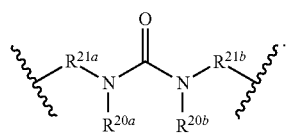

In a further aspect, Z is a moiety represented by a formula:

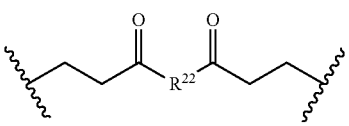

In a further aspect, the linker can be a residue of a bifunctional Michel Acceptor. For example, Z can be a moiety represented by a formula:

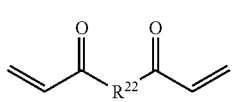

wherein $R^{22}$ is an alkylene moiety having from 1 to 12 carbons, e.g., C1-C8, C1-C6, C1-C4, or C1-C2.

As would be appreciated by those of skill, a bifunctional Michael Acceptor can have a structure, e.g., represented by a formula:

wherein $R^{22}$ is an alkylene moiety having from 1 to 12 carbons, e.g., C1-C8, C1-C6, C1-C4, or C1-C2.

j. $R^{20}$ Groups

In one aspect, each of $R^{20a}$ and $R^{20b}$ is independently selected from hydrogen and C1-C4 alkyl (e.g., methyl, ethyl, propyl, or butyl). For example, $R^{20a}$ can be hydrogen. As a further example, $R^{20a}$ can be C1-C4 alkyl, C1-C3 alkyl, C1-C2 alkyl, methyl, ethyl, propyl, or butyl. For example, $R^{20b}$ can be hydrogen. As a further example, $R^{20b}$ can be C1-C4 alkyl, C1-C3 alkyl, C1-C2 alkyl, methyl, ethyl, propyl, or butyl.

k. $R^{21}$ Groups

In one aspect, each of $R^{21a}$ and $R^{21b}$ is independently C3-C6 alkylene (e.g., methylene, ethylene, or propylene). For example, $R^{21a}$ can be methylene, ethylene, or propylene. For example, $R^{21b}$ can be methylene, ethylene, or propylene.

2. Example Peptides

In one aspect, a peptide can be present as:

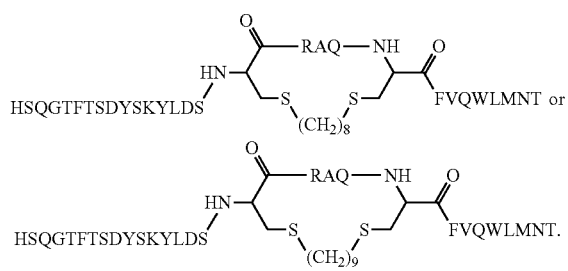

In one aspect, a peptide can be present as:

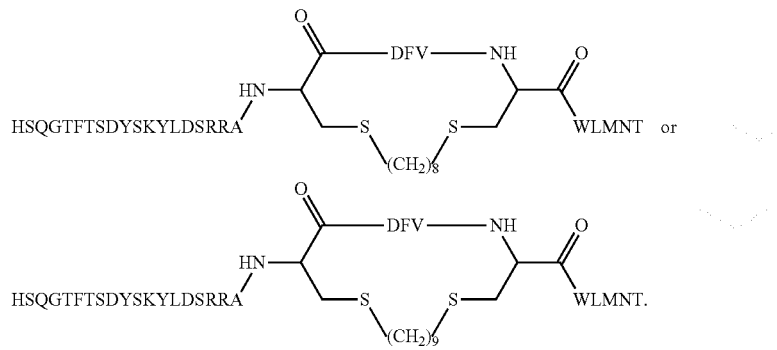

In one aspect, a peptide can be present as:

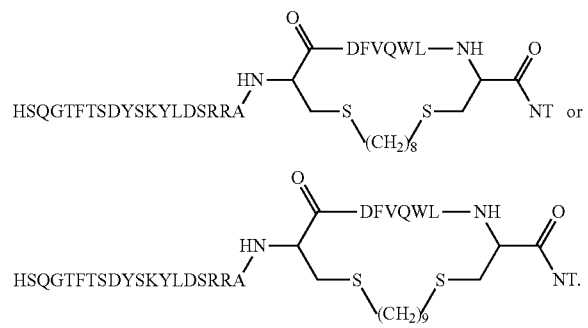

In one aspect, a peptide can be present as:

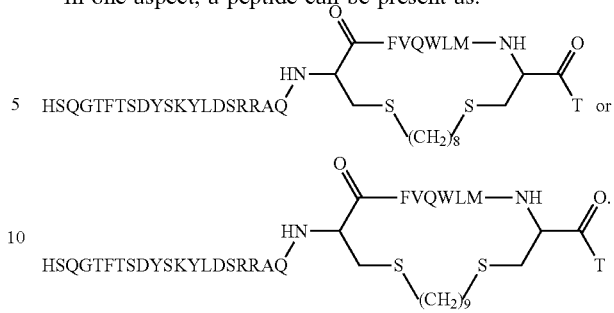

In one aspect, a peptide can be present as:

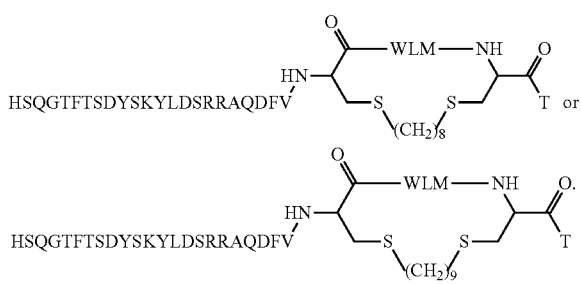

C. Methods of Making the Peptides

In one aspect, the invention relates to methods of making stapled peptides, which can be useful in the treatment of a disease or disorder that requires a therapeutic agent comprising a peptide.

The peptides of this invention can be prepared by employing reactions as shown in the following schemes, in addition to other standard manipulations that are known in the literature, exemplified in the experimental sections or clear to one skilled in the art. For clarity, examples having a single substituent are shown where multiple substituents are allowed under the definitions disclosed herein.

Reactions used to generate the peptides of this invention are prepared by employing reactions as shown in the following Reaction Schemes, in addition to other standard manipulations known in the literature or to one skilled in the art. The following examples are provided so that the invention might be more fully understood, are illustrative only, and should not be construed as limiting.

In various aspects, the invention relates to methods of stapling a peptide having two thiol functionalities with a linker having two alkene functionalities, the method comprising the step of reacting the two thiol functionalities with the two alkene functionalities. In a further aspect, the two thiol functionalities are contained in two cysteine residues in the peptide. In a further aspect, the peptide contains all natural residues. In a further aspect, the reaction is a free-radical reaction. In a further aspect, the reaction is a Michael addition. In a further aspect, the method further comprises a second reaction between two further thiol functionalities in the peptide and two further alkene functionalities in a further linker.

In various aspects, the invention relates to methods of preparing a stapled peptide, the method comprising reacting a bis-terminal diene with a peptide comprising a first amino acid residue with a thiol-containing R group and a second amino acid residue with a thiol-containing R group.

In a further aspect, the reacting further comprises reacting with a radical initiator. In a still further aspect, the radical initiator is a photoinitiator. In a yet further aspect, the photoinitiator is 2,2-dimethoxy-2-phenylacetophenone, 9,10-dioxo-9,10-dihydroanthracene-2-sulfonic acid, or (phenylphosphoryl)bis(mesitylmethanone). In an even further aspect, the photoinitiator is 2,2-dimethoxy-2-phenylacetophenone. In a still further aspect, the photoinitiator is 9,10-dioxo-9,10-dihydroanthracene-2-sulfonic acid. In an even further aspect, the photoinitiator is (phenylphosphoryl) bis(mesitylmethanone).

In a further aspect, the peptide has the sequence:

```
                                          (SEQ ID NO: 1)
HSQGTFTSDYSKYLDSCRAQCFVQWLMNT, (SEQ ID NO: 2)
HSQGTFTSDYSKYLDSRRACDFVCWLMNT, (SEQ ID NO: 3)
HSQGTFTSDYSKYLDSRRACDFVQWLCNT, (SEQ ID NO: 4)
HSQGTFTSDYSKYLDSRRAQCFVQWLMCT,
or (SEQ ID NO: 5)
HSQGTFTSDYSKYLDSRRAQDFVCWLMCT.
```

In one aspect, the disclosed peptides comprise the products of the synthetic methods described herein. In a further aspect, the disclosed peptides comprise a peptide produced by a synthetic method described herein. In a still further aspect, the invention comprises a pharmaceutical composition comprising a therapeutically effective amount of the product of the disclosed methods and a pharmaceutically acceptable carrier. In a still further aspect, the invention comprises a method for manufacturing a medicament comprising combining at least one peptide of any of disclosed peptides or at least one product of the disclosed methods with a pharmaceutically acceptable carrier or diluent.

In one aspect, the invention relates to a method of preparing a stapled peptide, the method comprising the steps of: providing a peptide having the structure represented by the formula:

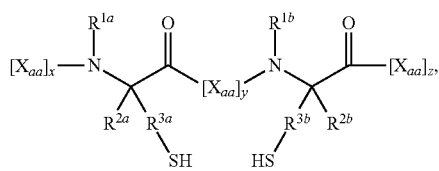

wherein each of x and z is independently an integer having a value of 0 to 100; wherein y is an integer having a value of 1 to 20; wherein each instance of $X_{aa}$ is, independently, a natural or unnatural amino acid; wherein each of $R^{1a}$ and $R^{1b}$ is independently hydrogen or an amino protecting group; wherein each of $R^{2a}$ and $R^{2b}$ is independently hydrogen or C1-C4 alkyl; wherein each of $R^{3a}$ and $R^{3b}$ is independently a C1-C4 alkyl; providing a diene having the structure represented by the formula:

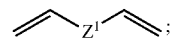

wherein $Z^1$ is C1-C8 alkyl, C3-C8 ether, C6-C8 polyether, or a moiety represented by a formula:

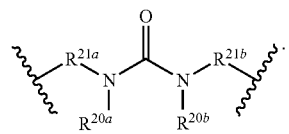

wherein each of $R^{20a}$ and $R^{20b}$ is independently selected from hydrogen and C1-C4 alkyl; and wherein each of $R^{21a}$ and $R^{21b}$ is independently C3-C6 alkylene; or a moiety represented by a formula:

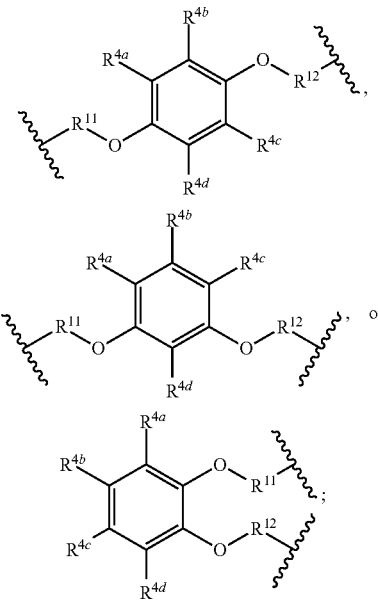

wherein each of $R^{4a}$, $R^{4b}$, $R^{4c}$, and $R^{4d}$ is independently hydrogen, hydroxy, amino, C1-C4 alkyl, and —CO$_2$H; and wherein each of $R^{13}$ and $R^{14}$ is independently C1-C4 alkyl; reacting the peptide and the diene in the presence of radical initiator; thereby forming the stapled peptide.

In one aspect, the invention relates to methods of preparing a stapled peptide, the method comprising the steps of: (a) providing a peptide having the structure represented by the formula:

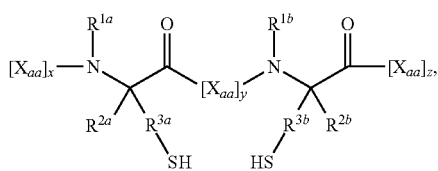

wherein each of x and z is independently an integer having a value of 0 to 100; wherein y is an integer having a value of 1 to 20; wherein each instance of $X_{aa}$ is, independently, a natural or unnatural amino acid; wherein each of $R^{1a}$ and $R^{1b}$ is independently hydrogen or an amino protecting group; wherein each of $R^{2a}$ and $R^{2b}$ is independently hydrogen or C1-C4 alkyl; wherein each of $R^{3a}$ and $R^{3b}$ is independently a C1-C4 alkyl; (b) providing a diene having the structure represented by the formula:

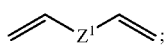

wherein $Z^1$ is C1-C8 alkyl, C3-C8 ether, C6-C8 polyether, or a moiety represented by a formula:

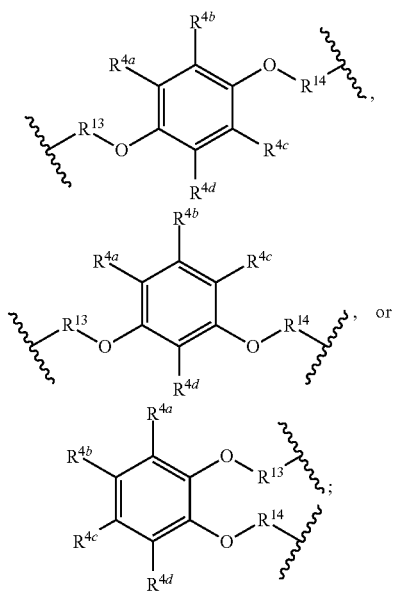

wherein each of $R^{4a}$, $R^{4b}$, $R^{4c}$, and $R^{4d}$ is independently hydrogen, hydroxy, amino, C1-C4 alkyl, and —$CO_2H$; and wherein each of $R^{13}$ and $R^{14}$ is independently C1-C4 alkyl; and (c) reacting the peptide and the diene in the presence of radical initiator; thereby forming the stapled peptide.

In a further aspect, the bis-terminal diene is a compound having a structure represented by the formula:

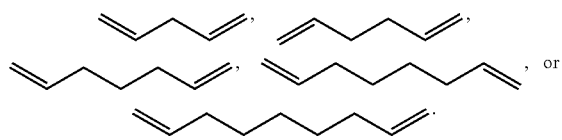

In a further aspect, the radical initiator is a photoinitiator. In a still further aspect, the photoinitiator is 2,2-dimethoxy-2-phenylacetophenone, 9,10-dioxo-9,10-dihydroanthracene-2-sulfonic acid, or (phenylphosphoryl)bis(mesitylmethanone).

In a further aspect, the method further comprises acetylation of a carboxy terminal amino acid residue.

In a further aspect, the peptide having a structure represented by a formula:

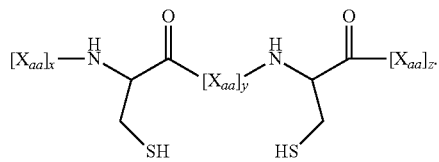

In a further aspect, the peptide having a structure represented by a formula:

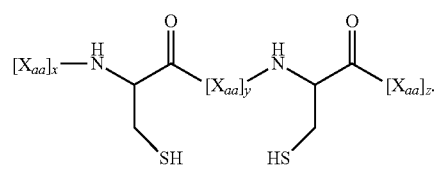

In a further aspect, the peptide having a structure represented by a formula:

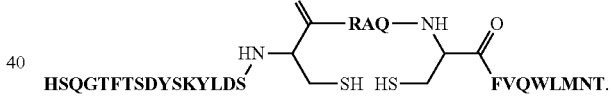

In a further aspect, the peptide having a structure represented by a formula:

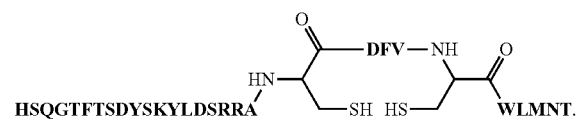

In a further aspect, the peptide having a structure represented by a formula:

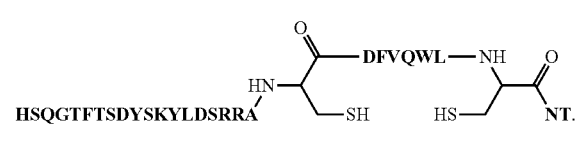

In a further aspect, the peptide having a structure represented by a formula:

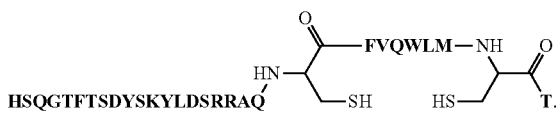

In a further aspect, the peptide having a structure represented by a formula:

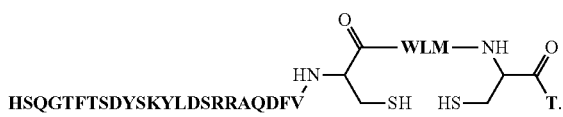

In one aspect, the invention relates to a method of preparing a stapled peptide, the method comprising the steps of: providing a first peptide and a second peptide having, respectively, the structure represented by the formulas:

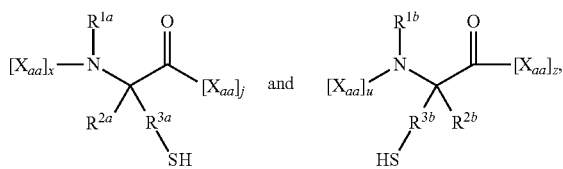

wherein each of j, u, x, and z is independently an integer having a value of 0 to 100; provided that j and x are not simultaneously 0; and provided that u and z are not simultaneously 0; wherein each instance of $X_{aa}$ is, independently, a natural or unnatural amino acid; wherein each of $R^{1a}$ and $R^{1b}$ is independently hydrogen or an amino protecting group; wherein each of $R^{2a}$ and $R^{2b}$ is independently hydrogen or C1-C4 alkyl; wherein each of $R^{3a}$ and $R^{3b}$ is independently a C1-C4 alkyl; providing a diene having the structure represented by the formula:

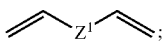

wherein $Z^1$ is C1-C8 alkyl, C3-C8 ether. C6-C8 polyether, or a moiety represented by a formula:

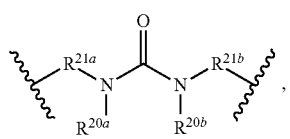

wherein each of $R^{20a}$ and $R^{20b}$ is independently selected from hydrogen and C1-C4 alkyl; and wherein each of $R^{21a}$ and $R^{21b}$ is independently C3-C6 alkylene; or a moiety represented by a formula:

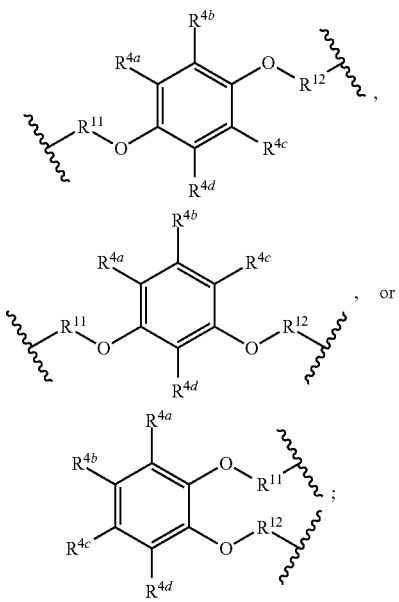

wherein each of $R^{4a}$, $R^{4b}$, $R^{4c}$, and $R^{4d}$ is independently hydrogen, hydroxy, amino, C1-C4 alkyl, and —CO$_2$H; and wherein each of $R^{13}$ and $R^{14}$ is independently C1-C4 alkyl; reacting the peptide and the diene in the presence of radical initiator; thereby forming the stapled peptide.

In various further aspects, the invention relates to methods of preparing a stapled peptide, the method comprising the steps of: (a) providing a first peptide and a second peptide having, respectively, the structure represented by the formulas:

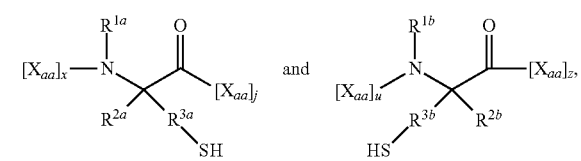

wherein each of j, u, x, and z is independently an integer having a value of 0 to 100; provided that j and x are not simultaneously 0; and provided that u and z are not simultaneously 0; wherein each instance of $X_{aa}$ is, independently, a natural or unnatural amino acid; wherein each of $R^{1a}$ and $R^{1b}$ is independently hydrogen or an amino protecting group; wherein each of $R^{2a}$ and $R^{2b}$ is independently hydrogen or C1-C4 alkyl; wherein each of $R^{3a}$ and $R^{3b}$ is independently a C1-C4 alkyl; (b) providing a diene having the structure represented by the formula:

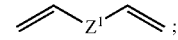

wherein $Z^1$ is C1-C8 alkyl, C3-C8 ether, C6-C8 polyether, or a moiety represented by a formula:

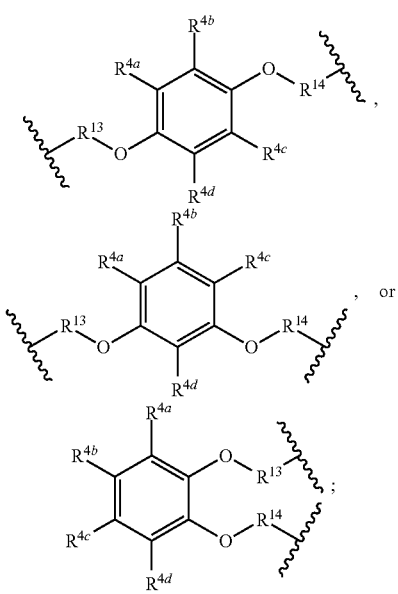

wherein each of $R^{4a}$, $R^{4b}$, $R^{4c}$, and $R^{4d}$ is independently hydrogen, hydroxy, amino, C1-C4 alkyl, and —$CO_2H$; and wherein each of $R^{13}$ and $R^{14}$ is independently C1-C4 alkyl; and (c) reacting the peptide and the diene in the presence of radical initiator; thereby forming the stapled peptide.

Figure 11:
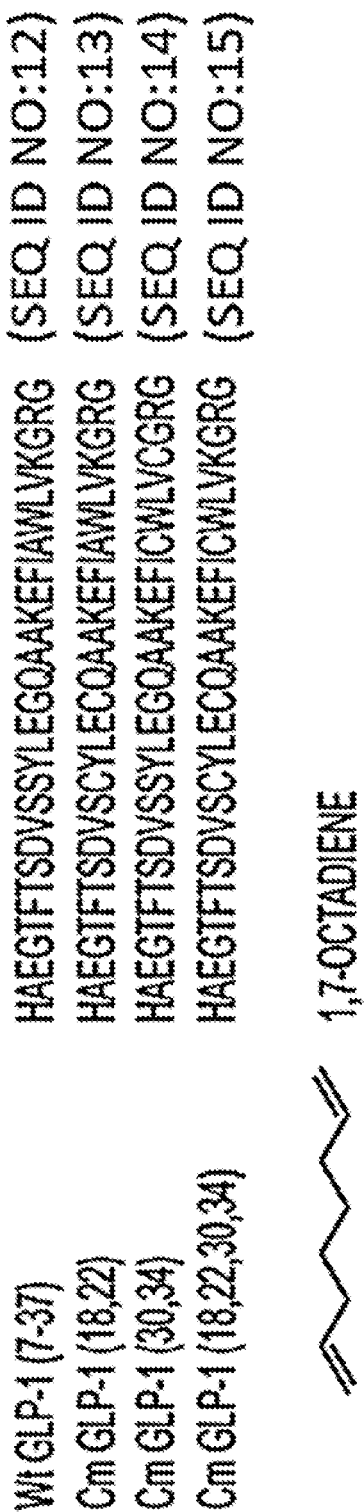
FIG. 11 shows stapling natural biological active peptide (GLP-1).
Figure 12:
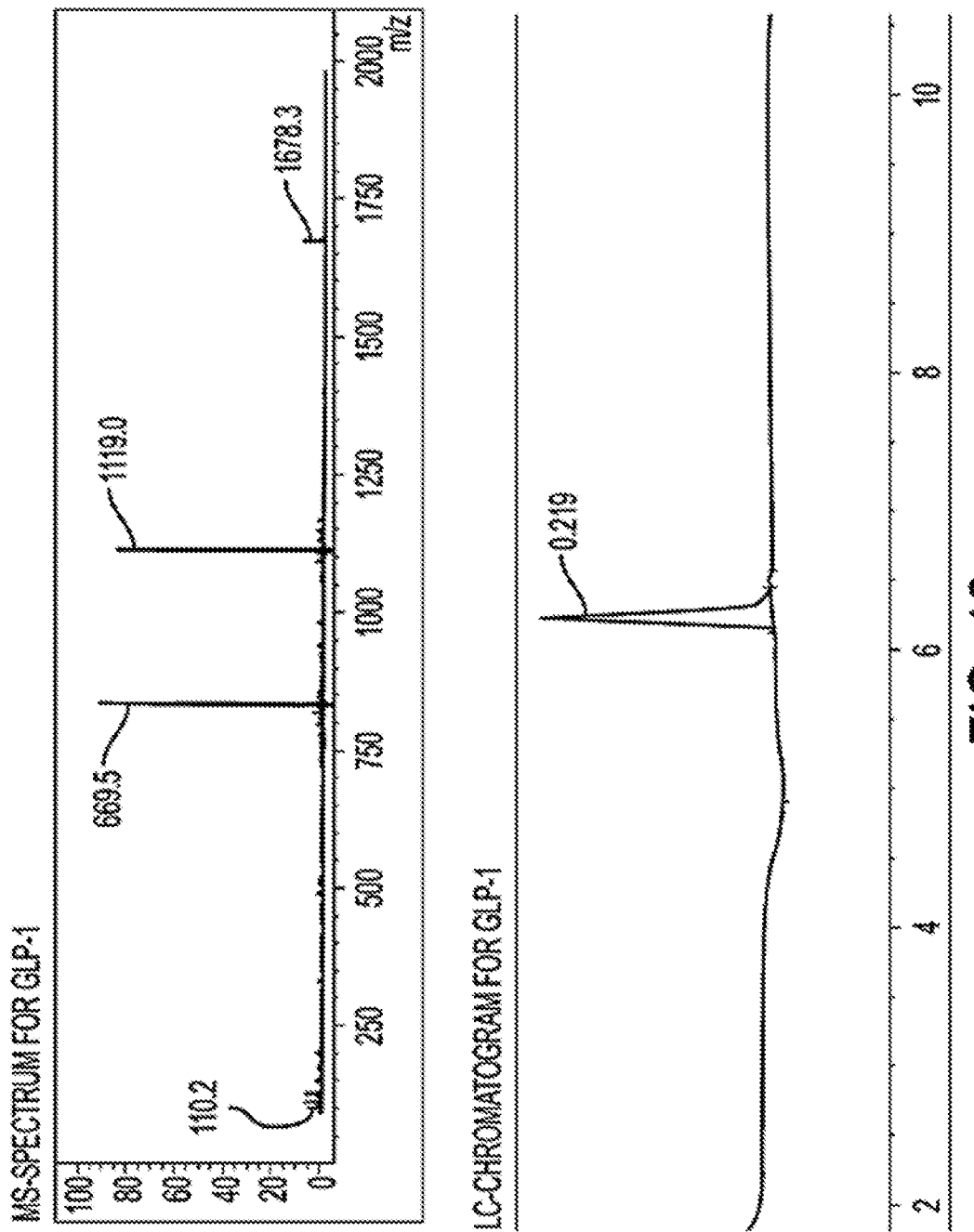
FIG. 12 shows characterization data for GLP-1.
Figure 13:
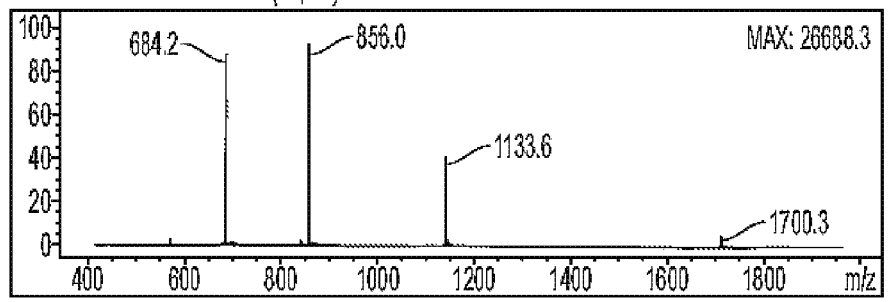
FIG. 13 shows characterization data for GLP-1 (18, 22).
Figure 13:
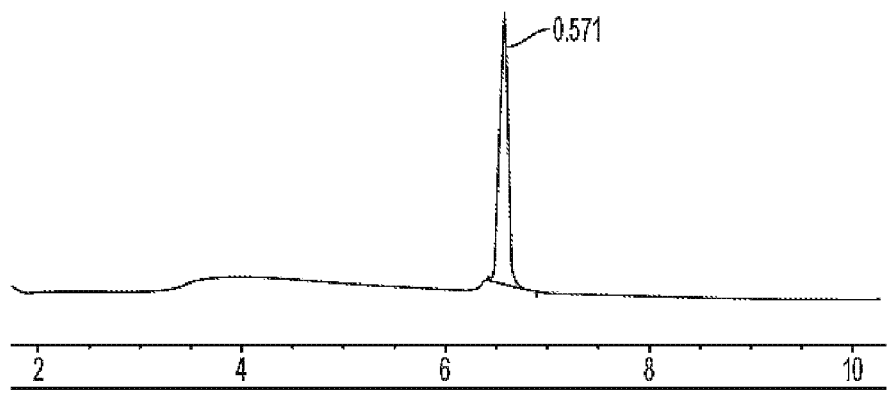
Figure 13:
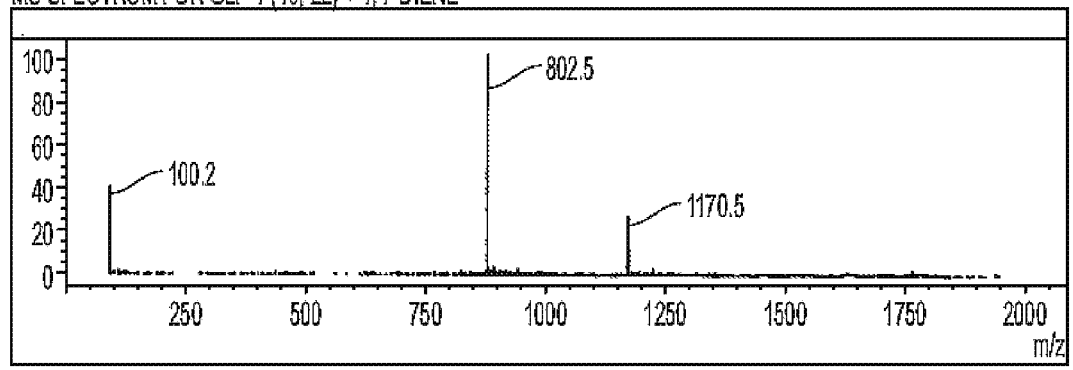
Figure 14:
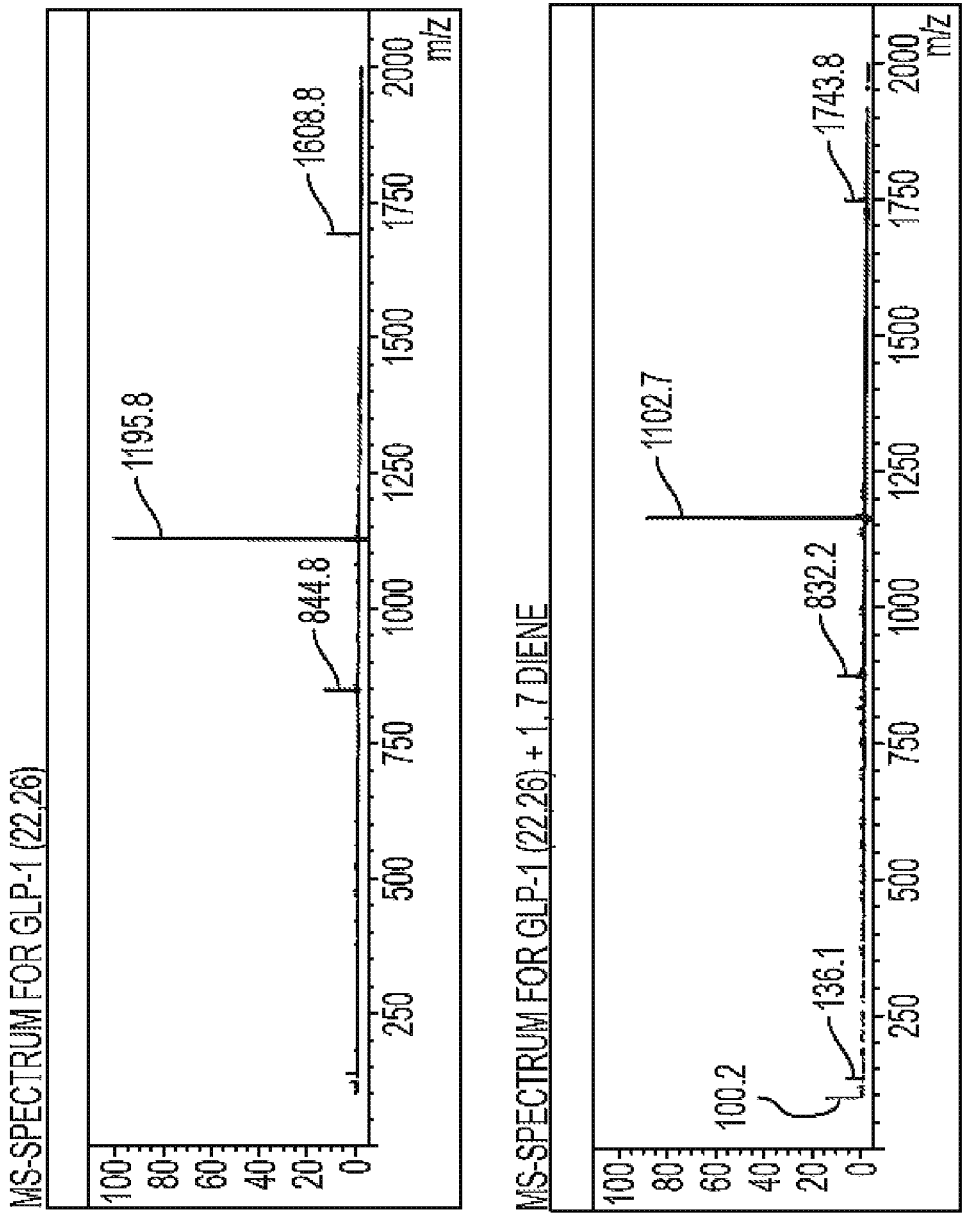
FIG. 14 shows characterization data for GLP-1 (22, 26).
Figure 15:
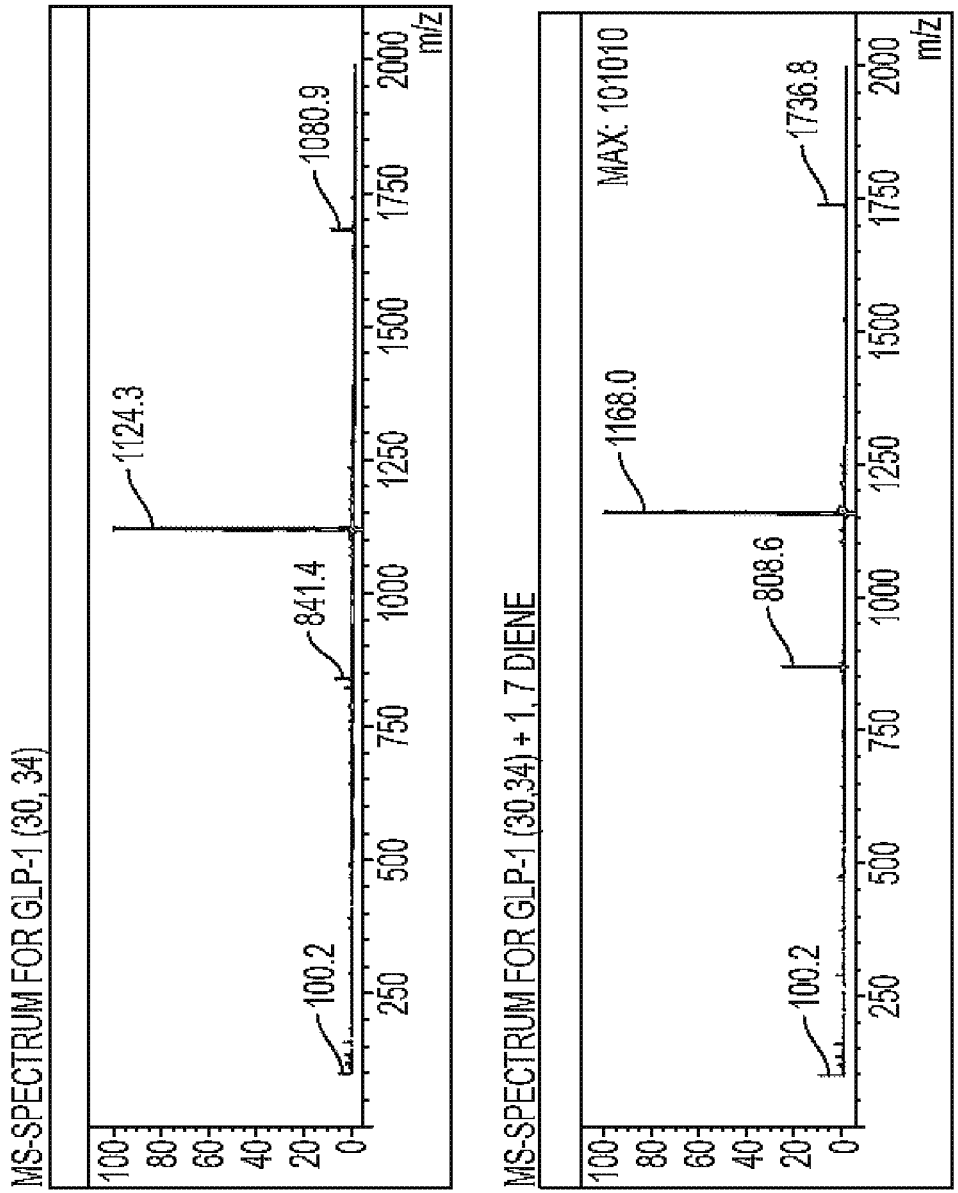
FIG. 15 shows characterization data for GLP-1 (30, 34).

In a further aspect, the disclosed methods (based on thiol-ene reaction) can be used to staple natural biological active peptide (e.g., GLP-1), as shown in FIG. 11. Characterization data for GLP-1 is shown in FIG. 12. For example, GLP-1 can be stapled at residues 18 and 22; characterization data for GLP-1 (18, 22) is shown in FIG. 13. As a further example, GLP-1 can be stapled at residues 22 and 26; characterization data for GLP-1 (22, 26) is shown in FIG. 14. As a further example, GLP-1 can be stapled at residues 30 and 34; characterization data for GLP-1 (30, 34) is shown in FIG. 15.

D. Pharmaceutical Compositions

In one aspect, the invention relates to pharmaceutical compositions comprising the disclosed peptides. That is, a pharmaceutical composition can be provided comprising a therapeutically effective amount of at least one disclosed peptide or at least one product of a disclosed method and a pharmaceutically acceptable carrier.

In certain aspects, the disclosed pharmaceutical compositions comprise the disclosed peptides (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids", includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a peptide of the invention, and/or pharmaceutically acceptable salts thereof, can also be prepared in powder or liquid concentrate form.

In the treatment conditions which require modulation of a therapeutic target by a disclosed peptide, an appropriate dosage level will generally be about 0.01 to 500 mg per kg patient body weight per day and can be administered in single or multiple doses. Preferably, the dosage level will be about 0.1 to about 250 mg/kg per day; more preferably 0.5 to 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the form of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900 and 1000 milligrams of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response.

It is understood, however, that the specific dose level for any particular patient will depend upon a variety of factors. Such factors include the age, body weight, general health, sex, and diet of the patient. Other factors include the time and route of administration, rate of excretion, drug combination, and the type and severity of the particular disease undergoing therapy.

The disclosed pharmaceutical compositions can further comprise other therapeutically active compounds, which are usually applied in the treatment of the above mentioned pathological conditions.

It is understood that the disclosed compositions can be prepared from the disclosed compounds. It is also understood that the disclosed compositions can be employed in the disclosed methods of using.

E. Examples

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in OC or is at ambient temperature, and pressure is at or near atmospheric.

Several methods for preparing the peptides of this invention are illustrated in the following Examples. Starting materials and the requisite intermediates are in some cases commercially available, or can be prepared according to literature procedures or as illustrated herein.

1. Chemicals and Abbreviations 1,4-Pentadiene, 1,6-heptadiene, 1,7-octadiene, 1,8-nonadiene, N-Acetyl-L-cysteine methyl ester, 2,2-dimethoxy-2-phenyl-acetophenone, piperidine, triisopropylsilane (TIS), 1,2-ethanedithiol (EDT) and reduced L-glutathione, azobisisobutyronitrile, anthraquinone-2-sulfonic acid sodium, 1,2-bis(4,5-dihydro-1H-imidazol-2-yl)propan-2-yl)diazene dihydrochloride, phenylbis(2,4,6-trimethylbenzoyl)phosphine oxide were purchased from Sigma-Aldrich. Dithiothreitol (DTT) and tris(2-carboxyethyl)phosphine hydrochloride (TCEP) were purchased from Gold Bio Technology. (R)—N-Fmoc-2-(7'-octenyl)alanine and (S)—N-Fmoc-2-(4'-pentenyl)alanine were provided by Okeanos Tech Jiangsu Co. Ltd. Fmoc-protected amino acids were obtained from Protein technologies Inc. O-(Benzotriazol-1-yl)-N,N,N',N'-tetramethyluronium (HBTU) and 1-[Bis(dimethylamino)methylene]-1H-1,2,3-triazolo[4,5-b]pyridinium 3-oxid hexafluorophosphate (HATU) were purchased from ChemPep. Rink Amide MBHA resin HL was obtained from Novabiochem and H-Rink Amide ChemMatrix was provided by Biotage. Dimethylformamide (DMF), N-methylpyrrolidinone (NMP), trifluoroacetic acid (TFA), acetonitrile and ethyl ether were purchased from Fisher Scientific and used as supplied.

The following dienes were used in the reactions discussed herein and are designated throughout with the compound numbers indicated in Table I below.

TABLE I

| Compound No. | Name | Structure |
|---|---|---|
| 2a | 1,7-octadiene | 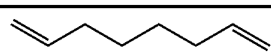 |
| 2b | 1,4-pentadiene | 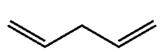 |
| 2c | 1,6-heptadiene | 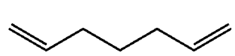 |
| 2d | 1,8-nonadiene | 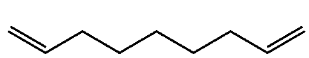 |
| 2e | 1,2-bis(allyloxy)ethane | 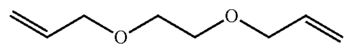 |
| 2f | 1,2-bis(allyloxy)benzene | 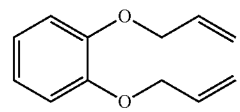 |
| 2g | 1,3-bis(allyloxy)benzene | 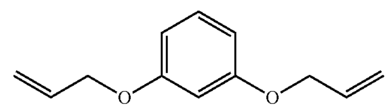 |
| 2h | 3,5-bis(allyloxy)benzoic acid | 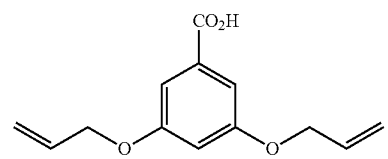 [SMILES: C=CCOc1cc(OCC=C)cc(C(=O)O)c1] |

The following radical initiators were used in the reactions discussed herein and are designated throughout with the compound numbers indicated in Table II below.

TABLE II

| Compound No. | Name | Structure |
|---|---|---|
| 4a | 2,2-dimethoxy-2-phenyl-acetophenone | 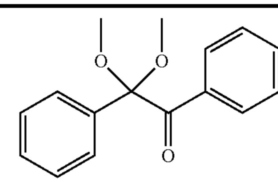 |
| 4b | anthraquinone-2-sulfonic acid sodium | 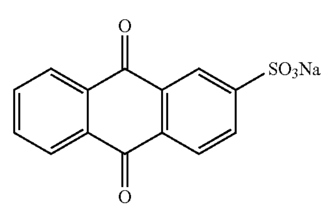 |
| 4c | phenylbis(2,4,6-trimethylbenzoyl)phosphine oxide | 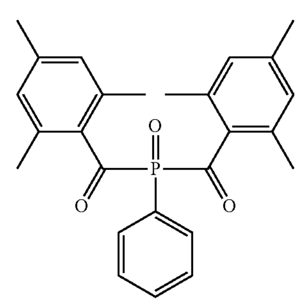 [SMILES: Cc1cc(C)c(C(=O)P(=O)(C(=O)c2c(C)cc(C)cc2C)c2ccccc2)c(C)c1] |
| 4d | azobisisobutyronitrile | 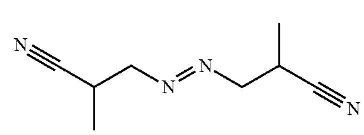 |

TABLE II-continued

| Compound No. | Name | Structure |
|---|---|---|
| 4e | 1,2-bis(4,5-dihydro-1H-imidazol-2-yl)propan-2-yl)diazene dihydrochloride | 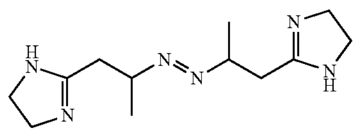 [SMILES: CC(CC1=NCCN1)/N=N/C(C)CC1=NCCN1] |

2. General Methods

Analytical thin layer chromatography (TLC) was performed on pre-coated silica gel plates available from EMD. Visualization was accomplished with UV light. Column chromatography was performed using Biotage chromatographic systems. $^1$H NMR and $^{13}$C NMR spectra were recorded on Varian Inova instrument (400 MHz). Chemical shifts were quoted in parts per million (ppm) referenced to the residual undeuterated solvent peak or 0.0 ppm for tetramethylsilane. The following abbreviations were used to explain multiplicities; s=singlet, d=doublet, t=triplet, m=multiplet. Coupling constants, J, were reported in Hertz unit (Hz). The yields were calculated based on the amount of the product after column chromatography using HPLC.

Preparative reverse-phase HPLC of crude peptides was performed on Luna 5u C8 100 Å (250×10 mm) at 3 mL/min with a water/acetonitrile gradient in 0.1% TFA on an Agilent 1260 HPLC system. Fractions collected from preparative were analyzed by LC/MS on a XBridge C18 5-μm (50×2.1 mm) column at 0.4 mL/min with a water/acetonitrile gradient in 0.1% formic acid on an Agilent 6120 Quadrupole LC/MS system. Fractions containing targeted product (based on LC/MS) were collected and lyophilized.

All CD spectra were recorded on an AVIV Model 410 spectrophotometer (AVIV) in water in a 1 mm QS quartz cuvette (Stama) at 25° C. Wavelength scans were performed at 1-nm resolution with 1-s averaging time. Data from double scans were averaged, blank subtracted, and normalized to mean residue ellipticity by the following equation; $[\theta]=100\times\theta/C\times l\times(n-1)$, where C is concentration of protein in mM, l is path length in centimeters, and n is the number of residues in the protein. The concentrations of the protein samples used for CD experiments were 100 μM. The percentage helicity was calculated from the absorbance at 222 nm using helical models as previously reported (Y. H. Chen, J. T. Yang, K. H. Chau. Biochemistry 1974, 13, 3350-3359).

3. Peptide Synthesis.

Peptides were synthesized via Fmoc solid phase peptide synthesis on a commercial peptide synthesizer (Alstra; Biotage, Inc.). Automated peptide synthesis was carried out in a 10 mL reactor vial with the following protocols (for 0.1 mmol scale). For Fmoc deprotection; (i) 4.5 mL of 20% piperidine in DMF; (ii) mix 2×3 min (new solvent delivered for each mixing cycle). For amino acid coupling: (i) 1.25 mL of 0.4 M Fmoc-protected amino acid in DMF; (ii) 1.225 mL of 0.4 M HBTU or HATU (HBTU and Rink Amide MBHA resin HL was used for peptides 5 and 7; HATU and H-Rink Amide ChemMatrix for peptides 10, 13, unstapled 9 and unstapled 12) in DMF; (iii) 1.0 mL of 1.0 M DIPEA in DMF; and (iv) mix for 5 min at 75° C. (for cysteine coupling: mix for 10 min at 50° C.). For DMF washing (performed between deprotection and coupling steps): (i) 4.5 mL of DMF; (ii) mix 45 s. For acetylation at the N-terminus (performed between the last deprotection and precleavage wash with DCM steps): (i) 1.0 mL of 5.0 M acetic anhydride in DMF; (ii) 5.5 mL of 1.0 M DIPEA in DMF; and (iv) mix for 10 min at 25° C. Upon completion of the peptide chain, resins were washed with DCM and dried (using vacuum) for 20 min. Then peptide was cleaved from the resin by exposure to cleavage cocktail for 2.5 h, which were prepared with 12.5 mL TFA, 330 μL water, 330 μL TIS, and 330 μL EDT. The peptide was precipitated with ethyl ether at 4° C. and lyophilized.

The sequence of Cys-containing peptides referred to herein throughout are as indicated in Table III below.

TABLE III

| Peptide No. | Sequence |
|---|---|
| Peptide 5 | Ac-Tyr-Cys-Lys-Glu-Ala-Cys-Ala-Leu-NH$_2$ (SEQ ID NO: 6) |
| Peptide 7 | Ac-Tyr-Cys-Lys-Glu-Ala-Gly-Gly-Gly-Ala-Cys-Leu-NH$_2$ (SEQ ID NO: 7) |
| Peptide 9 | Ac-Glu-Asn-Pro-GLu-S$_5$-Ile-Leu-Asp-S$_5$-His-Val-Gln-Arg-Val-Met-NH$_2$ (SEQ ID NO: 8) |
| Peptide 10 | Ac-Glu-Asn-Pro-Glu-Cys-Ile-Leu-Asp-Cys-His-Val-Gln-Arg-Val-Met-NH$_2$ (SEQ ID NO: 9) |
| Peptide 12 | Ac-Gln-Ser-Gln-Gln-Thr-Phe-R$_8$-Asn-Leu-Trp-Arg-Leu-Leu-S$_5$-Gln-Asn-NH$_2$ (SEQ ID NO: 10) |
| Peptide 13 | Ae-Gln-Ser-Gln-Gln-Thr-Phe-Cys-Asn-Leu-Trp-Arg-Leu-Leu-Cys-Gln-Asn-NH$_2$ (SEQ ID NO: 11) |

4. Reaction Between Protected Cysteine and 1,7-Octadiene.

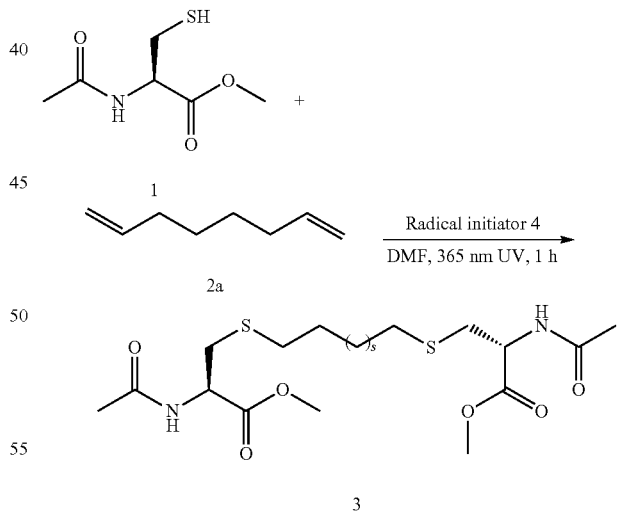

To the solution of 1,7-octadiene (2a, 1 mmol) and N-acetyl-L-cysteine methyl ester (2 mmol) in DMF (5 mL) was added the radical initiator (4a, 4b, 4c, 4d, or 4e; 0.2 mmol;). The reaction solution was stirred under UV irradiation (365 nm) for 1 h. Then the reaction solution was diluted with ethyl acetate (50 mL) and washed with water, brine, and dried with anhydrous Na$_2$SO$_4$. After concentration, the crude product was purified on flash chromatography (Biotage) using hexane/EtOAc (1/8) to afford compound 3. White solid; m.p. 106-107° C. (CHCl$_3$); IR 3277, 2926, 2853, 1744, 1654, 1538, 1435, 1372, 1212, 1175 cm$^{-1}$; $^1$H NMR (500 MHz CDCl$^3$): δ 6.38 (d, J=5.6 Hz, 2H), 4.80 (m, 2H), 3.75 (s, 6H), 2.96 (m, 4H), 2.48 (t, J=6.0 Hz, 4H), 2.03 (s, 6H), 1.52 (m, 4H), 1.32 (m, 4H), 1.26 (m, 4H); $^{13}$C NMR (125 MHz, CDCl$^3$): δ 171.3, 169.7, 52.5, 51.8, 34.1, 32.6, 29.4, 28.9, 28.5, 23.0; HRMS C$_{20}$H$_{36}$N$_2$O$_6$S$_2$ calculated: 465.2095 (M+H), found 465.2108.

The yields for the product, i.e., linked cysteine, resulting from reactions with each of 4a, 4b, 4c, 4d, or 4e is given below in Table IV. Of the radical initiators tested, compound 4a (2,2-dimethoxy-2-phenyl-acetophenone) provided the greatest overall yield in the model reaction wherein protected cysteine was the sulfhydryl source.

TABLE IV

| Compound No. | Amount in Reaction (eq.) | Yield (%) |
|---|---|---|
| 4a | 0.2 | 85 |
| 4b | 0.2 | 64 |
| 4c | 0.2 | 43 |
| 4d | 0.2 | 0 |
| 4e | 0.2 | 0 |

5. General Procedure for the Thiol-Ene Coupling Reaction.

To the solution of diene (one of 2a-2h; 5 µmol) and peptide (as indicated; 5 µmol) in NMP (0.5 mL) was added radical initiator 4a (0.5 mL). The reaction solution was stirred under UV irradiation (365 nm) for 15 minutes. The reaction solution was then diluted with distilled deionized water (1.5 mL) and the solution was washed with ethyl acetate (2 mL). After the separation of organic phase, the aqueous phase was subjected to preparative reverse-phase HPLC (Agilent 1260 HPLC system) and the product peptides were confirmed by ESI (Agilent 6120 Quadrupole LC/MS system). The yields were calculated based on the amount recovered after HPLC purifications. Mass spectrometry data for stapled peptides prepared using this method and for the parent peptides are shown in Table V below.

TABLE V

| Peptide No. | Calculated Mass in Da | Found Mass in Da | Method |
|---|---|---|---|
| 5 | 940.4 | 941.4 [M + H] | ESI |
| 6a | 1050.5 | 1051.5 [M + H] | ESI |
| 6b | 1008.5 | 1009.5 [M + H] | ESI |
| 6c | 1036.5 | 1037.5 [M + H] | ESI |
| 6d | 1064.5 | 1065.5 [M + H] | ESI |
| 6e | 1082.5 | 1083.5 [M + H] | ESI |
| 6f | 1130.5 | 1131.5 [M + H] | ESI |
| 6g | 1130.5 | 1131.5 [M + H] | ESI |
| 6h | 1174.5 | 1175.5 [M + H] | ESI |
| 7 | 1111.5 | 1112.5 [M + H] | ESI |
| 8a | 1221.6 | 1222.6 [M + H] | ESI |
| 8d | 1235.6 | 1236.6 [M + H] | ESI |
| 8e | 1253.6 | 1254.6 [M + H] | ESI |
| 8f | 1301.6 | 1302.6 [M + H] | ESI |
| 8g | 1301.6 | 1302.6 [M + H] | ESI |
| 8h | 1345.6 | 1346.6 [M + H] | ESI |
| 9 | 1870.0 | 1871.0 [M + H] | ESI |
| 10 | 1825.8 | 1826.8 [M + H] | ESI |
| 11a | 1935.9 | 1936.9 [M + H] | ESI |
| 11c | 1921.9 | 1922.9 [M + H] | ESI |
| 12 | 2136.2 | 1069.1 [M/2 + H] | ESI |
| 13 | 2021.9 | 1012.1 [M/2 + H] | ESI |
| 14a | 2132.0 | 1067.2 [M/2 + H] | ESI |
| 14d | 2146.0 | 1074.1 [M/2 + H] | ESI |

6. ELISA Assay for P53-MDM2 Interactions

The ELISA kit was purchased from Enzo Life Sciences (New York, USA). TMB substrate was purchased from Cell Signaling Technology (Massachusetts. USA). The assay was performed according to the manufacture's protocol. Briefly, p53 antibody was coated on a 96-well plate overnight. After the coating, peptides and p53-MDM2 protein complexes were diluted in assay buffer and added to the wells. After 1-hour incubation, all wells were washed and detection antibody was added. After another 1-hour incubation, SA-HRP was added and incubated for 30 minutes before TMB substrate was added. 1N HCl was then added to stop the color development and the signal was measure using automatic plate reader (BioTek Synergy Neo).

7. Cell-Viability Assays

Both HCT-116 cell lines, i.e., HCT-116 p53 wild-type and HCT-116 p53 null, were obtained from Dr. Trudy Oliver (University of Utah). Cell lines were cultured in 10% FBS media (DMEM, Pen/Strep). Briefly. 20,000 cells/well in 1% FBS media were seeded in 96-well plates. After 24 hours, stapled peptides with various concentrations were added to each well. After another 24-hour incubation, media were aspirated and CellTiter Glo reagent was added according to the protocol from Promega. Luminescence signal was measured by automatic plate reader (BioTek Synergy Neo).

8. Thiol-Ene Coupling Reaction: Peptide 5.

The thiol-ene coupling reaction was examined using peptide 5, YCKEACAL, which has multiple unprotected functional groups in order to evaluate the chemoselectivity of this stapling method as a general macrocyclization method (see FIG. 1 for overall reaction scheme and peptide structures). The resulting product was expected to be a cyclic peptide with five amino acids and a linker. Peptide 5 (2 mM) was incubated with diene 2a (1 eq) in the presence of DMPA (1 eq) in DMF or NMP. The yield of the desired product, 6a, was 65% when the reaction was carried out using DMF as the solvent, whereas the yield of the product, 6a, was 90% when the reaction was carried out using NMP as the solvent. The HPLC and MS data indicate that the thiol-ene coupling is chemoselective to thiol groups in the presence of functional groups such as amines, alcohols and carboxylic acids.

Figure 2:
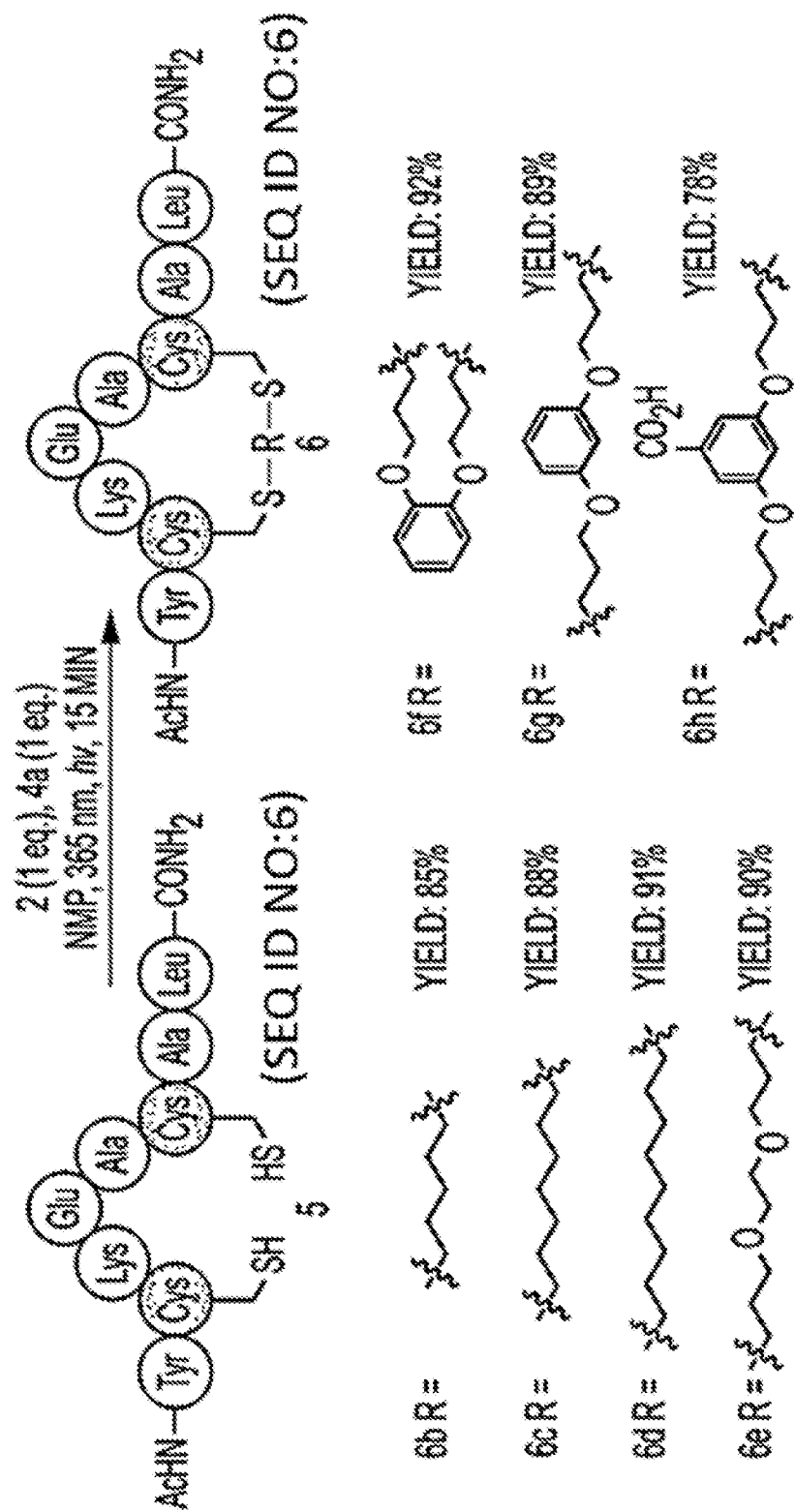
FIG. 2 shows a representative thiol-ene two-component coupling reaction between an exemplary unprotected peptide, peptide 5, and the exemplary dienes shown in FIG. 12.
Figure 3:
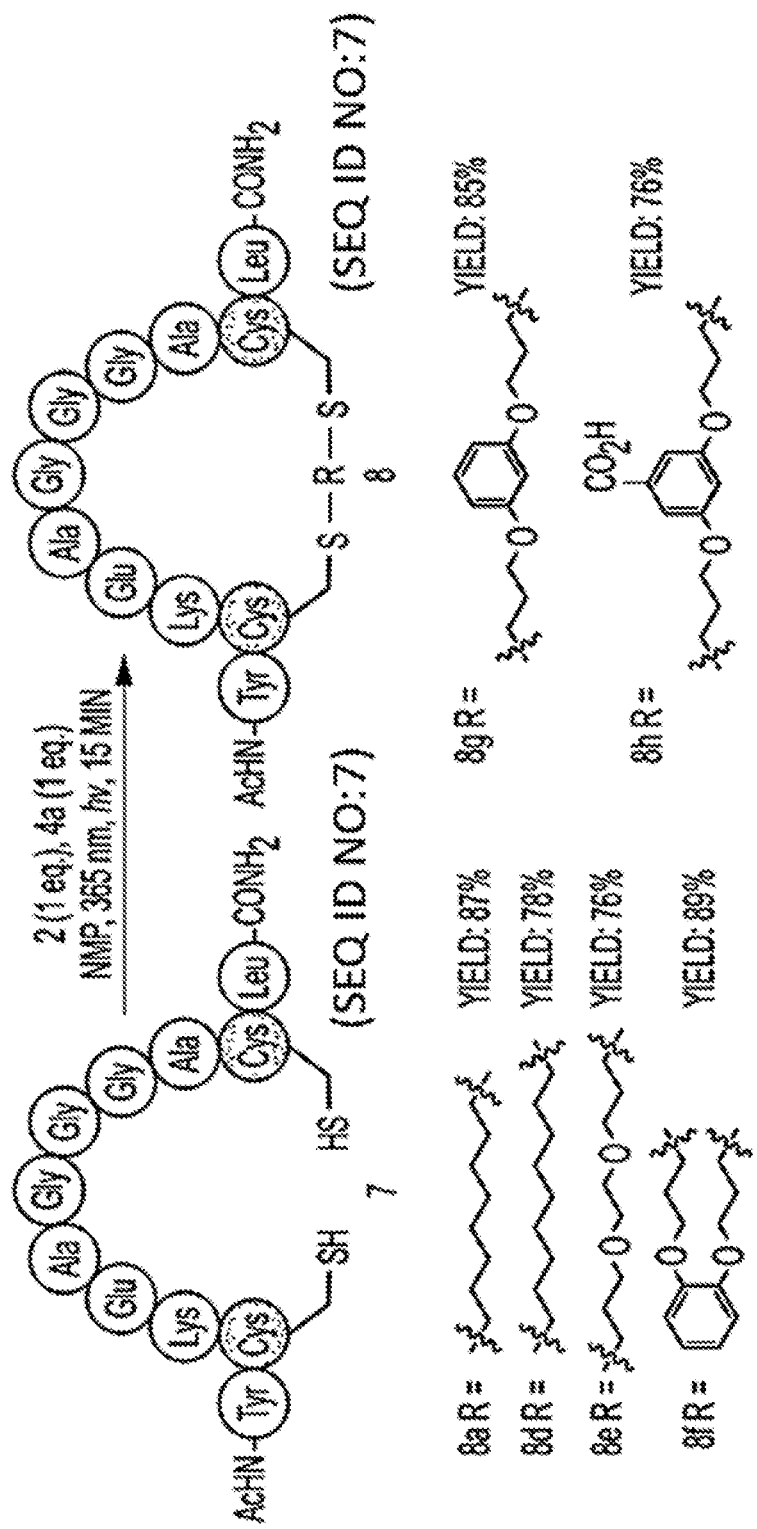
FIG. 3 shows a representative thiol-ene two-component coupling reaction between an exemplary unprotected peptide, peptide 7, and the exemplary dienes shown in FIG. 12.

The substrate scope was assessed using dienes with various length or heteroatom substituted linkers (see Table I for list of dienes tested) when reacted with peptide 5. All seven dienes reacted with peptide 5 in high yields (see FIG. 2). The reaction was evaluated with longer peptides. Peptide 7 has seven amino acids between the two Cys residues and the expected cyclized peptide has nine amino acids and a linker. The overall reaction scheme, with peptide structures and product yields are shown in FIG. 3. The data show that various cyclized peptides were synthesized in excellent yields using different diene linkers. The data show that the disclosed thiol-ene coupling reaction represents an efficient approach in synthesizing cyclic peptides with flexible linker choices from native, unprotected peptides.

9. Thiol-Ene Coupling Reaction: Axin.

Figure 4A:
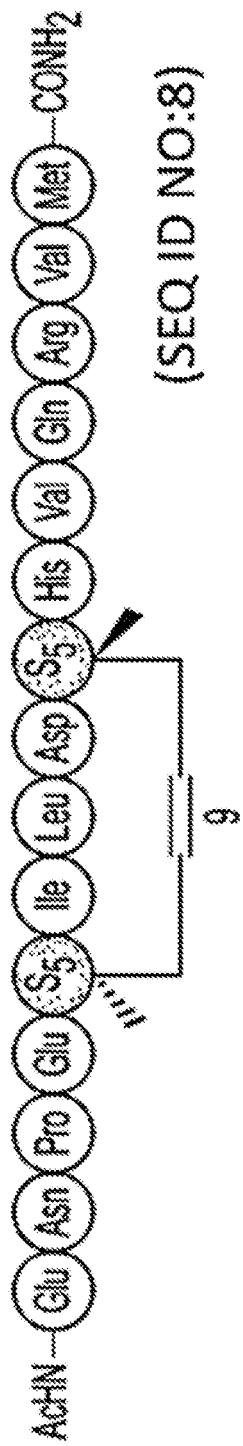
FIG. 4A shows the structure of a stapled axin analog previously reported by Grossmann, T. N., et al. *Proc. Natl. Acad. Sci. U.S.A.*, 2012, 109, 17942-17947.
Figure 4B:
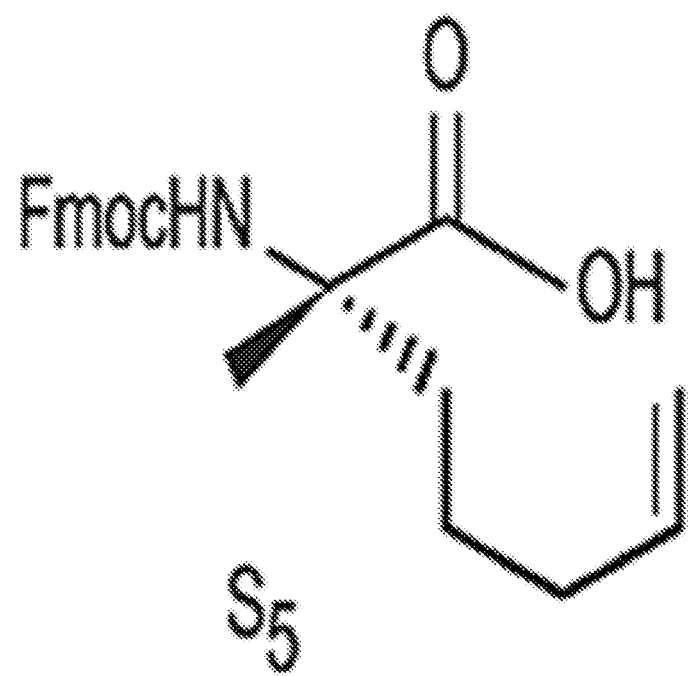
FIG. 4B shows the structure of the $S_5$ amino acid used in the synthesis of the stapled axin analog shown in FIG. 4A.
Figure 4C:
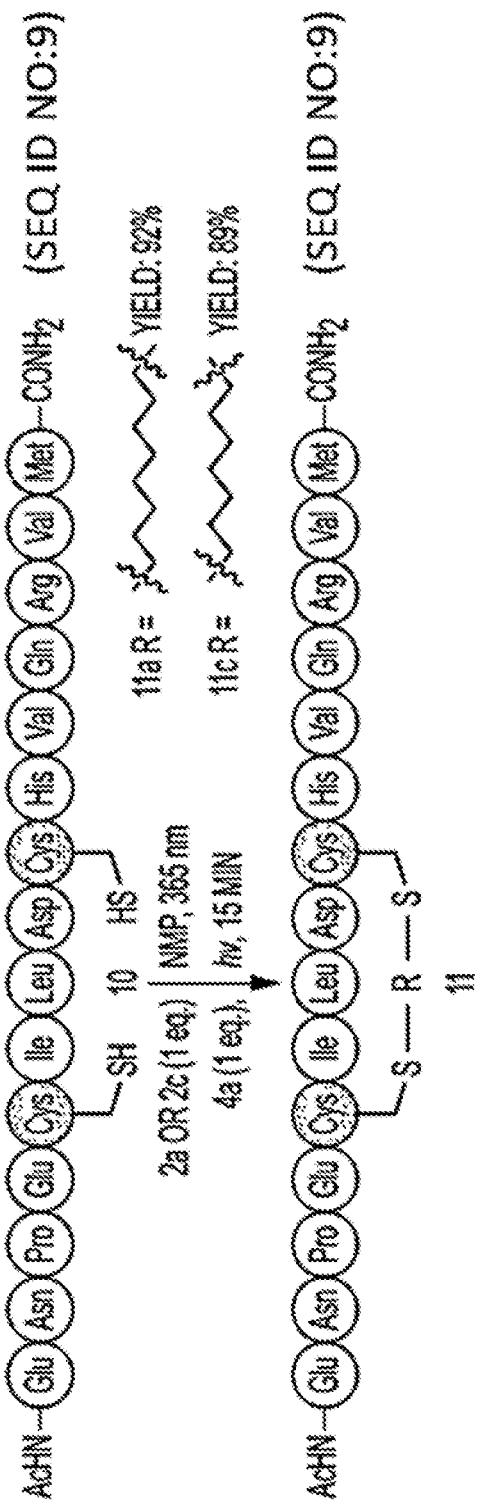
FIG. 4C shows a representative synthesis of a stapled axin analog using the disclosed methods.

The classic ring-closing metathesis ("RCM") approach is a typically used method to synthesize hydrocarbon linker stapled peptides. By using special UAAs, stapled peptides with i, i+4 or i, i+7 linkages have been prepared by this method (Y. W. Kim, et al., Nat. Protoc. 2011, 6, 761-771.). However, solid-phase peptide synthesis is needed due to the requirement of using unnatural amino acids ("UAAs") and this limits its efficient use in longer peptides (>50 residues), which are generally expressed using the recombinant DNA technology. In order to assess the use of the disclosed thiol-ene coupling for direct peptide stapling of natural, unprotected peptides, the reaction was used to create stapled axin homologues. The stapled axin peptides prepared by the disclosed thiol-ene coupling reaction were compare to peptide 9 (see FIG. 4A), a stapled Axin mimetic analog that was previously described and prepared as an inhibitor of the Wnt signaling pathway (T. N. Grossmann, et al., Proc. Natl. Acad. Sci. U.S.A. 2012, 109, 17942-17947). The incorporation of two $S_5$ amino acids (see FIG. 4B for structure) followed by RCM gave the i, i+4 stapled peptide 9 (FIG. 4A). The unstapled axin homologue, peptide 10, was synthesized and it has 2 Cys residues to replace the two S amino acids of peptide 9. Peptide 10 was then reacted with either diene 2a or 2c to form peptide 11a and 11c via the disclosed thiol-ene coupling method (FIG. 4C). Circular dichroism (CD) experiments were used to evaluate the alpha helicity of the staples peptides. Both the unstapled peptide 10 and stapled peptide 11c (7-carbon linker) have a low alpha-helical property. However, both literature reported peptide 9 and stapled peptide 11a (8-carbon linker) have strong alpha-helical characteristics as shown in FIG. 11. These data suggest that the disclosed thiol-ene coupling reaction leads to the same structural features of the classic RCM method in stapling i, i+4 pairs.

10. Thiol-Ene Coupling Reaction: p53.

Figure 5A:
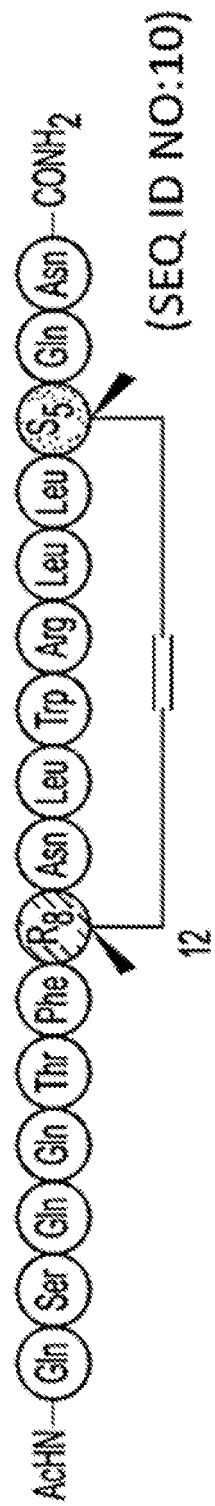
FIG. 5A shows the structure of a stapled p53 analog previously reported by Bernal, F., et al., *J. Am. Chem. Soc.*, 2007, 129, 2456-2457.
Figure 5B:
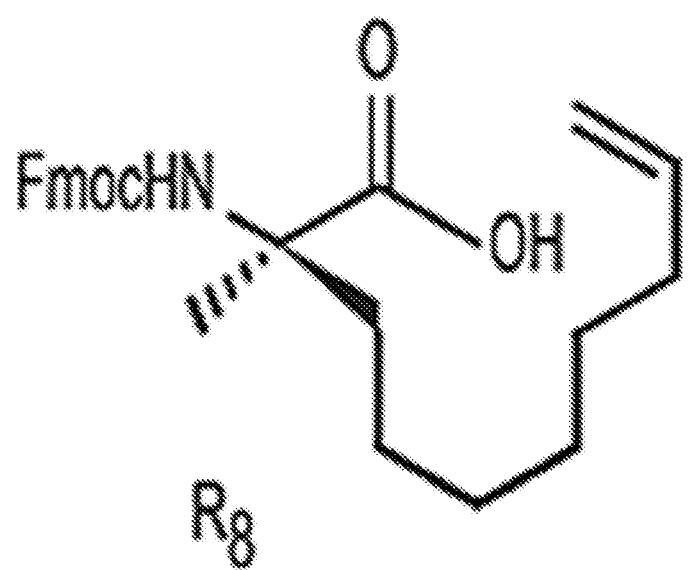
FIG. 5B shows the structure of the $R_8$ amino acid used in the synthesis of the stapled axin analog shown in FIG. 5A.
Figure 5C:
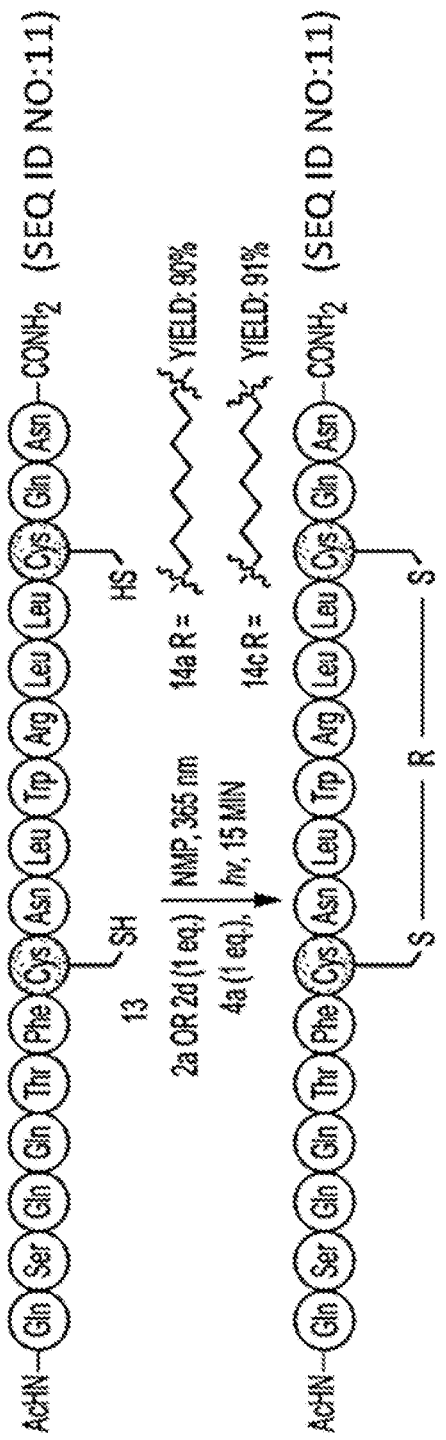
FIG. 5C shows a representative synthesis of a stapled p53 analog using the disclosed methods.
Figure 6:
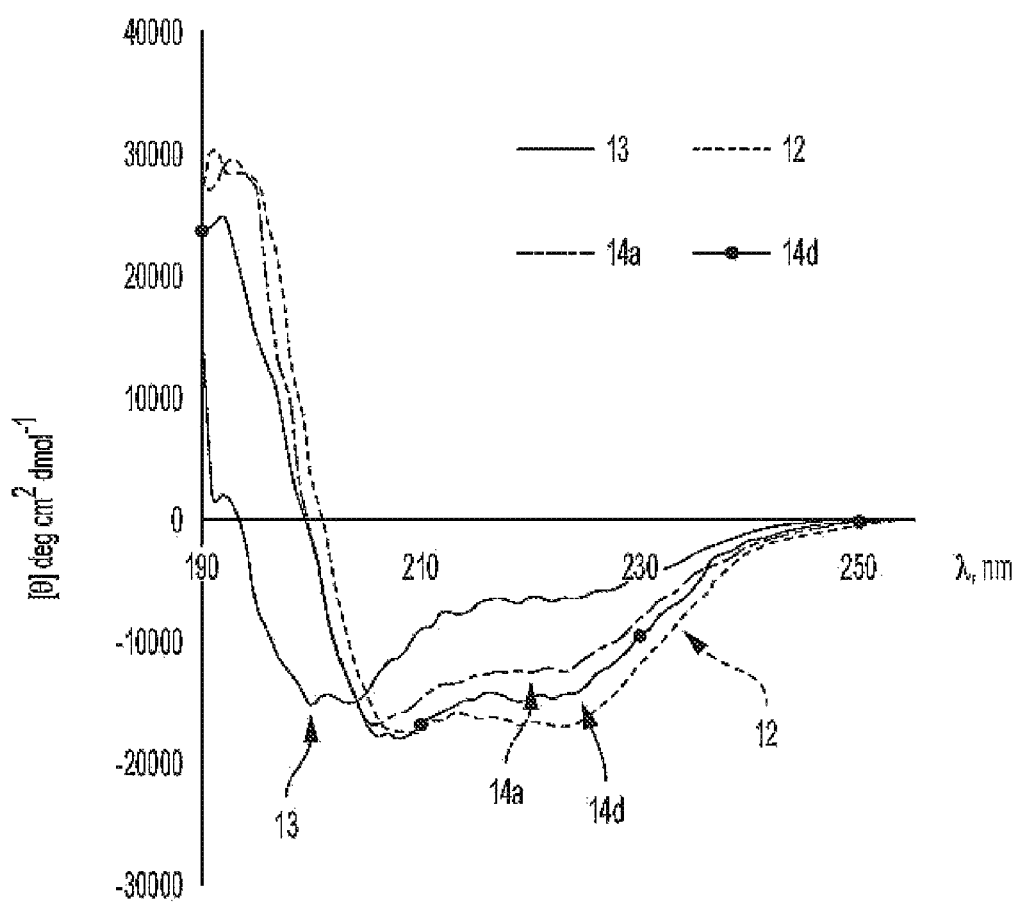
FIG. 6 shows representative CD spectra of peptides 12, 13, 14a, and 14d. The peptide numbers correspond to those shown in FIG. 5C and the Examples.
Figure 7:
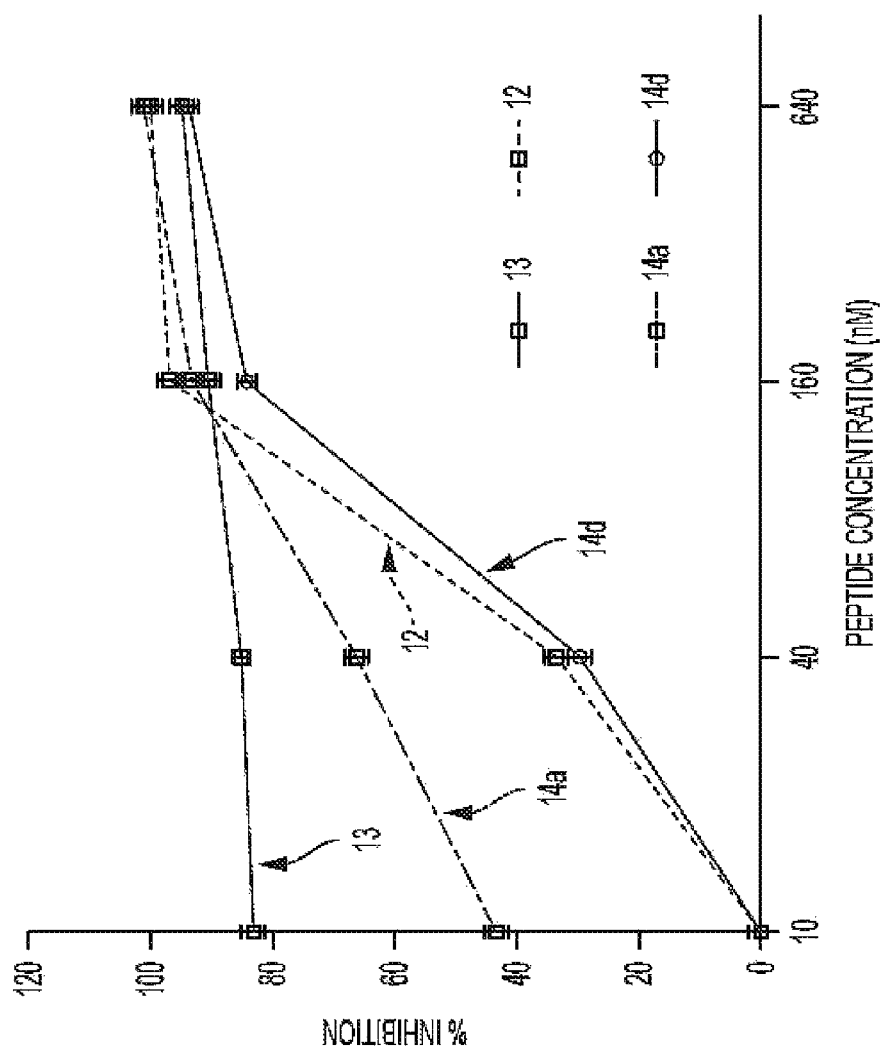
FIG. 7 shows representative data showing the inhibition of the p53-MDM2 interaction as determined in an ELISA binding assay using peptides 12, 13, 14a, and 14d. The peptide numbers correspond to those shown in FIG. 5C and the Examples.
Figure 8:
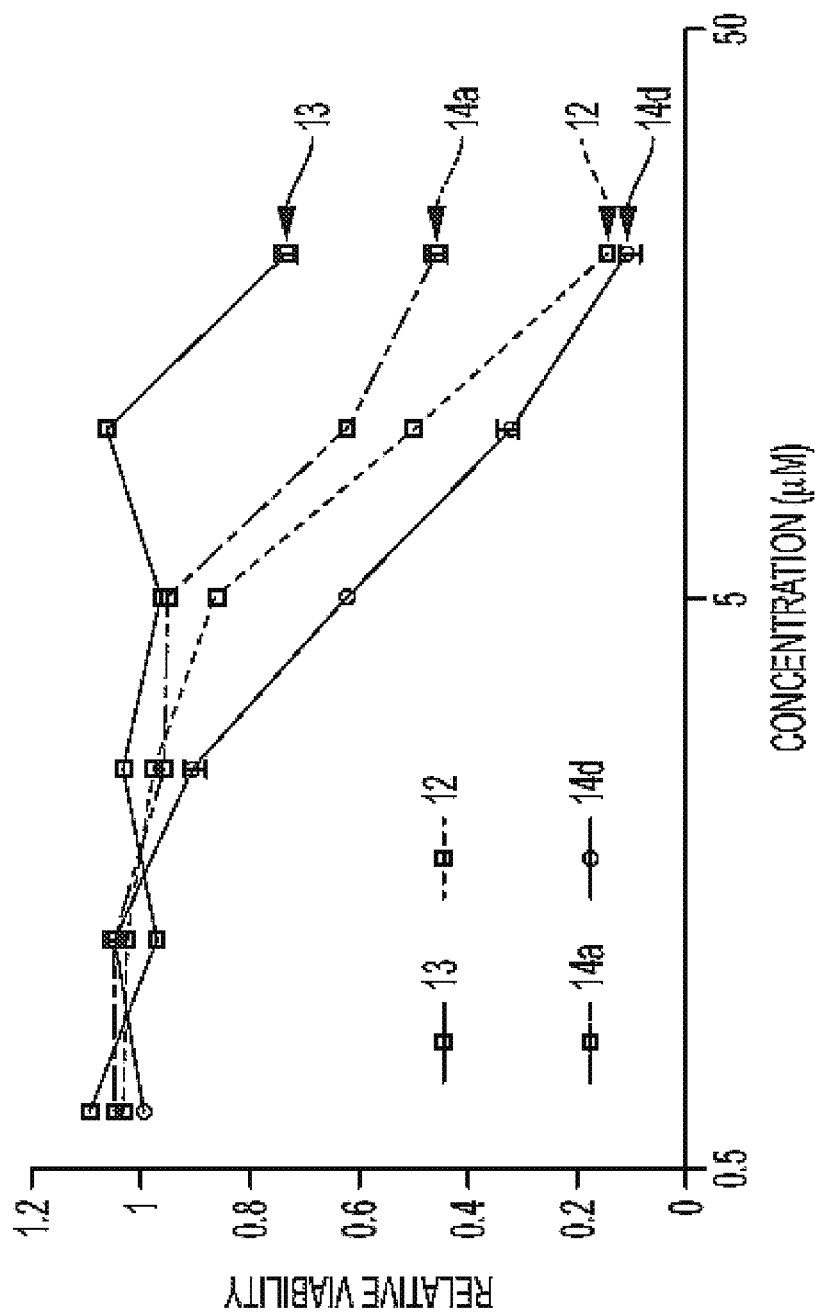
FIG. 8 shows representative data showing the effect of peptides 12, 13, 14a, and 14d on cell viability as determined using p53 wild-type HCT-116 cells. The peptide numbers correspond to those shown in FIG. 5C and the Examples.
Figure 9:
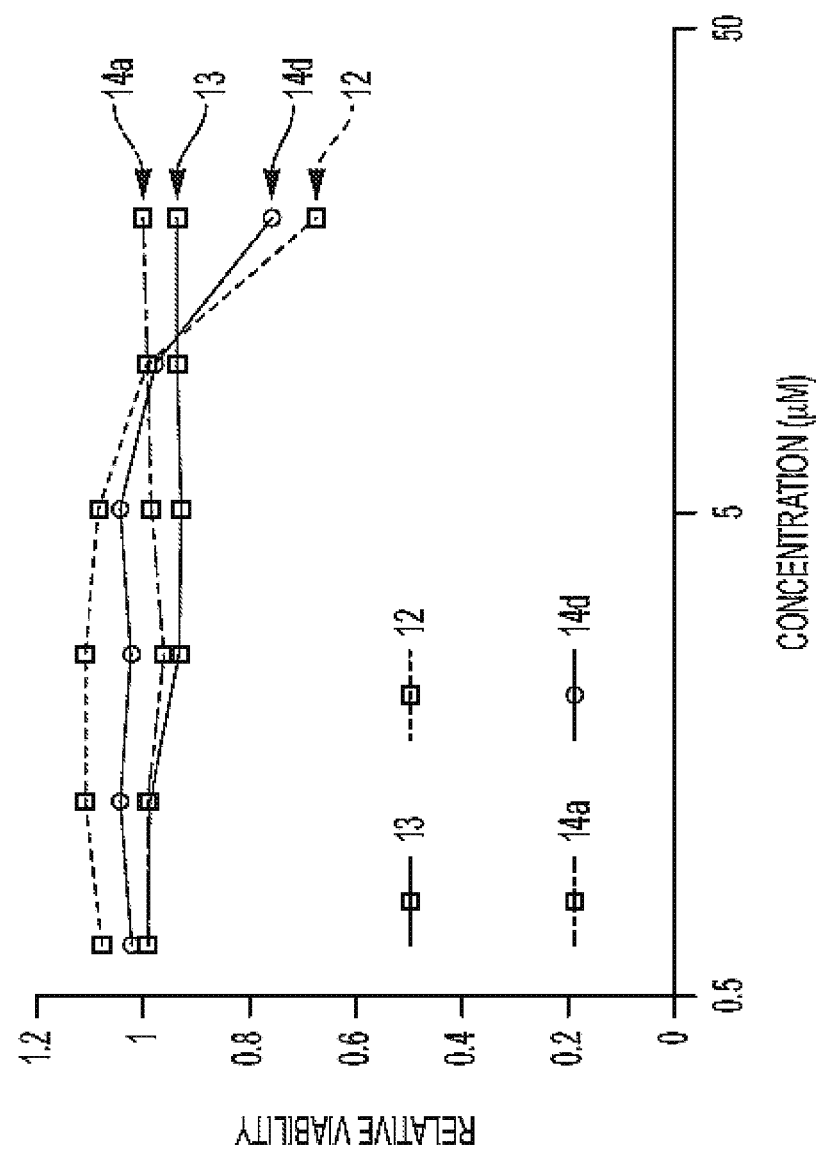
FIG. 9 shows representative data showing the effect of peptides 12, 13, 14a, and 14d on cell viability as determined using p53 null HCT-116 cells. The peptide numbers correspond to those shown in FIG. 5C and the Examples.
Figure 10:
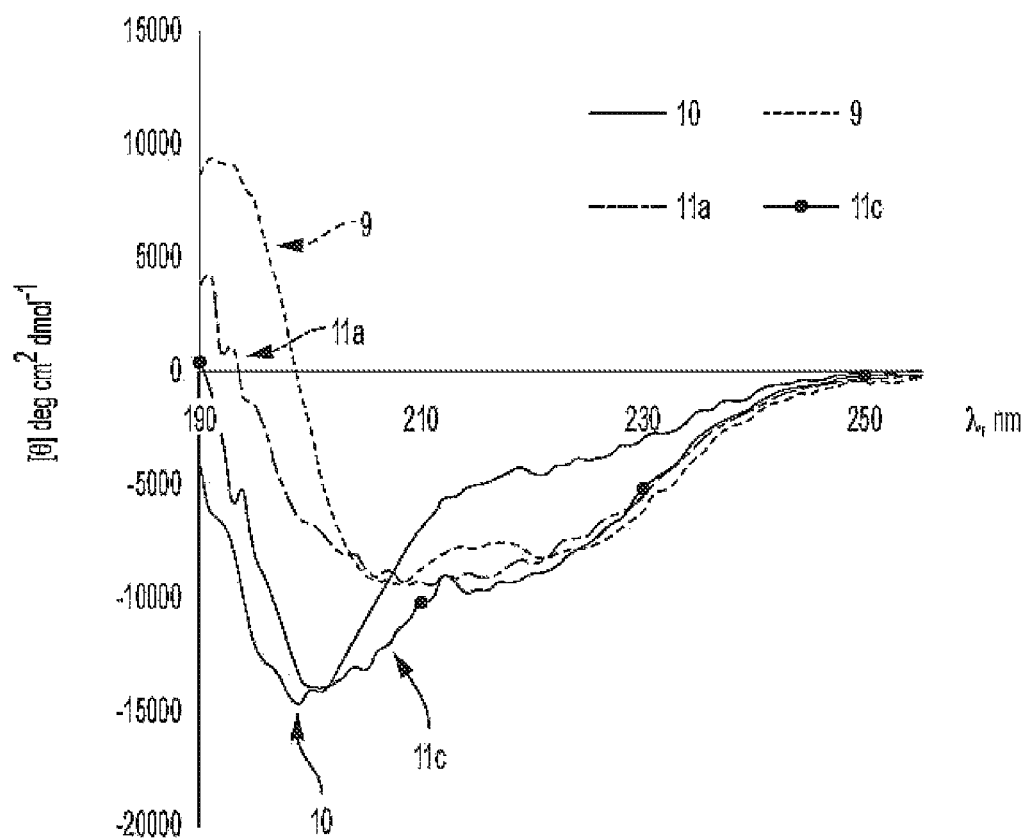
FIG. 10 shows representative CD spectra of peptides 9, 10, 11a, and 11c. The peptide numbers correspond to those shown in FIG. 4C and the Examples.

In order to further assess the use of the disclosed thiol-ene coupling for direct peptide stapling of natural, unprotected peptides, the reaction was used to create stapled p53 homologues. The stapled p53 peptides prepared by the disclosed thiol-ene coupling reaction were compare to peptide 12 (see FIG. 5A), an i, i+7 stapled p53 mimetic analog that was previously described and prepared to block the interaction between p53 and MDM2 (F. Bernal, et al., J. Am. Chem. Soc. 2007, 129, 2456-2457). Due to the longer distances in the i, i+7 pair, an $R_8$ amino acid was used together with an $S_5$ amino acid for the stapling (FIG. 5B). The unstapled p53 homologue, peptide 13, was synthesized and it has 2 Cys residues to replace the $S_5$ and $R_8$ amino acids of peptide 12. Peptide 13 was reacted with either diene 2a or 2d to form peptides 14a or 14d, respectively, via the disclosed thiol-ene coupling (FIG. 5C). As the CD spectra data show (see FIG. 6), all the stapled peptides 12, 14a and 14d have a significant increase of alpha helicity compared to the unstapled peptide 13. Specifically, 14d has a similar alpha-helical characteristic with the reported stapled peptide 12 (see FIG. 6). To test whether the structural feature translates to the functional relevance, an ELISA assay was performed to quantify the interaction between p53 and MDM2 in the presence of the peptides (see FIG. 7). For peptide 12, a similar efficacy was observed in blocking the p53-MDM2 interaction as reported in literature. The data clearly show that the cysteine-stapled peptide 14d was as effective as peptide 12. (FIG. 7), whereas the unstapled peptide 13 did not block the p53-MDM2 interaction. The efficacy of these peptides was also determined using a cell viability assay in p53 wild-type and p53-null HCT-116 colorectal carcinoma cells using peptides 12, 14a, and 14d (see FIGS. 8 and 9). It was previously reported that peptide 12 selectively induces cell apoptosis in p53 wild-type cells but not p53 null cells (F. Bernal, e al., Cancer Cell 2010, 18, 411-422). The same trend was observed for both peptides 14a and 14d also, i.e., induction of apoptosis in p53 wild-type cells but not p53 null cells, as for peptide 12. Thus, these data demonstrate that stapled peptides synthesized from native, unprotected peptides via the disclosed thiol-ene coupling can provide peptides with the desired biological activities as demonstrated in the p53 mimetics prepared using classic RCM methods.

The disclosed thiol-ene coupling reaction provides a facile and efficient synthetic platform for native peptide macrocyclization and stapling. The disclosed thiol-ene coupling method has been demonstrated herein to operates at room temperature under 15-min UV irradiation with excellent functional group tolerance. The utility of the disclosed thiol-ene coupling reaction as a general macrocyclization method using various diene linkers has been demonstrated herein. In addition, the disclosed thiol-ene coupling reaction has been demonstrated herein to be useful in synthesizing stapled peptides with both i, i+4 and i, i+7 linkages. Importantly, the synthesized stapled peptides prepared using the disclosed thiol-ene coupling reaction demonstrate the same biological properties reported in the literature for stapled peptides prepared using the classical RCM method. The disclosed thiol-ene coupling method has significant advantages in that it can be used directly on unprotected peptides without the use of UAAs and metal-based catalysts. The application of the disclosed thiol-ene coupling method can be generally used in stapling a variety of peptides, both large and small, as well as proteins.

11. Conducting the Thiol-Ene Reaction in Aqueous Solution

Figure 16:
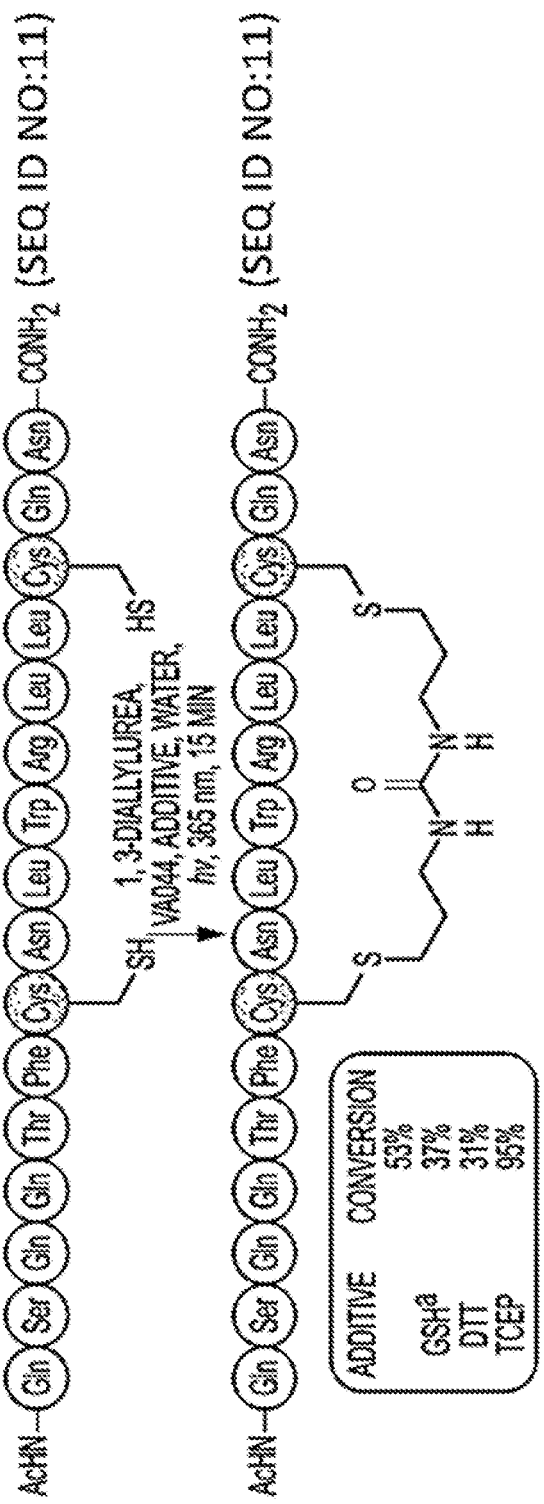
FIG. 16 shows peptide stapling under aqueous conditions.

As shown in FIG. 16, a staple can be selected so as to perform the thiol-ene reaction under aqueous conditions. Reaction conditions: 1,3 diallylurea (1 equiv) was reacted with VA044 (1 equiv) under hv exposure at 365 nm for 15 min. After 15 minutes, the conversion was 53% calculated based on the HPLC and LCMS analysis. The reaction solution was clear, and LCMS only showed starting peptide and stapled peptides. Without wishing to be bound by theory, it is believed that increasing reaction time may not improve the reaction. That is, after 20 minutes, there was observed some oxidation of starting peptide and stapled peptide (MS+16 Da).

To attempt to remedy oxidation, the reaction was repeated with additive: 1,3 diallylurea (1 equiv) was reacted with VA044 (1 equiv) in the presence of DTT (1 equiv) under hv exposure at 365 nm for 15 min. There was no observed improvement on the conversion.

In a further attempt to remedy oxidation, the reaction was repeated with additive: 1,3 diallylurea (1 equiv) was reacted with VA044 (1 equiv) in the presence of GSH (1 equiv) under hv exposure at 365 nm for 15 min. There was no observed improvement on the conversion. Again, there was no observed improvement on the conversion.

Figure 17:
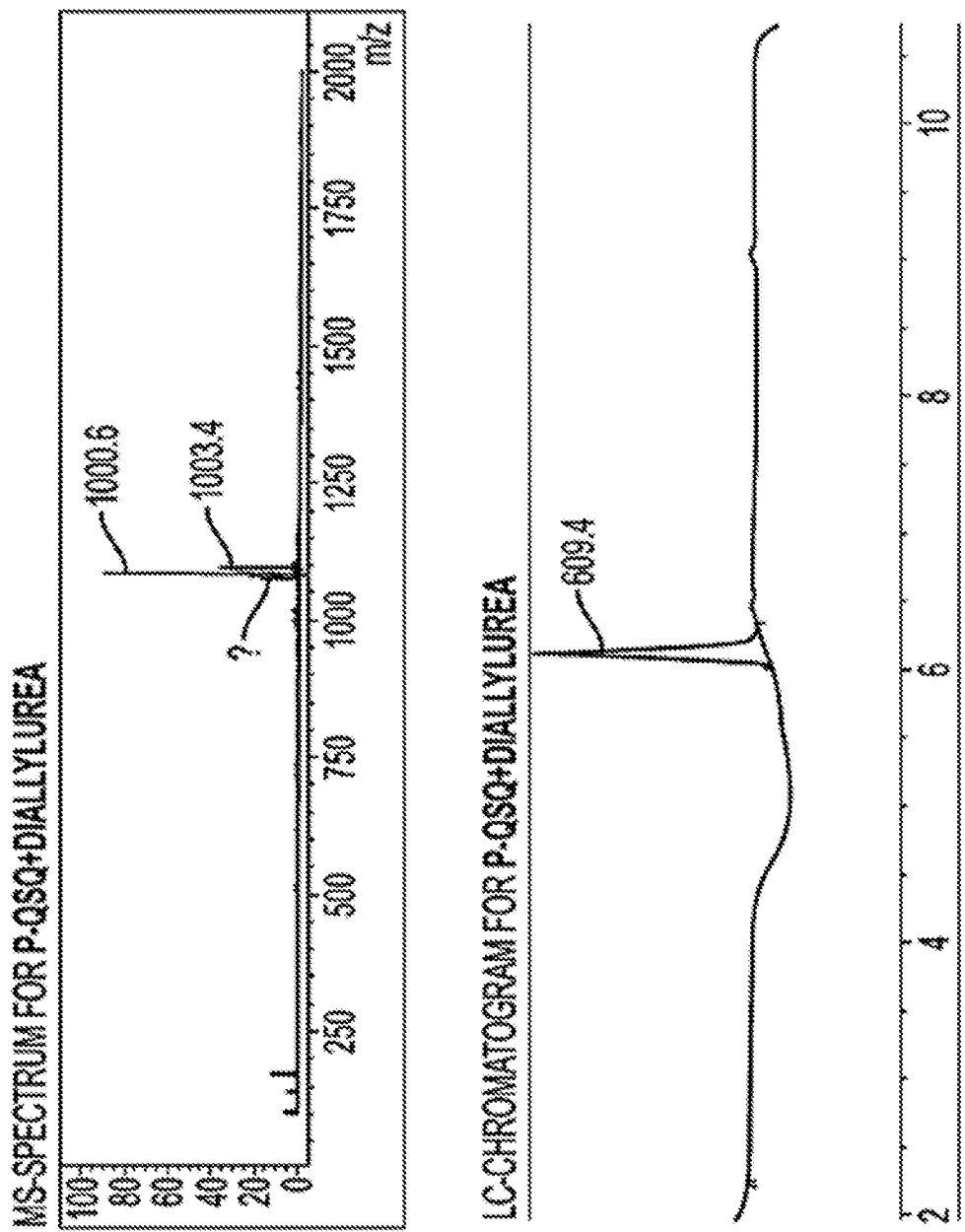
FIG. 17 shows characterization data for p-QSQ+diallylurea.

In a further attempt to remedy oxidation, the reaction was repeated with additive: 1,3 diallylurea (1 equiv) was reacted with VA044 (1 equiv) in the presence of TCEP (1 equiv) under hv exposure at 365 nm for 15 min. The reaction was improved, and the conversion was improved to 95%. TCEP, as a reducing agent, is usually used to break disulfide bonds; however, no disulfide bond was detected. Without wishing to be bound by theory, it is believed that TCEP's function here may be to facilitate the solubility of peptide in water. Characterization data for p-QSQ+diallylurea is shown in FIG. 17

12. Staple Coiled-Coils as Bcr-Abl Inhibitors

Figure 18:
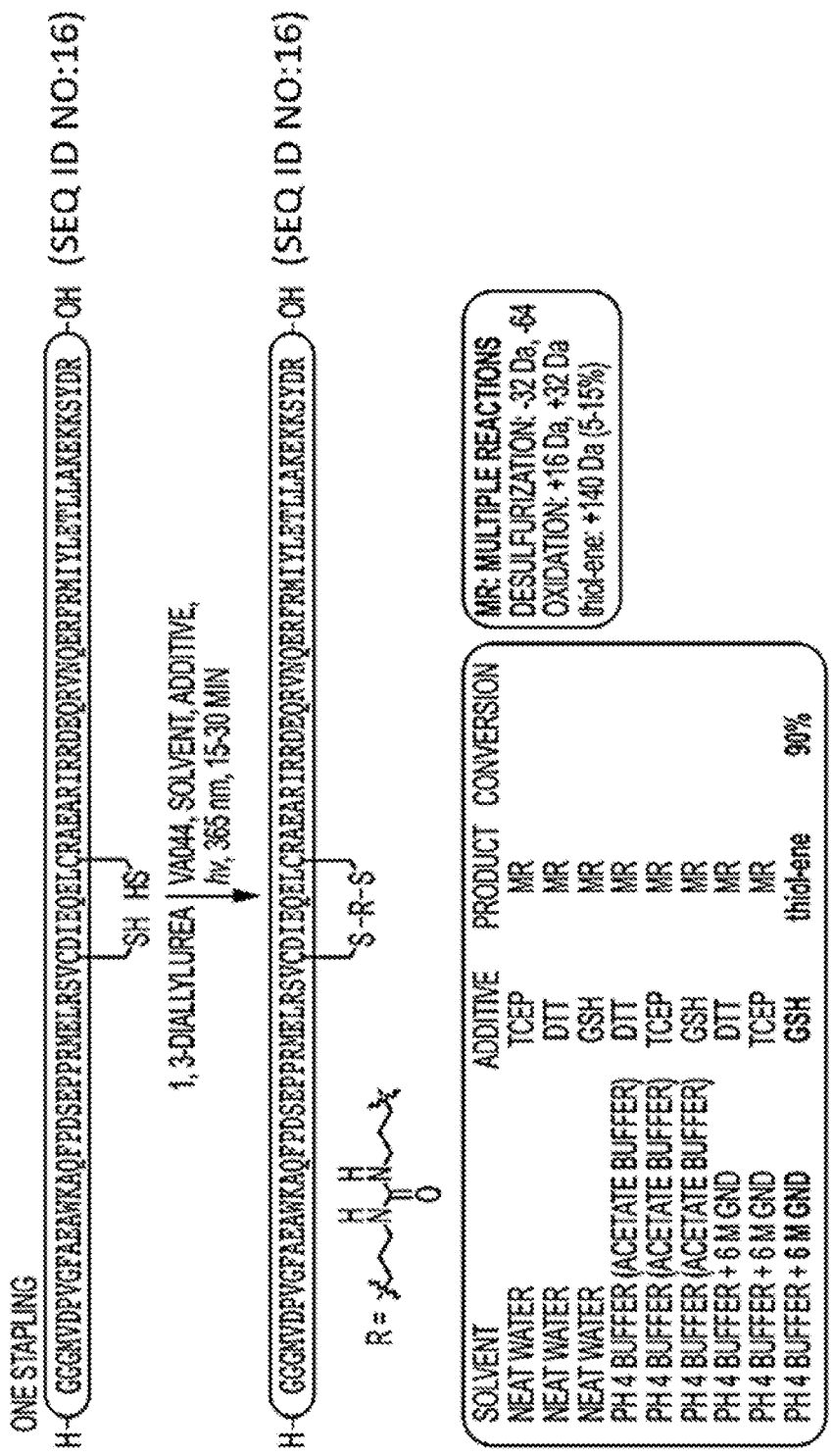
FIG. 18 shows single stapling can provide Bcr-Abl inhibitors.

As shown in FIG. 18, stapling can provide Bcr-Abl inhibitors. Bcr-Abl tyrosine-kinase inhibitors (TKI) are the first-line therapy for most patients with chronic myelogenous leukemia (CML). In one aspect, this can be done with a single stapling. Reaction conditions: As an initial example, the reaction conditions from the previous example were investigated. 1,3 diallylurea (1 equiv) was reacted with VA044 (1 equiv) in the presence of TCEP (1 equiv) and water under hv exposure at 365 nm for 15 minutes. This reaction showed that TCEP can lead to desulfurization of the protein substrate (the major product), which accorded with the paper published by Chuan-Fa Liu (ACIE, 2011, 9611).

In a further reaction, TCEP was replaced with DTT [1.3 diallylurea (1 equiv), VA044 (1 equiv), DTT (1 equiv), water, hv. 365 nm, 15 min]. No desulfurization was detected, but no desired product was formed. Instead, oxidation of the starting proteins was found.

In a further reaction, 1,3 diallylurea (3 equiv) was reacted with VA044 (1 equiv) in the presence of GSH (1 equiv) under exposure to hv at 365 nm for 15 minutes. Because GSH can react with dienes, additional diene was added for this reaction. Oxidation was observed, with no desired product observed.

In a further reaction, as reported (Liu, ACIE, 2011, 9611), an weakly acidic PH buffer can prevent the oxidation of the starting protein, so acetate buffer at PH 4 was used as solvent to run the reaction. 1,3 diallylurea (1 equiv) was reacted with VA044 (1 equiv) in the presence of DTT (1 equiv) with acetate buffer, under exposure to hv at 365 nm for 15 minutes. Less oxidation was observed, but the conversion to the title product was low (15%).

In a further reaction, 1,3 diallylurea (3 equiv) was reacted with VA044 (I equiv) in the presence of GSH (1 equiv) with acetate buffer under exposure to hv at 365 nm for 15 minutes. Less oxidation was observed, but the conversion to the title product was low (20%).

It was appreciated that 6N Gdn solution can be added to the solution to facilitate its solubility, so 6 N Gdn was added to the reaction mixture. Accordingly, in a further reaction, 1,3 diallylurea (3 equiv) was reacted with VA044 (1 equiv) in the presence of DTT (1 equiv) with acetate buffer, 6 N Gdn, and HCl under exposure to hv at 365 nm for 15 minutes. No improvement was observed when DTT was used as additive.

In a further reaction, 1,3 diallylurea (3 equiv) was reacted with VA044 (1 equiv) in the presence of GSH (1 equiv) with acetate buffer, 6 N Gdn, and HCl under exposure to hv at 365 nm for 15 minutes. The reaction progressed satisfactorily (conversion 90%) when GSH was used as additive.

Figure 19:
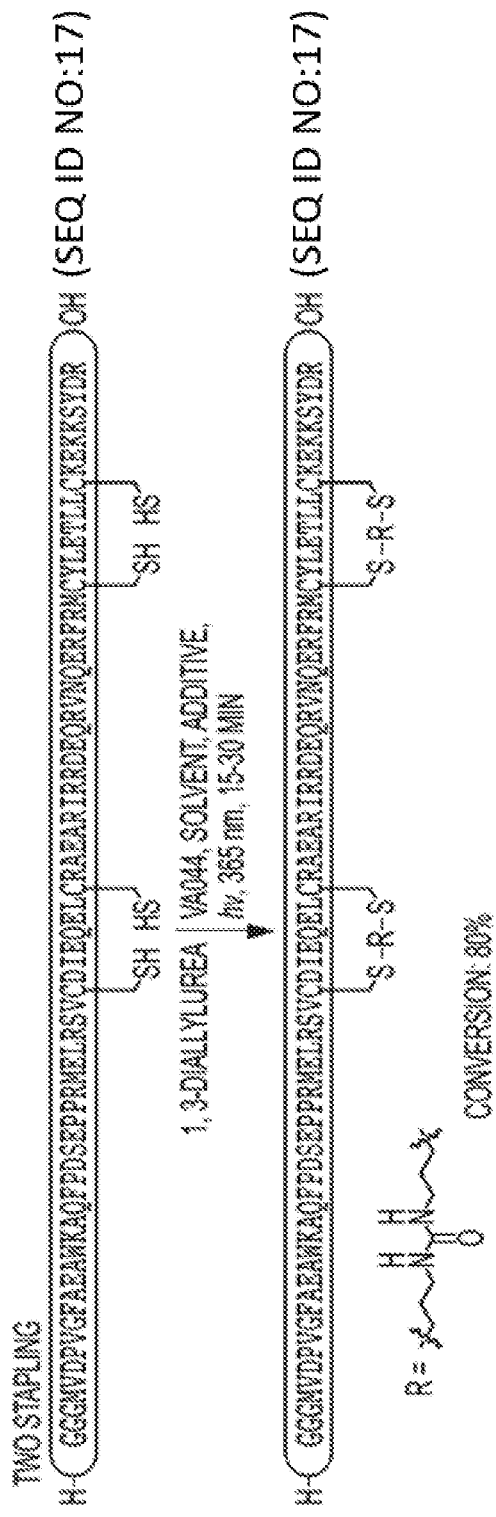
FIG. 19 shows double stapling can provide Bcr-Abl inhibitors.
Figure 20:
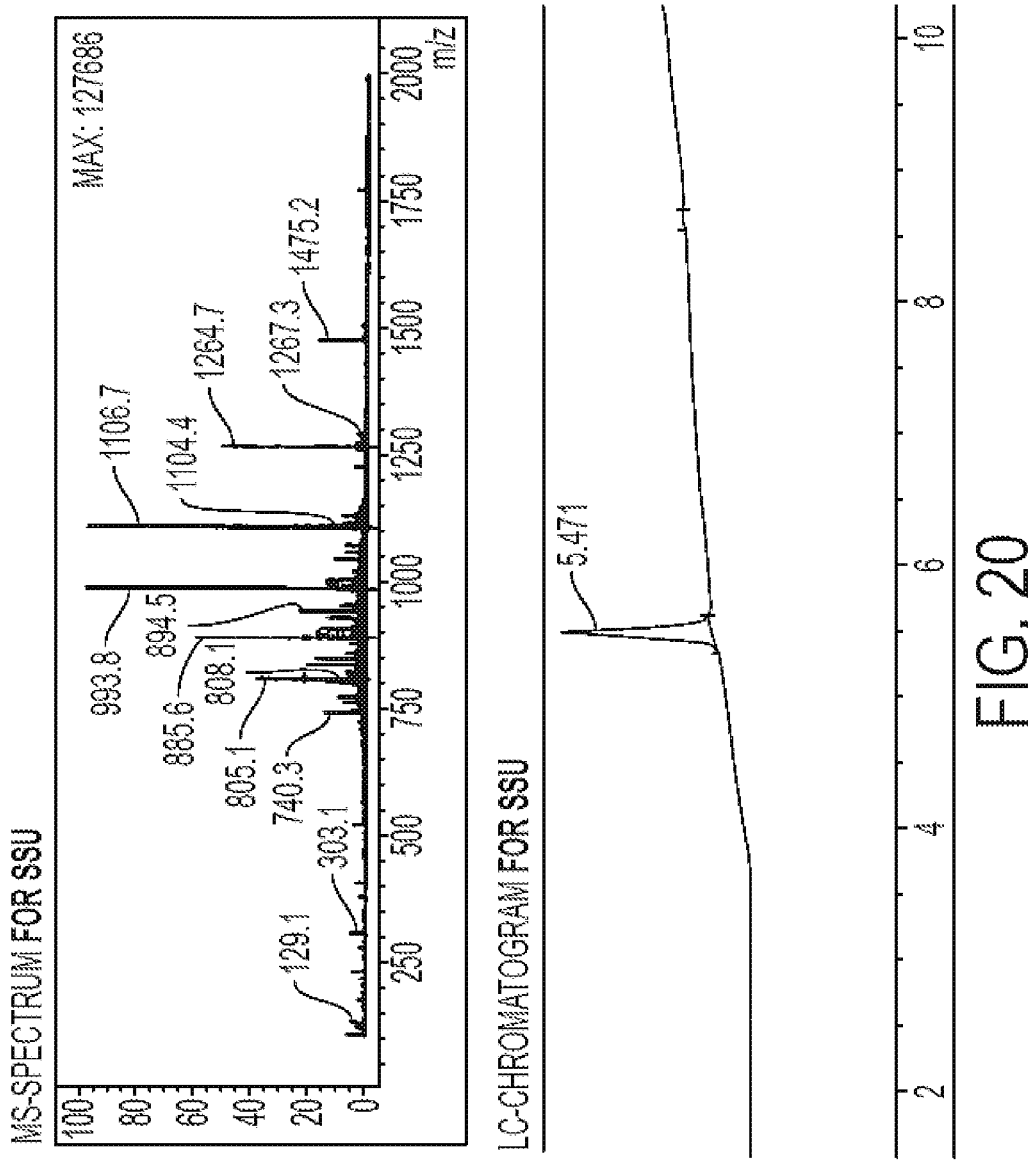
FIG. 20 shows characterization data for SSU.
Figure 21:
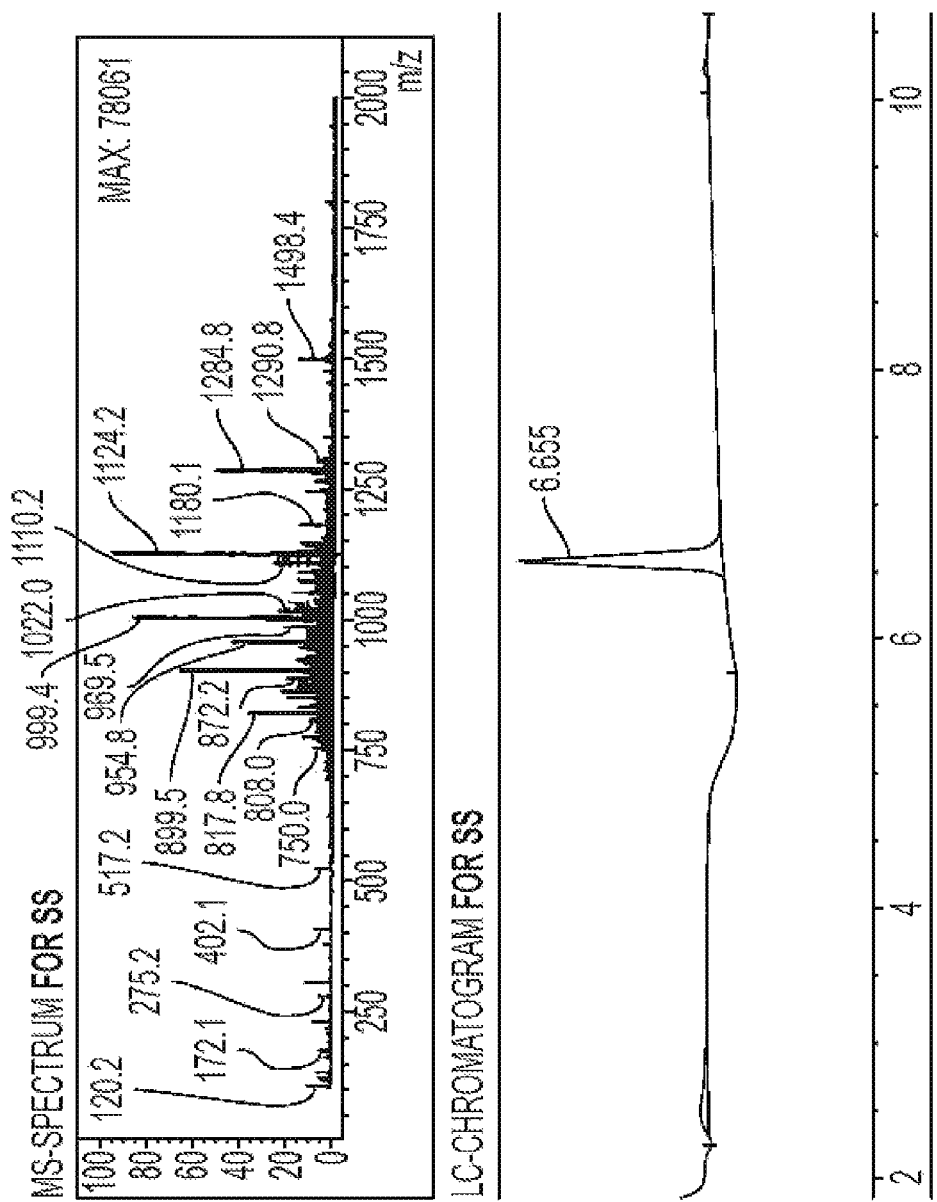
FIG. 21 shows characterization data for SS.
Figure 22:
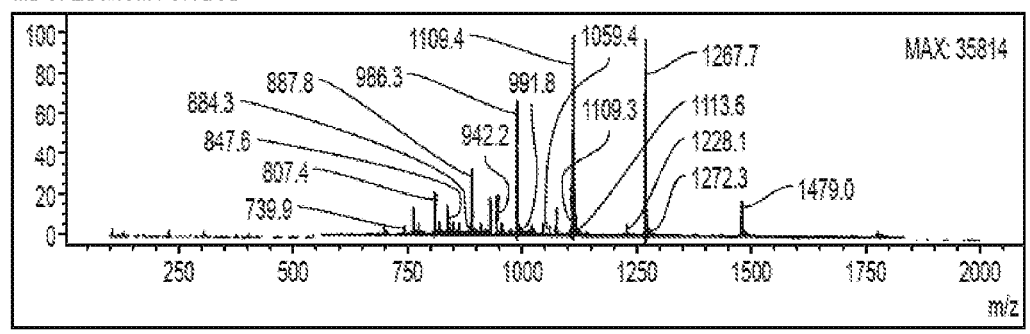
FIG. 22 shows characterization data for DSU.
Figure 22:
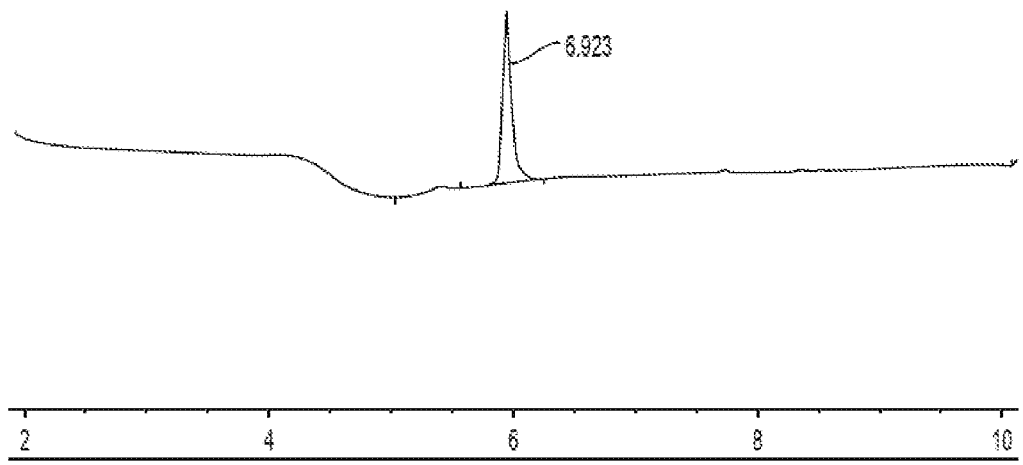
Figure 23:
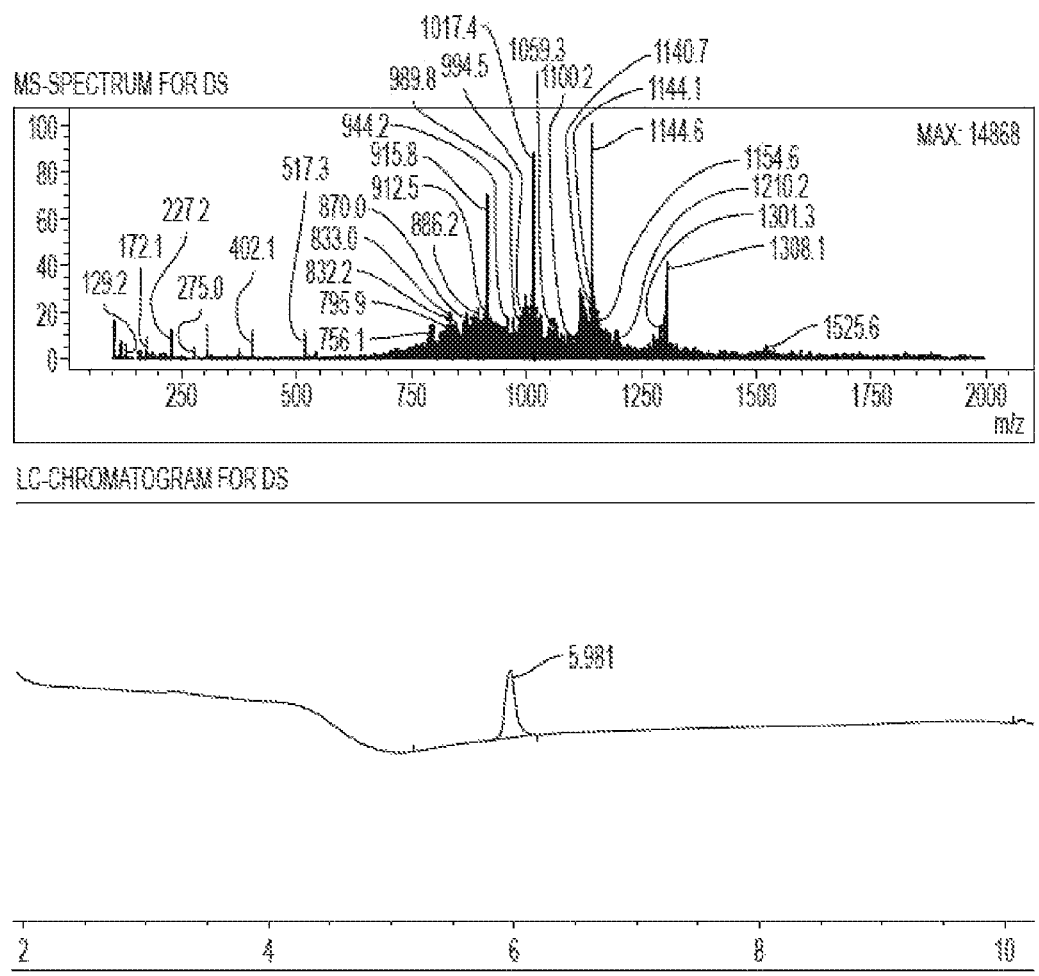
FIG. 23 shows characterization data for DS.

As shown in FIG. 19, double stapling can provide Bcr-Abl inhibitors. With the same reaction condition designed for single-stapling the protein (above), the thiol-ene reaction was performed with the four cysteine mutated protein and 1,3 diallylurea; the conversion was 80%. The reaction condition were: 1,3 diallylurea (5 equiv) was reacted with VA044 (1 equiv) in the presence of GSH (1 equiv), acetate buffer, 6 N Gdn, and HCl under exposure to hv at 365 nm for 15 minutes. FIG. 20 shows characterization data for SSU. FIG. 21 shows characterization data for SS. FIG. 22 shows characterization data for DSU. FIG. 23 shows characterization data for DS.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

---

What is claimed is:

1. A method of stapling a peptide having at least four thiol functionalities with a linker having two alkene functionalities, the method comprising reacting two of the thiol functionalities with the two alkene functionalities, wherein reacting is a thiol-ene reaction, and reacting two further thiol functionalities in the peptide and two further alkene functionalities in a further linker.

2. The method of claim 1, wherein two of the thiol functionalities are contained in two cysteine residues in the peptide.

3. The method of claim 1, wherein the peptide contains all natural residues.

4. The method of claim 1, wherein reacting is via a Michael addition.

5. A method of preparing a stapled peptide, the method comprising the steps of:

a) providing a peptide having a structure selected from:

(SEQ ID NO:1)
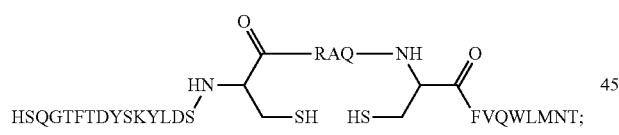

(SEQ ID NO:2)
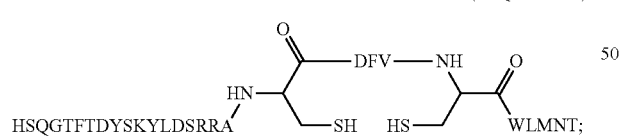

(SEQ ID NO:3)
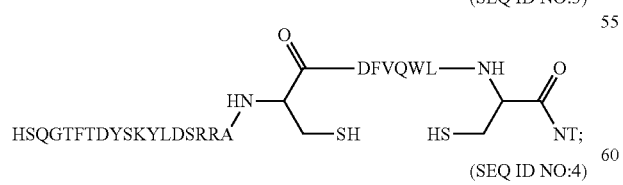

(SEQ ID NO:4)
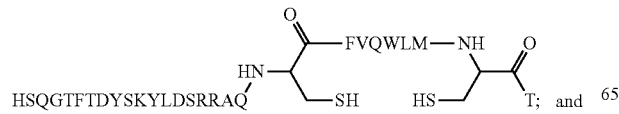

(SEQ ID NO:5)
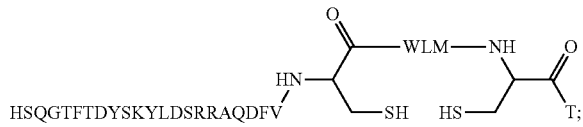

b) providing a diene having the structure represented by the formula:

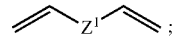

wherein $Z^1$ is C1-C8 alkyl, C3-C8 ether, or C6-C8 polyether, or wherein $Z^1$ is a moiety represented by a formula:

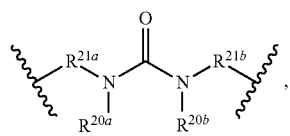

wherein each of $R^{20a}$ and $R^{20b}$ is independently selected from hydrogen and C1-C4 alkyl; and wherein each of $R^{21a}$ and $R^{21b}$ is independently C3-C6 alkylene;

or wherein $Z^1$ is a moiety represented by a formula:

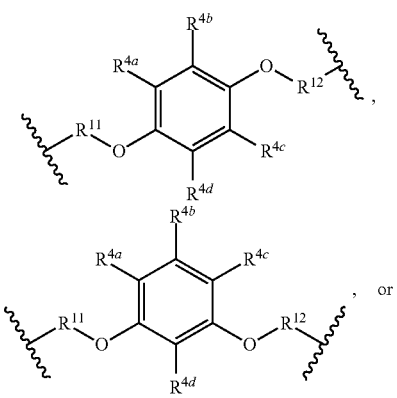

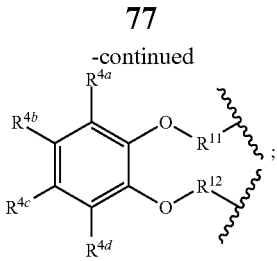

wherein each of $R^{4a}$, $R^{4b}$, $R^{4c}$, and $R^{4d}$ is independently hydrogen, hydroxy, amino, C1-C4 alkyl, and —$CO_2H$; and wherein each of $R^{11}$ and $R^{12}$ is independently C1-C4 alkyl;

c) reacting the peptide and the diene; thereby forming the stapled peptide.

6. The method of claim 5, wherein reacting is via a Michael addition.

7. The method of claim 5, further comprising a second reaction between two further thiol functionalities in the peptide and two further alkene functionalities in a further linker.

8. A method of stapling a peptide having two thiol functionalities with a linker having two alkene functionalities, the method comprising reacting the two thiol functionalities with the two alkene functionalities, wherein reacting is a thiol-ene reaction, wherein the peptide has the sequence

```
                                        (SEQ ID NO: 1)
HSQGTFTSDYSKYLDSCRAQCFVQWLMNT, (SEQ ID NO: 2)
HSQGTFTSDYSKYLDSRRACDFVCWLMNT, (SEQ ID NO: 3)
HSQGTFTSDYSKYLDSRRACDFVQWLCNT, (SEQ ID NO: 4)
HSQGTFTSDYSKYLDSRRAQCFVQWLMCT,
or (SEQ ID NO: 5)
HSQGTFTSDYSKYLDSRRAQDFVCWLMCT.
```

9. The method of claim 8, wherein reacting is via a Michael addition.

10. The method of claim 5, wherein the diene is a compound having a structure:

11. The method of claim 5, wherein reacting is a free radical thiol-ene reaction, and is in the presence of a radical initiator.

12. The method of claim 11, wherein the radical initiator is a photoinitiator.

13. The method of claim 12, wherein the photoinitiator is 2,2-dimethoxy-2-phenylacetophenone, 9,10-dioxo-9,10-dihydroanthracene-2-sulfonic acid, or (phenylphosphoryl)bis(mesitylmethanone).

14. The method of claim 1, wherein reacting is a free radical thiol-ene reaction.

15. The method of claim 1, wherein reacting is in the presence of radical initiator.

* * * * *